United States Patent
Iwata et al.

(10) Patent No.: US 11,739,331 B2
(45) Date of Patent: Aug. 29, 2023

(54) PARP9 AND PARP14 AS KEY REGULATORS OF MACROPHAGE ACTIVATION

(71) Applicant: THE BRIGHAM AND WOMEN'S HOSPITAL, INC., Boston, MA (US)

(72) Inventors: Hiroshi Iwata, Brookline, MA (US); Masanori Aikawa, Chestnut Hill, MA (US); Takuya Hara, Fuji (JP); Sasha Singh, Boston, MA (US); Piero Ricchiuto, Milan (IT); Hideo Yoshida, Brookline, MA (US); Iwao Yamada, Boston, MA (US)

(73) Assignee: THE BRIGHAM AND WOMEN'S HOSPITAL, INC., Boston, MA (US)

( * ) Notice: Subject to any disclaimer, the term of this patent is extended or adjusted under 35 U.S.C. 154(b) by 346 days.

(21) Appl. No.: 16/874,371

(22) Filed: May 14, 2020

(65) Prior Publication Data

US 2020/0325482 A1 Oct. 15, 2020

Related U.S. Application Data

(62) Division of application No. 15/036,249, filed as application No. PCT/US2014/065697 on Nov. 14, 2014, now Pat. No. 10,689,651.

(60) Provisional application No. 61/904,241, filed on Nov. 14, 2013.

(51) Int. Cl.
*A61K 31/519* (2006.01)
*C12N 15/113* (2010.01)

(52) U.S. Cl.
CPC ........ *C12N 15/1137* (2013.01); *A61K 31/519* (2013.01); *C12N 2310/14* (2013.01); *C12Y 204/0203* (2013.01)

(58) Field of Classification Search
CPC .............................. A61K 31/519; A61P 29/00
See application file for complete search history.

(56) References Cited

U.S. PATENT DOCUMENTS

2011/0097329 A1 4/2011 Chang et al.
2013/0156776 A1 6/2013 Chang et al.

FOREIGN PATENT DOCUMENTS

WO 2012097126 A2 7/2012
WO WO 2016201257 * 12/2016

OTHER PUBLICATIONS

Barbarulo et al., "Poly (ADP-ribose) polymerase family member 14 (PARP14) is a novel effector of the JNK2-dependent pro-survival signal in multiple myeloma." Oncogene 32(36):4231-4242 (2013).
Hakme et al., "The macroPARP genes Parp-9 and Parp-14 are developmentally and differentially regulated in mouse tissues," Dev. Dyn., 237(1):209-15 (2008).
Isidro-Llobet et al. "Diversity-oriented synthesis of macrocyclic peptidomimetics." PNAS 108(17):6793-6798 (2011).
Japanese Biochemical Society Meeting—Poster—The Journal of Biochemistry, Abstract CD, p. 3p-0512 (2007)—English Translation.
Lawrence et al., "Transcriptional regulation of macrophage polarization: enabling diversity with identity." Nature Reviews Immunology 11(11):750-761 (2011).
Mantovani et al. "The chemokine system in diverse forms of macrophage activation and polarization," Trends in Immunology, 25(12):677-686 (2004).
Welsby et al., "Complex roles of members of the ADP-ribosyl transferase super family in immune defences: looking beyond PARP1," Bichem. Pharmacol., 84(1):11-20 (2012).

* cited by examiner

*Primary Examiner* — Noble E Jarrell
(74) *Attorney, Agent, or Firm* — Nixon Peabody LLP; David S. Resnick; Jeanne Jodoin

(57) ABSTRACT

The invention relates to compositions and methods for inhibiting macrophage activation via modulating PARP9 and/or PARP14 expression or activity, such as small molecules, RNAi and antibodies.

3 Claims, 56 Drawing Sheets

Specification includes a Sequence Listing.

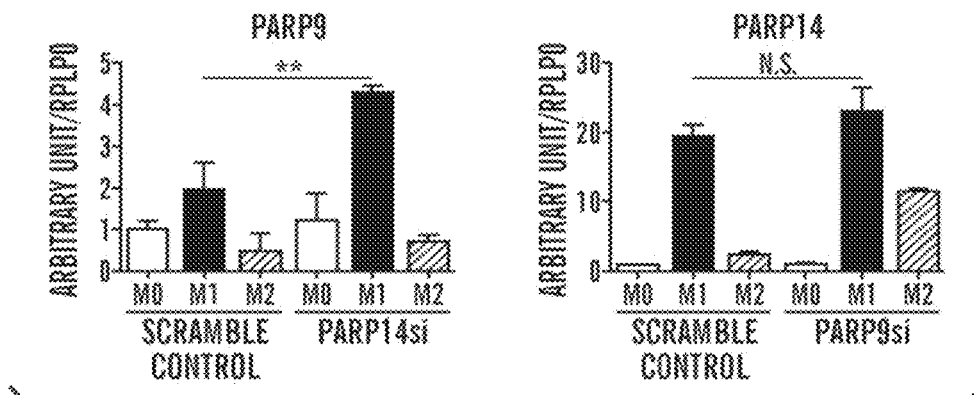
FIG. 10A
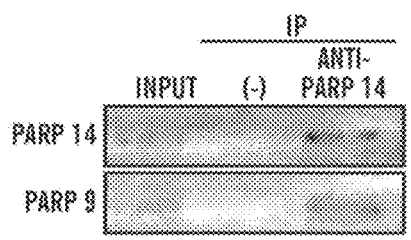
FIG. 10B
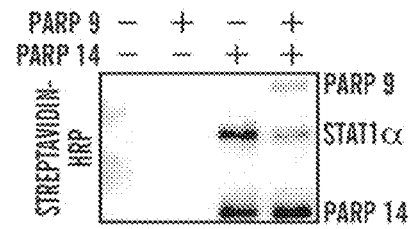
FIG. 10C
STAT1α c-TERMINUS
653 VMAAENIPENPLKYLYPNIDKDHAFGKYYSRPKEAPEPMELDGPKTG
YIKTELTSVSEVHPSRLQTTDNLLPMSPEEFDEVSRIVGSVEFDSMMNTV 750
(SEQ ID NO: 52)
FIG. 10D

PARP9 AND PARP14 AS KEY REGULATORS OF MACROPHAGE ACTIVATION

CROSS-REFERENCE TO RELATED APPLICATIONS

This application is a divisional under 35 U.S.C. § 121 of co-pending U.S. application Ser. No. 15/036,249 filed May 12, 2016, which is a 35 U.S.C. § 371 National Phase Entry application of International Application No. PCT/US2014/065697 filed Nov. 14, 2014, which designates the U.S., and which claims the benefit under 35 U.S.C. § 119(e) of U.S. Provisional Application No. 61/904,241 filed Nov. 14, 2013, the contents of each of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Dec. 22, 2014, is named 043214-079711-PCT_SL.txt and is 11,257 bytes in size.

TECHNICAL FIELD

This disclosure relates to methods of modulating macrophage activation and inflammation.

BACKGROUND

The immune system in an organism functions to protect against infection by identifying and killing foreign pathogens. It is made up of special cells, proteins, tissues, and organs. It detects pathogens ranging from viruses to parasitic worms and distinguishes them from the organism's normal cells and tissues. But sometimes the immune system fails to function properly and this can lead to illness. For example, deregulation of the inflammatory response, such as sustained activation of macrophages, can occur, provoking inflammatory diseases. Inflammation plays crucial roles in the pathogenesis of various chronic diseases, including atherosclerosis, metabolic disorders such as diabetes, autoimmune diseases, cancer, rheumatoid arthritis, inflammatory bowel disease, systemic lupus erythematosus, and multiple sclerosis. Theses chronic inflammatory diseases affect almost half a billion of people worldwide and they represent major health problems and economic burden on our society. Moreover, many of these diseases are debilitating and are becoming increasingly common in our aging society.

Chronic low-grade inflammation, which is primarily mediated by innate and adaptive immune cells, has emerged as a key excessive or sustained link between obesity and metabolic disorders including dyslipidemia and diabetes. Moreover, it is widely accepted that atherosclerosis is a chronic inflammatory disorder. Chronic inflammatory processes in arteries lead to atherosclerotic plaque formation resulting in tissue ischemia, including acute myocardial infarction and stroke. Autoimmune diseases including rheumatoid arthritis (RA) and systemic lupus erythematosus (SLE) are characterized by the body's immune responses being directed against its own tissues, causing prolonged inflammation and subsequent tissue destruction. And also, it is well known that inflammation is crucial for cancer development, progression and metastasis. In these inflammatory situations where the immune systems is not engaged in protecting the host from infection or injury and promoting tissue repair, macrophages activation critically participates in such uncontrolled sustained inflammation which contributes to various diseases. Thus, new methods to control pathological activation of macrophages are useful.

BRIEF DESCRIPTION OF DRAWINGS

FIG. 2A shows the MS2 spectra for PARP14 peptides identified in RAW264.7 polarization M0, M1 and M2 experiments. The major b and y ions are indicated. The inset contains the TMT reporter ion channels and their corresponding time points. Lower case letters indicate TMT labeled amino acids.

FIG. 2B shows tandem mass tagging-derived relative protein abundance profiles for PARP14 and PARP9 from M0, M1 and M2 datasets in mouse RAW264.7 and human THP-1 cells. PARP14 increased in M1, decreased in M2, and did not significantly change in M0 in both cell lines. PARP9, which is known to share 1-3 macrodomains connected to a PARP domain with PARP14 as "macro PARPs", also increased in M1 and decreased in M2 in both RAW264.7 and THP-1.

FIG. 2C shows the PARP9 and PARP14 mRNA expression patterns in macrophage polarization at 24 hours after stimulation (n=3). (* and ** indicate p<0.05 and p<0.01 by ANOVA, respectively.). Similar to proteomics data, PARP14 and PARP9 significantly increased in M1 stimuli (supplementation of IFNγ for 24 hours) and decreased in M2 stimuli (supplementation of IL4 for 24 hours) in THP-1.

FIG. 2D shows the PARP9 and PARP14 protein expression was confirmed by western blotting. Consistent with proteomics and mRNA, both PARP9 and PARP14 increased in M1 and decreased in M2 at 24 hours after starting stimuli.

FIG. 3A shows that in mouse macrophage cell line RAW264.7, silencing PARP14 gene by small interfering RNA (siRNA) induced significant elevation of M1 marker genes, such as TNFα (TNF) and iNOS (NOS2), and significant decrease of M2 maker gene MRC1 (Mrc1).

FIG. 3B shows that similarly, in human macrophage cell line THP-1, silencing PARP14 gene induced significant elevation of M1 marker genes, such as TNFα (TNF) and IL-1β (IL1B), and significant decrease of M2 maker gene MRC1 (Mrc1).

FIG. 3C shows that in THP-1 cells (n=3), release of M1 markers, as well as inflammatory cytokines (TNFα, IL-1β) into supernatant was significantly promoted by silencing PARP14.

FIG. 3D shows that in cultured human CD14+ peripheral blood mononuclear cells (PBMCs), significant increase of TNFα gene and decrease of MRC1 gene were induced by PARP14 silencing. Each dot indicates averages of quadruplicate in respective genes of respective donors (3 donors in total).

FIG. 3E shows that PARP14 silencing induced significant increase of PARP9. Conversely, PARP14 gene tended to increase by PARP9 silencing.

FIG. 3F shows that in contrast to PARP14 silencing, PARP9 silencing induced significant decrease of M1 marker genes, such as TNFα (TNF), IL-1β (IL1B) and CCL2 (CCL2), and increase of MRC1 (Mrc1) gene (THP-1, N=3).

FIG. 4A shows that PARP14 silencing induced increase in phosphorylation of STAT1 in M1 environment (IFNγ 10 ng/mL for 30 minutes), while no significant change in total STAT1. On the other hand, it induced remarkable reduction of phosphorylation of STAT6 in M2 (IL4 10 ng/mL for 30 minutes) (THP-1, N=3).

FIG. 4B shows that similarly, ELISA of phosho-STAT6 and total-STAT6 quantitatively showed significant decrease of phosphorylation of STAT6 in M2.

FIG. 4C shows that in contrast to PARP14 silencing, reduction in phosphorylation of STAT1 in M1 was induced by PARP9 silencing with no significant change in total-STAT1, but no significant change in that of STAT6 in M2 was observed (THP-1, N=3).

FIG. 4D shows that that phosphorylation of STAT3 was affected by neither PARP9 nor PARP14 silencing.

FIG. 5A shows that M1 marker genes ((iNOS (Nos2) and TNFα (TNF)) in M1 stimuli were significantly higher and M2 marker genes (MRC1 (Mrc1) and Arg1 (Arg1)) in M2 stimuli were significantly lower in PARP14−/− than those in PARP+/+ mice (N=3)

FIG. 5B shows the densitometry of western blotting revealed that ratio of phosphorylated STAT1 to total STAT1 (tSTAT1) was significantly higher and that of phosphorylated STAT6 (pSTAT6) to total STAT6 (pSTAT1/tSTAT6) was significantly lower in in PARP14−/− mice than that in PARP14+/+ mice. Each dot in graphs represents average of duplicate samples in respective donors (3 donors in total).

FIG. 5C shows that the secretion of TNFα and nitric oxide by peritoneal macrophages were significantly higher in PARP14−/− mice compared to PARP14+/+ mice.

FIG. 5D shows that similarly, in bone marrow macrophages, M1 marker genes (iNOS (Nos2) and TNFα (TNF)) in M1 stimuli were significantly higher and M2 marker genes (MRC1 (Mrc1) was lower in PARP14−/− mice. Another M2 marker gene, Arg1 (Arg1) tended to be lower in PARP14−/− mice, but without significance. Each dot in graphs represents average of quadruplicate samples in respective donors (5 donors in total).

FIG. 7A is a heat map demonstrating hierarchical clustering of proteins determined to increase in M1, decrease in M2 and show no significant change in M0. n=490 proteins for RAW264.7 cells and n=414 proteins THP-1 cells. Each row corresponds to a protein gene ID.

FIG. 7B is a heat map showing hierarchical clustering of 38 proteins from FIG. 7A that were identified in both RAW264.7 and THP-1 datasets. Each row corresponds to a protein gene ID.

FIG. 9A shows PARP14 and PARP9 protein expression visualized by Western blot. The relative protein abundances of PARP14 and PARP9 normalized to β-actin were quantified (graph, n=3).

FIG. 9B shows PARP14 and PARP9 expression in atherosclerotic plaques from the aorta of an Apoe$^{-/-}$ mouse fed a high-fat diet. Scale bars indicate 100 μm.

FIGS. 10A-10F show the potential interaction of PARP9 and PARP14.

FIG. 10A shows that PARP14 silencing significantly increased PARP9 gene expression in M1 (THP-1, n=3).

FIG. 10B shows that co-immunoprecipitation (IP) assay revealed a complex between PARP9 and PARP14.

FIG. 10C shows that PARP9 inhibits ADP-ribosylation of STAT1α by PARP14 (protein ribosylation assay). PARP14 auto-ribosylation is also indicated.

FIG. 10D shows the amino acid sequence of human STAT1α C-terminus. Underlined amino acids indicate ribosylated peptides; ribosylation sites are in boxes. STAT1 is known to be phosphorylated at Y701.

FIG. 10E shows MS/MS spectra for the two mono-ADP-ribosylated peptides and their corresponding unmodified forms. Arrows point to ADP-ribose fragments. *, ribosylation site; m, oxidized Met. The grey circles indicate background ions.

FIG. 10F shows MS1 based quantification of PARP9 inhibition of PARP14-mediated STAT1α ribosylation. AUC, area under the curve.* and ** indicate p<0.05 and p<0.01 by Student's t-test, respectively.

FIGS. 11A-11C show cultured peritoneal macrophages derived from PARP14$^{-/-}$ and PARP14$^{+/+}$ mice.

FIG. 11A shows M1 and M2 gene expression profiles (n=3).

FIG. 11B shows secretion of inflammatory factors into culture media (n=3).

FIG. 11C shows western blot and corresponding densitometry quantification of phosphorylated STAT1 and STATE. Each data point is the average of triplicate samples per donor (n=3).

FIG. 11D shows M1 and M2 gene expression data from bone marrow derived macrophages from PARP14$^{-/-}$ and PARP14$^{+/+}$ mice. Each data point is the average of quadruplicate samples per donor (n=5).

FIG. 11E shows quantification of lesion formation in mechanically-injured femoral arteries of PARP14$^{-/-}$ and PARP$^{+/+}$ mice. Mac3 staining represents macrophage accumulation (n=5).

FIG. 11F shows laser capture microdissection (LCM) of the neointima followed by gene expression analysis (n=4).

FIGS. 13A-13C show a model for macrophage polarization incorporating the novel findings described herein on PARP14 and PARP9.

FIG. 13A shows heterogeneity in M1 compared to M0 cells in combined 3 donors and each donor.

FIG. 13B shows comparison of genes related to macrophage function between Group1 and 2. Group1 and 2 can be derived from a similarity map of cells from all donors/conditions reveals three subpopulations (data not shown); IFNγ-stimulated M1 cells (1), unstimulated M0 cells (2) and mixed populations (3). There are two further subpopulations within M1 (1) (Group 1 and 2).

FIG. 13C is a gene similarity map of PARP9/14, STAT, JAK and IRF genes.

FIG. 13D is a schematic of working hypothesis.

FIG. 13E is a schematic workflow of the target discovery research. Fully integrated target discovery research from global screening to comprehensive validations to drug development.

SUMMARY

Figure 1A:
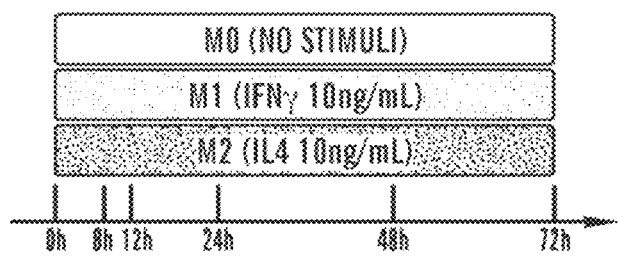
FIG. 1A shows the cell culture protocol used for high throughput screening of whole proteome in macrophage polarization. Interferon gamma (IFNγ) 10 ng/mL was supplemented for up to 72 hours to polarize primary or cell-line macrophages for proinflammatory phenotype (M1). Interleukin 4 (IL4) 10 ng/mL was used for anti-inflammatory phenotype (M2). M0 was defined as culturing macrophages without stimuli.

Embodiments of the present disclosure are based on the discovery that poly (ADP-ribose) polymerase family, member 9 (PARP9) and poly (ADP-ribose) polymerase family, member 14 (PARP14) are modulators of non-activated, non-polarized macrophages and their precursors, monocytes. Silencing of the PARP14 gene induced pro-inflammatory M1 genes (TNFα, IL-1β and iNOS), while decrease anti-inflammatory M2 markers (Arg1 and MRC1), indicating that PARP14 suppresses M1 pro-inflammatory macrophage activation and promotes anti-inflammatory M2 polarization. In contrast, siRNA silencing experiments demonstrated that PARP9 promotes M1 activation.

Accordingly, modulating the expression and/or activity of PARP9 and/or PARP14 allows the inhibition of monocytes or macrophage M1 activation and inflammation. For example, inhibiting undesirable excessive or sustained inflammation found in humans, for the treatment, prevention and/or management of conditions where undesirable excessive or sustained inflammation is known or likely to contribute to the onset, development and/or progression the conditions.

It is the objective of this disclosure to provide methods of inhibition of pro-inflammatory activation of monocytes or macrophages (e.g., M1 activation).

It is the objective of this disclosure to provide methods of inhibition of monocytes or macrophage M1 activation.

It is also the objective of this disclosure to provide methods of inhibiting undesirable excessive or sustained macrophage activation or inflammation found in humans.

It is also the objective of this disclosure to provide methods of treatment and/or prevention and/or management of conditions where undesirable excessive or sustained macrophage activation or inflammation is known or likely to contribute to the onset, development and/or progression the conditions.

It is also the objective of this disclosure to provide methods for the treatment and/or prevention of the development or clinical complications of chronic atherosclerosis and/or other chronic or acute arterial or venous diseases in humans (e.g., in-stent restenosis of coronary arteries, vein graft failure, and vasculitis).

Accordingly, in one embodiment, provided herein is a method of inhibiting pro-inflammatory macrophage activation, such as M1 activation, comprising contacting a population of monocytes or macrophages with an effective amount of a composition comprising an inhibitor of PARP9 and/or an activator of PARP14.

In one embodiment, provided herein is a method of inhibiting macrophage M1 activation comprising contacting a population of monocytes or macrophages with an effective amount of a composition comprising an inhibitor of PARP9 and/or an activator of PARP14.

In one embodiment, also provided herein is a method of inhibiting pro-inflammatory macrophage activation, such as M1 activation, comprising contacting a population of monocytes or macrophages with an effective amount of a composition comprising an inhibitor of PARP9.

In one embodiment, also provided herein is a method of inhibiting macrophage M1 activation comprising contacting a population of monocytes or macrophages with an effective amount of a composition comprising an inhibitor of PARP9.

In one embodiment, provided herein is a method of inhibiting pro-inflammatory macrophage activation, such as M1 activation, comprising contacting a population of monocytes or macrophages with an effective amount of a composition comprising an activator of PARP14.

In one embodiment, provided herein is a method of inhibiting macrophage M1 activation comprising contacting a population of monocytes or macrophages with an effective amount of a composition comprising an activator of PARP14.

In one embodiment, provided herein is a method of inhibiting pro-inflammatory macrophage activation, such as M1 activation, comprising contacting a population of monocytes or macrophages with an effective amount of a composition comprising an inhibitor of PARP9 and an activator of PARP14.

In one embodiment, provided herein is a method of inhibiting macrophage M1 activation comprising contacting a population of monocytes or macrophages with an effective amount of a composition comprising an inhibitor of PARP9 and an activator of PARP14.

In one embodiment, provided herein is a method of inhibiting pro-inflammatory macrophage activation, such as M1 activation, comprising the steps of (a) providing a population of monocytes or macrophages or a mixture of both cell types; and (b) contacting the population of monocytes or macrophages with an effective amount of a composition comprising an inhibitor of PARP9 and/or an activator of PARP14.

In one embodiment, provided herein is a method of inhibiting macrophage M1 activation comprising the steps of (a) providing a population of monocytes or macrophages or a mixture of both cell types; and (b) contacting the population of monocytes or macrophages with an effective amount of a composition comprising an inhibitor of PARP9 and/or an activator of PARP14.

In one embodiment, provided herein is a method of treating and/or preventing atherosclerosis and/or a vascular disease in a subject in need thereof comprising contacting a population of monocytes and/or macrophages from the subject with an effective amount of a composition comprising of an inhibitor of PARP9 and/or an activator of PARP14.

In one embodiment, provided herein is a method of inhibiting excessive or sustained macrophage activation or inflammation in a subject in need thereof comprising contacting a population of monocytes and/or macrophages from the subject with an effective amount of a composition comprising an inhibitor of PARP9 and/or an activator of PARP14.

In one embodiment, provided herein is a method of inhibiting excessive or sustained macrophage activation or inflammation in a subject in need thereof comprising administering to the subject an effective amount of a pharmaceutical composition comprising of an inhibitor of PARP9 and/or an activator of PARP14 and a pharmaceutically acceptable carrier or diluent.

In one embodiment, provided herein is a method of treating or preventing atherosclerosis and/or an arterial or venous disease in a subject in need thereof comprising the step of (a) identifying a subject who has or is at risk of atherosclerosis and/or a vascular disease; and (b) administering to the subject an effective amount of a pharmaceutical composition comprising of an inhibitor of PARP9 and/or an activator of PARP14 and a pharmaceutically acceptable carrier or diluent. In one embodiment, the treatment or prevention of atherosclerosis and/or an arterial or venous disease comprises treating or preventing the development or clinical complications of atherosclerosis and/or an arterial or venous disease.

In one embodiment, provided herein is a method of treating or preventing the development or clinical complications of atherosclerosis and/or an arterial or venous disease in a subject in need thereof comprising the step of (a) identifying a subject who has or is at risk of atherosclerosis and/or a vascular disease; and (b) administering to the subject an effective amount of a pharmaceutical composition comprising of an inhibitor of PARP9 and/or an activator of PARP14 and a pharmaceutically acceptable carrier or diluent.

In one embodiment, provided herein is a method of inhibiting excessive or sustained macrophage activation or inflammation in a subject in need thereof comprising the step of (a) identifying a subject who has or is at risk of excessive or sustained inflammation; and (b) administering to the subject an effective amount of a pharmaceutical composition comprising of an inhibitor of PARP9 and/or an activator of PARP14 and a pharmaceutically acceptable carrier or diluent.

In one embodiment of any one method, the atherosclerosis in chronic, meaning the atherosclerosis has been occurring for at least the past 3 months.

In one embodiment of any one method, the vascular disease is acute or chronic.

In one embodiment of any one method, the vascular disease includes but is not limited to coronary artery atherosclerosis, carotid artery atherosclerosis, peripheral artery (or arterial) disease, in-stent restenosis, renal artery disease, diabetic vasculopathy, vasculitis (e.g., Behçet's disease, giant cell arteritis, Takayasu's arteritis, Buerger's disease, Kawasaki disease), aortic aneurysms, cerebrovascular disease, transplant arteriopathy, narrowing or occlusion of vein grafts for peripheral artery (or arterial) disease, narrowing or occlusion of vein grafts for coronary arteries, narrowing or occlusion of AV fistulas/grafts, narrowing or occlusion of tissue-engineered vessels.

In one embodiment of any one method, the vascular disease includes but is not limited to vascular complications (ie., complications involving blood vessels in the body) in acute myocardial infarction (AMI), cardiac remodeling/dysfunction after AMI, heart failure, stroke, brain damage after stroke, limb ischemia and vasculogenic erectile dysfunction.

In one embodiment of any one method, the inhibition of macrophage M1 activation comprises inhibiting pro-inflammatory M1 polarization in the monocytes and/or macrophages.

In one embodiment of any one method, the inhibition of macrophage activation comprises inhibiting pro-inflammatory polarization, such as M1, in the monocytes and/or macrophages.

In one embodiment of any one method, the inhibition of pro-inflammatory M1 polarization in the monocytes and/or macrophages comprises the suppression of a pro-inflammatory M1 gene expression.

In one embodiment of any one method, the inhibition of pro-inflammatory polarization in the monocytes and/or macrophages comprises the suppression of a pro-inflammatory gene expression. Monocyte/macrophage activation could be assessed by any forms of pro-inflammatory polarization other than M1.

In one embodiment of any one method, the inhibition of excessive or sustained inflammation comprises inhibiting pro-inflammatory M1 polarization in the monocytes and/or macrophages.

In one embodiment of any one method, the inhibition of excessive or sustained inflammation comprises inhibiting pro-inflammatory polarization, such as M1 polarization, in the monocytes and/or macrophages.

In one embodiment of any one method, the inhibition of macrophage activation comprises increasing the expression of an anti-inflammatory M2 marker in the monocytes and/or macrophages.

In one embodiment of any one method, whereby the pro-inflammatory M1 polarization of contacted monocytes and/or macrophages in the subject is inhibited.

In one embodiment of any one method, whereby the pro-inflammatory polarization (e.g., M1) of contacted monocytes and/or macrophages in the subject is inhibited.

In one embodiment of any one method, whereby an anti-inflammatory M2 marker expression in monocytes and/or macrophages in the subject is increased.

In one embodiment of any one method, the pro-inflammatory M1 gene that is suppressed includes but is not limited to tumor necrosis factor alpha (TNF-α), interleukin-1β (IL-1β),), interleukin 6 (IL-6), interleukin 12 (IL-12), monocyte chemoattractant protein-1 (MCP-1), and inducible nitric oxide synthase (iNOS).

In one embodiment of any one method, the inhibition of macrophage activation comprises increasing the expression of an anti-inflammatory M2 marker.

In one embodiment of any one method, the anti-inflammatory M2 marker is arginase 1 (Arg1), mannose receptor, C type 1 (MRC1), IL-10, RHAMM (CD168), Resistin-like-α (Retnla; also known as Fizz1) and chitinase 3-like 3 (Chi313; also known as Ym1).

In one embodiment of any one method, the population of monocytes or macrophage is contacted ex vivo or in vitro or in vivo.

In one embodiment of any one method, the composition comprises a lipid encapsulation formulation of the inhibitor of PARP9 and/or the activator of PARP14.

In one embodiment of any one method, the inhibitor of PARP9 inhibits the expression of PARP9.

In one embodiment of any one method, the inhibitor of PARP9 is a small molecule or a nucleic acid.

In one embodiment of any one method, the nucleic acid is a PARP9 specific RNA interference agent, or a vector encoding a PARP9-specific RNA interference agent.

In one embodiment of any one method, the RNA interference agent hybridizes to a PARP9 nucleic acid sequence.

In one embodiment of any one method, the RNA interference agent is a siRNA directed specifically against a PARP9 gene.

In one embodiment of any one method, the PARP9-specific RNA interference agent is a siRNA, a ssRNA, a dsRNA, a shRNA or antisense oligonucleotides.

In one embodiment of any one method, the RNA interference agent comprises a nucleic sequence derived from the human PARP9 gene having a GENBANK™ Accession number BC039580.

In one embodiment of any one method, the PARP9-specific RNA interference agent comprises one or more of the nucleotide sequences selected from a group consisting of SEQ ID NOS: 1-28, 33-36, and 41-44.

In one embodiment of any one method, the PARP9-specific RNA interference agent nucleotide sequences include but are not limited to GATTTAACTTGTTCTGTAA (SEQ ID NO:1), TTGAAGATATGCTTTGTAA (SEQ ID NO:2), GCCATAGGCTGTTTCAGCA (SEQ ID NO:3), GTCTCCATCACAGAAATTA (SEQ ID NO:4), TGGTGGATTTGAAATCCAA (SEQ ID NO:5), GAGTTGAAATGAAATCGGA (SEQ ID NO:6), CTTTAAAGCTGCTTCAGAA (SEQ ID NO:7), ATGACAGTGTGGTTGACAA (SEQ ID NO:8), CAAACAGTTTGTTGCCAGA (SEQ ID NO:9), TCCTGTGCCTCCAACTCAA (SEQ ID NO:10), GACTGGTGCTCTTGGAGAA (SEQ ID NO:11), GGAAGCCAATGATGAGTAA (SEQ ID NO:12), TTCAGAATTTCCTAAACCT (SEQ ID NO:13), CTGGAAACATGGAAATAAA (SEQ ID NO:14), CTCTGAATTTGTGTACAAA (SEQ ID NO:15), CCATCATCTGATGGGATT (SEQ ID NO:16), CAGATAAGCTGATCTATGT (SEQ ID NO:17), GGGTTAGTTTGCAAGGGAA (SEQ ID NO:18), CAGATTTGGAGATATATAA (SEQ ID NO:19), TGCTGAGTTTGAACAATTA (SEQ ID NO:20), CCATTAACCACAATGACTT (SEQ ID NO:21), GCAGACGGCAGATGTAATT (SEQ ID NO:22), CCCACATGATATTACAGTT (SEQ ID NO:23), GCAGGAGTTGAAATGAAAT (SEQ ID NO:24), GCCATCAATCTGATGGGAT (SEQ ID NO:25), GCTGGTATGGCCTTACCTT (SEQ ID NO:26), CCTCTTGCAGTTGTTCTTT (SEQ ID NO:27), CCTTTACTAGAGGAGATAA (SEQ ID NO:28), AAUUACAUCUGCCGUCUGC (SEQ ID NO: 33), UUUGUGGCAAGAAAUUCCG (SEQ ID NO: 34), UUAAUCAACAGGGCUGCCA (SEQ ID NO: 35), UACAGCCAAACUUAUUCUG (SEQ ID NO: 36), ACACAAUGUCUUCGAAAUU (SEQ ID NO: 41), CCAGACAGCUAUCGAAUUA (SEQ ID NO: 42), CCAAAUAUGAUCUACGCAU (SEQ ID NO: 43), and CGUACACAUUUCAACGAUA (SEQ ID NO: 44).

In one embodiment of any one method, the inhibitor of PARP9 inhibits PARP9 protein's activity.

In one embodiment, the inhibitor of PARP9 activity interferes with PARP9 interactions with PARP9 binding partners. In some embodiments, the binding partners of PARP9 include STAT and ubiquitin ligase (DTX3L).

In one embodiment of any one method, the inhibitor of PARP9 is selected from the group consisting of an antibody against PARP9 or an antigen-binding fragment thereof, a small molecule, and a nucleic acid. In one embodiment of any one method, the inhibitor of PARP9 is an aptamer that binds to PARP9. Aptamers are oligonucleic acid or peptide molecules that bind to a specific target molecule.

In one embodiment of any one method, the activator of PARP14 increases the expression of PARP14 and/or PARP14 protein's activity.

In one embodiment of any one method, the activator of PARP14 is selected from the group consisting of an antibody against PARP9 or an antigen-binding fragment thereof, a small molecule, and a nucleic acid.

In one embodiment of any one method, the composition comprising the inhibitor of PARP9 and/or the activator of PARP14 further comprises a pharmaceutically acceptable carrier or diluent.

In one embodiment of any one method, the composition is administered by injection, infusion, or instillation.

In one embodiment of any one method, the pharmaceutical composition is administered by injection, infusion, or instillation.

In one embodiment of any one method, the pharmaceutical composition comprises a formulation comprising lipid encapsulation of the inhibitor of PARP9 and/or an activator of PARP14 and a pharmaceutically acceptable carrier or diluent.

In one embodiment of any one method, the excessive or sustained inflammation is found in a condition selected from the group consisting of but not limited to atherosclerosis, obesity, type 2 diabetes, vasculitis, limb ischemia, occlusion or narrowing of vein grafts, occlusion or narrowing of arteriovenous (AV) fistulas and/or grafts, fatty liver disease, brain damage after stroke, brain traumatic injury, cardiac remodeling after acute myocardial infarction, tissue engineered organs, transplanted organs, cancers, Gaucher's disease, autoimmune or autoinflammatory disease, inflammatory bowel disease, and cardiac valve diseases (e.g., aortic valve calcification, aortic stenosis).

In one embodiment of any one method, the autoimmune or autoinflammatory disease is selected from the group consisting of rheumatoid arthritis, lupus erythematosus, and Behçet's disease.

In one embodiment of any one method, further comprising selecting a subject having excessive or sustained inflammation.

In one embodiment of any one method, further comprises selecting a subject is at risk of developing a excessive or sustained inflammation.

In one embodiment of any one method, further comprising selecting a subject for administration of the pharmaceutical composition.

In one embodiment, also provided herein is a composition comprising an inhibitor of poly (ADP-ribose) polymerase family, member 9 (PARP9) and/or an activator of poly (ADP-ribose) polymerase family, member 14 (PARP14) for use in inhibiting macrophage M1 activation.

In one embodiment, also provided herein is a composition comprising an inhibitor of poly (ADP-ribose) polymerase family, member 9 (PARP9) and/or an activator of poly (ADP-ribose) polymerase family, member 14 (PARP14) for use in inhibiting macrophage activation such as M1 polarization.

In one embodiment, also provided herein is a composition comprising an inhibitor of poly (ADP-ribose) polymerase family, member 9 (PARP9) and/or an activator of poly (ADP-ribose) polymerase family, member 14 (PARP14) for use in the manufacture of a medicament for inhibiting macrophage M1 activation.

In one embodiment, also provided herein is a composition comprising an inhibitor of poly (ADP-ribose) polymerase family, member 9 (PARP9) and/or an activator of poly (ADP-ribose) polymerase family, member 14 (PARP14) for use in the manufacture of a medicament for inhibiting macrophage activation such as M1 polarization.

In one embodiment of any one composition, the composition comprises a lipid encapsulation formulation of the inhibitor of PARP9 and/or the activator of PARP14.

In one embodiment of any one composition, the inhibitor of PARP9 inhibits the expression of PARP9.

In one embodiment of any one composition, the inhibitor of PARP9 is a small molecule or a nucleic acid.

In one embodiment of any one composition, the nucleic acid is a PARP9 specific RNA interference agent, or a vector encoding a PARP9 specific RNA interference agent.

In one embodiment of any one composition, the RNA interference agent hybridizes to a PARP9 nucleic acid sequence.

In one embodiment of any one composition, the RNA interference agent comprises a nucleic sequence derived from the human PARP9 gene having a GENBANK™ Accession number BC039580.

In one embodiment of any one composition, the RNA interference agent comprises one or more of the nucleotide sequences selected from a group consisting of SEQ ID NOS: 1-28, 33-36, and 41-44.

In one embodiment of any one composition, the inhibitor of PARP9 inhibits PARP9 protein's activity.

In one embodiment of any one composition, the inhibitor of PARP9 is selected from the group consisting of an antibody against PARP9 or an antigen-binding fragment thereof, a small molecule, and a nucleic acid.

In one embodiment of any one composition, the activator of PARP14 increases the expression of PARP14 and/or PARP14 protein's activity.

In one embodiment of any one composition, the activator of PARP14 is selected from the group consisting of an antibody against PARP9 or an antigen-binding fragment thereof, a small molecule, and a nucleic acid.

Definitions

For convenience, certain terms employed in the entire application (including the specification, examples, and appended claims) are collected here. Unless defined otherwise, all technical and scientific terms used herein have the same meaning as commonly understood by one of ordinary skill in the art to which this invention belongs. Therefore, any subset of monocytes or macrophages that possesses pro-inflammatory signatures, as gauged by expression of certain genes or proteins or cell functions, can be a target of PARP9 or PARP 14 modulations.

As used herein, the term "comprising" or "comprises" is used in reference to methods, and respective component(s) thereof, that are essential to the invention, yet open to the inclusion of unspecified elements, whether essential or not. The use of "comprising" indicates inclusion rather than limitation.

In one embodiment, as used herein, the term "macrophage M1 activation" refers to the process of altering the functional activity of non-activated macrophages or monocytes so that they produce large amounts of TNF, IL-12, and IL-23 which help to drive antigen specific TH-1 and TH-17 cell inflammatory responses forward. In some embodiments, "macrophage M1 activation" refers to the transformation of a non-activated macrophage that results in the macrophage acquiring at least one of the following characteristics typical of activated M1 macrophage subtype: high capacity to present antigen; opsonic receptors [e.g. FcgRIII (CD16)]; high interleukin-12 (IL-12) production; high IL-23 production; low IL-10 production, high pro-inflammatory cytokines (IL-1, TNF and IL-6) production, consequent activation of a polarized type I response; high production of toxic intermediates such as nitric oxide (NO) from L-arginine, reactive oxygen species (ROS); and the production of inflammatory chemokines, such as CXCL1, 2, 3, 5, 8, 9 and 10 and CCL2, 3, 4, 5, 11, 17 and 22. But it should be noted that the approach described herein is not limited to this model of M1 polarization. Therefore, any subset of monocytes or macrophages that possesses pro-inflammatory signatures, as gauged by expression of certain genes or proteins or cell functions, can be a target of PARP9 or PARP14 modulations. In one embodiment, the methods and compositions described herein can be applicable to a subset or subpopulation of a population of M1-polarized macrophages.

As used herein, the term "inhibiting macrophage (M1) activation" means the halting, preventing or reducing macrophages from acquiring the phenotype characteristics typical of activated M1 macrophage subtype described herein. In some embodiment, the inhibiting is at least 5% lower of a macrophage M1 characteristic in the population of cells contacted or treated with a PARP9 inhibitor, than a comparable, control population of cells, wherein no PARP9 inhibitor is present. It is preferred that the percentage of PARP9 expression in a PARP9 inhibitor treated population of cells is at least 10% lower, at least 20% lower, at least 30% lower, at least 40% lower, at least 50% lower, at least 60% lower, at least 70% lower, at least 80% lower, at least 90% lower, at least 1-fold lower, at least 2-fold lower, at least 5-fold lower, at least 10 fold lower, at least 100 fold lower, at least 1000-fold lower, or more than a comparable control treated population of cells in which no PARP9 inhibitor is added.

As used herein, the term "M1 macrophage polarization" or "pro-inflammatory M1 polarization" in the method described herein refers to the shift of non-activated macrophage or monocytes towards developing phenotype characteristics typical of activated M1 macrophage subtype described herein instead of towards developing phenotype characteristics typical of activated M2 macrophage subtype.

In some embodiment, the phenotype characteristics typical of activated M2 macrophage subtype included but are not limited to low production of IL-2 and IL-23; high production of IL-10, high levels of scavenger, mannose, and galactose-type receptors; high production of IL-1-RA, IL-113, and caspase 1; high expression of decoyIL-1 type II receptor, and the production of inflammatory chemokines, such as CCL17, CCL22 and CCL24.

As used herein, the term "inhibiting pro-inflammatory M1 polarization" means the halting, preventing or reducing macrophages from shifting towards developing phenotype characteristics typical of activated M1 macrophage subtype described herein. In some embodiment, the inhibiting results in at least 5% lower of a macrophage M1 characteristic in the population of cells contacted or treated with a PARP9 inhibitor, than a comparable, control population of cells, wherein no PARP9 inhibitor is present. It is preferred that the percentage of PARP9 expression in a PARP9 inhibitor treated population of cells is at least 10% lower, at least 20% lower, at least 30% lower, at least 40% lower, at least 50% lower, at least 60% lower, at least 70% lower, at least 80% lower, at least 90% lower, at least 1-fold lower, at least 2-fold lower, at least 5-fold lower, at least 10 fold lower, at least 100 fold lower, at least 1000-fold lower, or more than a comparable control treated population of cells in which no PARP9 inhibitor is added.

In one embodiment, as used herein, the term "non-activated macrophages" refers to macrophages that have not acquired the phenotype characteristics typical of M1 and M2 macrophage subtypes that are known in the art and also described herein.

As used herein, the phrase "diseases that involve chronic inflammation" refers to any medical condition wherein chronic inflammation is observed as part of the medical condition and/or wherein chronic inflammation has been indicated to be a contributing factor to the initiation and/or progression of the medical condition. In one embodiment, the inflammation is mediated or accelerated by not only macrophages, but also various other cell types, including, but not limited to, T lymphocytes, B lymphocytes, dendritic cells, mast cells, endothelial cells, smooth muscle cells, hepatocytes, and fibroblasts. In one embodiment, chronic inflammation is a diagnostic symptom of a medical condition.

As used herein, the term "chronic inflammation" refers to prolonged and persistent inflammation marked chiefly by new connective tissue formation; it may be a continuation of an acute form or a prolonged low-grade form. In one embodiment, "chronic inflammation" means "excessive or sustained inflammation."

In one embodiment, as used herein, the term "excessive or sustained inflammation" refers to ongoing inflammatory responses that have gone beyond the homeostatic condition of providing the host with immune defense mechanisms adequate for protection against an acute infection or injury. In another embodiment, as used herein, the term "excessive or sustained inflammation" refers to ongoing inflammatory responses that is causing an unacceptable level of tissue damage as a result of the response and is not related to protection against an acute infection or injury.

As used herein, the term "inhibitor of PARP9" or PARP9 inhibitor" refers to any agent that inhibits PARP9 expression or inhibits PARP9 activity.

By "inhibits PARP9 expression" is meant that the amount of expression of PARP9 is at least 5% lower in the population of cells contacted or treated with a PARP9 inhibitor, than a comparable, control population of cells, wherein no PARP9 inhibitor is present. It is preferred that the percentage of PARP9 expression in a PARP9 inhibitor treated population of cells is at least 10% lower, at least 20% lower, at least 30% lower, at least 40% lower, at least 50% lower, at least 60% lower, at least 70% lower, at least 80% lower, at least 90% lower, at least 1-fold lower, at least 2-fold lower, at least 5-fold lower, at least 10 fold lower, at least 100 fold lower, at least 1000-fold lower, or more than a comparable control treated population of cells in which no PARP9 inhibitor is added.

By "inhibits PARP9 activity" is meant that the amount of functional activity of PARP9 is at least 5% lower in population of cells contacted or treated with a PARP9 inhibitor, than a comparable, control population of cells, wherein no PARP9 inhibitor is present. It is preferred that the percentage of PARP9 activity in a PARP9-inhibitor treated population is at least 10% lower, at least 20% lower, at least 30% lower, at least 40% lower, at least 50% lower, at least 60% lower, at least 70% lower, at least 80% lower, at least 90% lower, at least 1-fold lower, at least 2-fold lower, at least 5-fold lower, at least 10 fold lower, at least 100 fold lower, at least 1000-fold lower, or more than a comparable control treated/contacted population of cells in which no PARP9 inhibitor is added. At a minimum, PARP9 activity can be assayed by determining the amount of PARP9 expression at the protein or mRNA levels, using techniques standard in the art. Alternatively, or in addition, PARP9 activity can be assayed by measuring the expression of inflammatory factors including IL-113, TNFα, IL-6 at the mRNA or protein level following treatment or contact with a PARP9 inhibitor. Alternatively, or in addition, levels of PARP9 activity can be assayed by ADP-ribosylation of its target proteins.

As used herein, the term "activator of PARP14" or "PARP14 activator" refers to any agent that increases PARP14 expression or PARP14 protein activity.

As used herein, the phrase "activating or promoting of PARP14" means increases PARP14 expression or PARP14 protein activity.

By "increases PARP14 expression" is meant that the amount of expression of PARP14 is at least 5% higher in the population of cells contacted or treated with a PARP14 activator, than a comparable, control population of cells, wherein no PARP14 activator is present. It is preferred that the percentage of PARP14 expression in a PARP14 activator treated population of cells is at least 10% higher, at least 20% higher, at least 30% higher, at least 40% higher, at least 50% higher, at least 60% higher, at least 70% higher, at least 80% higher, at least 90% higher, at least 1-fold higher, at least 2-fold higher, at least 5-fold higher, at least 10 fold higher, at least 100 fold higher, at least 1000-fold higher, or more than a comparable control treated population of cells in which no PARP14 activator is added.

By "increases PARP14 activity" is meant that the amount of functional activity of PARP14 is at least 5% higher in population of cells contacted or treated with a PARP14 activator, than a comparable, control population of cells, wherein no PARP14 activator is present. It is preferred that the percentage of PARP14 activity in a PARP14-activator treated population is at least 10% higher, at least 20% higher, at least 30% higher, at least 40% higher, at least 50% higher, at least 60% higher, at least 70% higher, at least 80% higher, at least 90% higher, at least 1-fold higher, at least 2-fold higher, at least 5-fold higher, at least 10 fold higher, at least 100 fold higher, at least 1000-fold higher, or more than a comparable control treated/contacted population of cells in which no PARP14 activator is added. At a minimum, PARP14 activity can be assayed by determining the amount of PARP14 expression at the protein or mRNA levels, using techniques standard in the art. Alternatively, or in addition, PARP14 activity can be assayed by measuring the expression of chemokines CCL17, CCL22 and CCL24; cytokines IL-2, IL-23IL-10, IL-1-RA, IL-113, IL-6, caspase 1, and other pro-inflammatory molecules at the mRNA or protein level following treatment or contact with a PARP14 activator. Alternatively, or in addition, levels of PARP14 activity can be assayed by ADP-ribosylation of its target proteins.

The term "agent" refers to any entity that is normally not present or not present at the levels being administered to a cell, tissue or subject. Agent can be selected from a group comprising: chemicals; small molecules; nucleic acid sequences; nucleic acid analogues; proteins; peptides; aptamers; antibodies; or functional fragments thereof. A nucleic acid sequence can be RNA or DNA, and can be single or double stranded, and can be selected from a group comprising: nucleic acid encoding a protein of interest; oligonucleotides; and nucleic acid analogues; for example peptide-nucleic acid (PNA), pseudo-complementary PNA (pc-PNA), locked nucleic acid (LNA), etc. Such nucleic acid sequences include, but are not limited to nucleic acid sequence encoding proteins, for example that act as transcriptional repressors, antisense molecules, ribozymes, small inhibitory nucleic acid sequences, for example but not limited to RNAi, shRNAi, siRNA, micro RNAi (mRNAi), antisense oligonucleotides etc. A protein and/or peptide or fragment thereof can be any protein of interest, for example, but not limited to; mutated proteins; therapeutic proteins; truncated proteins, wherein the protein is normally absent or expressed at lower levels in the cell. Proteins can also be selected from a group comprising; mutated proteins, genetically engineered proteins, peptides, synthetic peptides, recombinant proteins, chimeric proteins, antibodies, midibodies, tribodies, humanized proteins, humanized antibodies, chimeric antibodies, modified proteins and fragments thereof. An agent can be applied to the media, where it contacts the cell and induces its effects. Alternatively, an agent can be intracellular as a result of introduction of a nucleic acid sequence encoding the agent into the cell and its transcription resulting in the production of the nucleic acid and/or protein environmental stimuli within the cell. In some embodiments, the agent is any chemical, entity or moiety, including without limitation synthetic and naturally-occurring non-proteinaceous entities. In certain embodiments the agent is a small molecule having a chemical moiety. For example, chemical moieties included unsubstituted or substituted alkyl, aromatic, or heterocyclyl moieties including macrolides, leptomycins and related natural products or analogues thereof. Agents can be known to have a desired activity and/or property, or can be selected from a library of diverse compounds.

As used herein, the term "small molecule" is a low molecular weight organic compound or chemical that is less than 1000 daltons. In one embodiment, a small molercule has size on the order of $10^{-9}$ meters.

As used herein, the term "pharmaceutically acceptable", and grammatical variations thereof, as they refer to compositions, carriers, diluents and reagents, are used interchangeably and represent that the materials are capable of administration to or upon a mammal without the production of undesirable physiological effects such as nausea, dizziness, gastric upset and the like. Each carrier must also be "acceptable" in the sense of being compatible with the other ingredients of the formulation. The preparation of a pharmacological composition that contains active ingredients dissolved or dispersed therein is well understood in the art and need not be limited based on formulation. The pharmaceutical formulation contains a compound of the invention in combination with one or more pharmaceutically acceptable ingredients. The carrier can be in the form of a solid, semi-solid or liquid diluent, cream or a capsule. Typically such compositions are prepared as injectable either as liquid solutions or suspensions, however, solid forms suitable for solution, or suspensions, in liquid prior to use can also be prepared. The preparation can also be emulsified or presented as a liposome composition. The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient. The therapeutic composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like. Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active agent used in the invention that will be effective in the treatment of a particular disorder or condition will depend on the nature of the disorder or condition, and can be determined by standard clinical techniques. The phrase "pharmaceutically acceptable carrier or diluent" means a pharmaceutically acceptable material, composition or vehicle, such as a liquid or solid filler, diluent, excipient, solvent or encapsulating material, involved in carrying or transporting the subject agents from one organ, or portion of the body, to another organ, or portion of the body. A pharmaceutically acceptable carrier will not promote the raising of an immune response to an agent with which it is admixed, unless so desired.

As used herein, "administered" refers to the placement of an inhibitor of PARP9 or activator of PARP14 into a subject by a method or route which results in at least partial localization of the inhibitor or activator at a desired site. An inhibitor of PARP9 and/or activator of PARP14 can be administered by any appropriate route which results in effective treatment in the subject, i.e. administration results in delivery to a desired location in the subject where at least a portion of the composition delivered, i.e. at least an inhibitor of PARP9 and/or activator of PARP14, is active in the desired site for a period of time. The period of time the inhibitor and/or activator is active depends on the half-life in vivo after administration to a subject, and can be as short as a few hours, e. g. twenty-four hours, to a few days, to as long as several years. Modes of administration include injection, infusion, instillation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In other embodiments, administration also includes aerosol inhalation, eg., with nebulization. In other embodiments, administration also can be systemic or local.

The term "effective amount" means a dosage sufficient to provide treatment for the disease state being treated. This will vary depending on the patient, the disease and the treatment being effected.

As used herein, the term "a therapeutically effective amount" refers an amount sufficient to achieve the intended purpose. For example, an effective amount of a composition comprising PARP 9 inhibitor that inhibits pro-inflammatory M1 polarization of macrophages and monocytes. An effective amount for treating or ameliorating a disorder, disease, or medical condition is an amount sufficient to result in a reduction or complete removal of the symptoms of the disorder, disease, or medical condition. The effective amount of a given therapeutic agent will vary with factors such as the nature of the agent, the route of administration, the size and species of the animal to receive the therapeutic agent, and the purpose of the administration. The effective amount in each individual case may be determined empirically by a skilled artisan according to established methods in the art In one embodiment, the term "treating" or "treatment" means to stabilize or improve the clinical symptoms of the subject. In another embodiment, "treating" or "treatment" also means to relieve or alleviate at least one symptom associated with such condition, or to slow or reverse the progression or anticipated progression of such condition, at bringing about ameliorations of the symptoms of the conditions described herein.

As used herein, the term "prevent" or "prevention" refers to stopping, hindering, and/or slowing down the onset of developing adverse effects and at least symptom associated with medical condition described herein.

As used herein, the term "vector" refers to a nucleic acid molecule capable of transporting another nucleic acid to which it has been linked. One type of vector is a "plasmid", which refers to a circular double stranded DNA loop into which additional nucleic acid segments can be ligated. Another type of vector is a viral vector, wherein additional nucleic acid segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors", or more simply "expression vectors." In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, lentiviruses, adenoviruses and adeno-associated viruses), which serve equivalent functions. In one embodiment, lentiviruses are used to deliver one or more siRNA molecule of the present invention to a cell.

Within an expression vector, "operably linked" is intended to mean that the nucleotide sequence of interest is linked to the regulatory sequence(s) in a manner which allows for expression of the nucleotide sequence (e.g., in an in vitro transcription/translation system or in a target cell when the vector is introduced into the target cell). The term "regulatory sequence" is intended to include promoters, enhancers and other expression control elements (e.g., polyadenylation signals). Such regulatory sequences are described, for example, in Goeddel; Gene Expression Technology: Methods in Enzymology 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). Furthermore, the RNA interfering agents may be delivered by way of a vector comprising a regulatory sequence to direct synthesis of the siRNAs of the invention at specific intervals, or over a specific time period. It will be appreciated by those skilled in the art that the design of the expression vector can depend on such factors as the choice of the target cell, the level of expression of siRNA desired, and the like.

The expression vectors of the invention can be introduced into target cells to thereby produce siRNA molecules of the present invention. In one embodiment, a DNA template, e.g., a DNA template encoding the siRNA molecule directed against the mutant allele, may be ligated into an expression vector under the control of RNA polymerase III (Pol III), and delivered to a target cell. Pol III directs the synthesis of small, noncoding transcripts which 3' ends are defined by termination within a stretch of 4-5 thymidines. Accordingly, DNA templates may be used to synthesize, in vivo, both sense and antisense strands of siRNAs which effect RNAi (Sui, et al. (2002) PNAS 99(8):5515).

An "antibody" that can be used according to the methods described herein includes complete immunoglobulins, antigen binding fragments of immunoglobulins, as well as antigen binding proteins that comprise antigen binding domains of immunoglobulins. Antigen binding fragments of immunoglobulins include, for example, Fab, Fab', F(ab')2, scFv and dAbs. Modified antibody formats have been developed which retain binding specificity, but have other characteristics that may be desirable, including for example, bispecificity, multivalence (more than two binding sites), and compact size (e.g., binding domains alone). Single chain antibodies lack some or all of the constant domains of the whole antibodies from which they are derived. Therefore, they can overcome some of the problems associated with the use of whole antibodies. For example, single-chain antibodies tend to be free of certain undesired interactions between heavy-chain constant regions and other biological molecules. Additionally, single-chain antibodies are considerably smaller than whole antibodies and can have greater permeability than whole antibodies, allowing single-chain antibodies to localize and bind to target antigen-binding sites more efficiently. Furthermore, the relatively small size of single-chain antibodies makes them less likely to provoke an unwanted immune response in a recipient than whole antibodies. Multiple single chain antibodies, each single chain having one VH and one VL domain covalently linked by a first peptide linker, can be covalently linked by at least one or more peptide linker to form multivalent single chain antibodies, which can be monospecific or multispecific. Each chain of a multivalent single chain antibody includes a variable light chain fragment and a variable heavy chain fragment, and is linked by a peptide linker to at least one other chain. The peptide linker is composed of at least fifteen amino acid residues. The maximum number of linker amino acid residues is approximately one hundred. Two single chain antibodies can be combined to form a diabody, also known as a bivalent dimer. Diabodies have two chains and two binding sites, and can be monospecific or bispecific. Each chain of the diabody includes a VH domain connected to a VL domain. The domains are connected with linkers that are short enough to prevent pairing between domains on the same chain, thus driving the pairing between complementary domains on different chains to recreate the two antigen-binding sites. Three single chain antibodies can be combined to form triabodies, also known as trivalent trimers. Triabodies are constructed with the amino acid terminus of a VL or VH domain directly fused to the carboxyl terminus of a VL or VH domain, i.e., without any linker sequence. The triabody has three Fv heads with the polypeptides arranged in a cyclic, head-to-tail fashion. A possible conformation of the triabody is planar with the three binding sites located in a plane at an angle of 120 degrees from one another. Triabodies can be monospecific, bispecific or trispecific. Thus, antibodies useful in the methods described herein include, but are not limited to, naturally occurring antibodies, bivalent fragments such as (Fab')2, monovalent fragments such as Fab, single chain antibodies, single chain Fv (scFv), single domain antibodies, multivalent single chain antibodies, diabodies, triabodies, and the like that bind specifically with an antigen.

Antibodies can also be raised against a polypeptide or portion of a polypeptide by methods known to those skilled in the art. Antibodies are readily raised in animals such as rabbits or mice by immunization with the gene product, or a fragment thereof. Immunized mice are particularly useful for providing sources of B cells for the manufacture of hybridomas, which in turn are cultured to produce large quantities of monoclonal antibodies. Antibody manufacture methods are described in detail, for example, in Harlow et al., 1988. While both polyclonal and monoclonal antibodies can be used in the methods described herein, it is preferred that a monoclonal antibody is used where conditions require increased specificity for a particular protein.

DETAILED DESCRIPTION

Unless otherwise explained, all technical and scientific terms used herein have the same meaning as commonly understood by one of ordinary skill in the art to which this disclosure belongs. Definitions of common terms in molecular biology may be found in Benjamin Lewin, Genes IX, published by Jones & Bartlett Publishing, 2007 (ISBN-13: 9780763740634); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8). Further, unless otherwise required by context, singular terms shall include pluralities and plural terms shall include the singular.

Unless otherwise stated, the present invention was performed using standard procedures known to one skilled in the art, for example, in Maniatis et al., Molecular Cloning: A Laboratory Manual, Cold Spring Harbor Laboratory Press, Cold Spring Harbor, N.Y., USA (1982); Sambrook et al., Molecular Cloning: A Laboratory Manual (2 ed.), Cold Spring Harbor Laboratory Press, Cold Spring Harbor, N.Y., USA (1989); Davis et al., Basic Methods in Molecular Biology, Elsevier Science Publishing, Inc., New York, USA (1986); Current Protocols in Molecular Biology (CPMB) (Fred M. Ausubel, et al. ed., John Wiley and Sons, Inc.), Current Protocols in Immunology (CPI) (John E. Coligan, et. al., ed. John Wiley and Sons, Inc.), Current Protocols in Cell Biology (CPCB) (Juan S. Bonifacino et. al. ed., John Wiley and Sons, Inc.), Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998), Methods in Molecular biology, Vol. 180, Transgenesis Techniques by Alan R. Clark editor, second edition, 2002, Humana Press, and Methods in Meolcular Biology, Vo. 203, 2003, Transgenic Mouse, edited by Marten H. Hofker and Jan van Deursen, which are all herein incorporated by reference in their entireties.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

Other than in the operating examples, or where otherwise indicated, all numbers expressing quantities of ingredients or reaction conditions used herein should be understood as modified in all instances by the term "about." The term "about" when used in connection with percentages will mean±1%.

All patents and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The present disclosure relates to methods of inhibiting the expression and/or activity of PARP9 and/or PARP14 for inhibiting macrophage and monocytes activation and uses thereof for the purpose for suppressing inflammation.

Embodiments of the present disclosure are based on the identification of a group of proteins that regulate macrophage activation. The poly (ADP-ribose) polymerase family, member 9 (PARP9) promotes expression of genes typical of M1 macrophage polarization while poly (ADP-ribose) polymerase family, member 14 (PAPP14) exerts opposing effects. Silencing of the PARP14 gene induced pro-inflammatory M1 genes (TNF-α, IL-1β and iNOS), while decrease anti-inflammatory M2 markers (Arg1 and MRC1), indicating that PARP14 suppresses M1 pro-inflammatory macrophage activation and promotes anti-inflammatory M2 polarization. In contrast, siRNA silencing experiments demonstrated that PARP9 promotes M1 activation. This is the first report demonstrating that PARP9 and PARP14 are key regulators of macrophage polarization which closely associated with pathological macrophage activation in metabolic disorders, atherosclerotic vascular diseases, autoimmune diseases and cancer. Therefore, PARP9 and PARP14 are modulators of non-activated, non-polarized macrophages and their precursors, monocytes.

Inflammation is part of the complex biological response of vascular tissues to harmful stimuli, such as pathogens, damaged cells, or irritants. The classical signs of acute inflammation are pain, heat, redness, swelling, and loss of function. Inflammation is a protective attempt by the organism to remove the injurious stimuli and to initiate the healing process. Inflammation is not a synonym for infection, even in cases where inflammation is caused by infection. Although infection is caused by a microorganism, inflammation is one of the responses of the organism to the pathogen. However, inflammation is a stereotyped response, and therefore it is considered as a mechanism of innate immunity, as compared to adaptive immunity, which is specific for each pathogen.

Inflammation can be classified as either acute or chronic. Acute inflammation is the initial response of the body to harmful stimuli and is achieved by the increased movement of plasma and leukocytes (especially granulocytes) from the blood into the injured tissues. A cascade of biochemical events propagates and matures the inflammatory response, involving the local vascular system, the immune system, and various cells within the injured tissue. The inflammatory response involved a certain amount of tissue destruction around the harmful stimuli in order to remove the injurious stimuli and to initiate the healing process. However, progressive destruction of the tissue would compromise the survival of the organism. Chronic inflammation can also lead to a host of diseases, such as hay fever, periodontitis, atherosclerosis, rheumatoid arthritis, and even cancer (e.g., gallbladder carcinoma). It is for that reason that inflammation is normally closely regulated by the body.

Prolonged inflammation, also known as chronic inflammation, leads to a progressive shift in the type of cells present at the site of inflammation and is characterized by simultaneous destruction and healing of the tissue from the inflammatory process. Chronic inflammation can lead to excessive and an unacceptable level of tissue damage as a result of the response and is not related to protection against an acute infection or injury. Often times, these remodeling of tissues are undesirable because they interfere with the normal physiological function of the organism and lead to disorders such as atherosclerosis and rheumatoid arthritis.

It is known that macrophage activation contributes to the development of atherosclerosis, metabolic disorders and other critical diseases that involve inflammation. A microenvironment dominant in pro-inflammatory (M1) and lacking anti-inflammatory (M2) macrophages leads to excessive inflammation which mediates the disease condition. Therefore, suppression of the pathological activation of macrophages by modulating PARP9 and/or PARP14 can serve as an attractive therapeutic option of a wide variety of diseases where undesirable chronic inflammation is implicated. For example, inhibiting undesirable excessive or sustained inflammation found in humans, for the treatment, prevention and/or management of conditions where undesirable excessive or sustained inflammation is known or likely to contribute to the onset, development and/or progression the conditions.

Accordingly, in one embodiment, provided herein is a method of inhibiting pro-inflammatory macrophage activation, such as M1, comprising contacting a population of monocytes or macrophages with an effective amount of a composition comprising an inhibitor of PARP9 and/or an activator of PARP14.

In one embodiment, provided herein is a method of inhibiting macrophage M1 activation comprising contacting a population of monocytes or macrophages with an effective amount of a composition comprising an inhibitor of PARP9 and/or an activator of PARP14. It has been shown that PARP9 promotes M1 activation and PARP14 suppresses M1 pro-inflammatory macrophage activation and promotes anti-inflammatory M2 polarization. By inhibiting PARP9 in non-activated macrophages and their precursor, monocytes, it is possible to inhibit the contacted cells from activation. Or by inhibiting PARP9 in activated monocytes or macrophages, it is possible to reduce their pro-inflammatory properties. Similarly, by activating or promoting PARP14 in non-activated macrophages and their precursor, monocytes, it is possible to suppress M1 pro-inflammatory macrophage activation and promote anti-inflammatory M2 polarization in these cells. Or by activating PARP14 in activated monocytes or macrophages, it is possible to reduce their pro-inflammatory properties. Furthermore, the combination of inhibiting PARP9 and activating or promoting PARP14 in non-activated or activated macrophages and their precursor, monocytes, can also suppress M1 pro-inflammatory macrophage activation and/or promote anti-inflammatory M2 polarization in these cells.

In one embodiment, also provided herein is a method of inhibiting macrophage M1 activation comprising contacting a population of monocytes or macrophages with an effective amount of a composition comprising an inhibitor of PARP9.

In one embodiment, also provided herein is a method of inhibiting pro-inflammatory macrophage activation, such as M1, comprising contacting a population of monocytes or macrophages with an effective amount of a composition comprising an inhibitor of PARP9.

In one embodiment, provided herein is a method of inhibiting macrophage M1 activation comprising contacting a population of monocytes or macrophages with an effective amount of a composition comprising an activator of PARP14.

In one embodiment, provided herein is a method of inhibiting pro-inflammatory macrophage activation, such as M1, comprising contacting a population of monocytes or macrophages with an effective amount of a composition comprising an activator of PARP14.

In one embodiment, provided herein is a method of inhibiting macrophageM1 activation comprising contacting a population of monocytes or macrophages with an effective amount of a composition comprising an inhibitor of PARP9 and an activator of PARP14.

In one embodiment, provided herein is a method of inhibiting pro-inflammatory macrophage activation, such as M1, comprising contacting a population of monocytes or macrophages with an effective amount of a composition comprising an inhibitor of PARP9 and an activator of PARP14.

In one embodiment, provided herein is a method of inhibiting macrophage M1 activation comprising the steps of (a) providing a population of monocytes or macrophages or a mixture of both cell types; and (b) contacting the population of monocytes and/or macrophages with an effective amount of a composition comprising an inhibitor of PARP9 and/or an activator of PARP14.

In one embodiment, provided herein is a method of inhibiting pro-inflammatory macrophage activation, such as M1, comprising the steps of (a) providing a population of monocytes or macrophages or a mixture of both cell types; and (b) contacting the population of monocytes and/or macrophages with an effective amount of a composition comprising an inhibitor of PARP9 and/or an activator of PARP14.

Despite the critical impact of macrophage activation on various diseases, its underlying mechanisms remain unclear. Inflammatory diseases such as atherosclerosis may flourish in a microenvironment with dominance of classically activated (M1) macrophages, while alternatively activated M2 macrophages may promote an anti-inflammatory milieu. Whole proteome screening of human and mouse macrophage cell lines stimulated with IFNγ (M1) or IL-4 (M2) identified two adenosine diphosphate (ADP)-ribosylation enzymes—PARP9/ARTD9 and PARP14/ARTD8—as candidates for macrophage activation key regulators. Interactome analysis closely linked PARP9 and PARP14 with coronary artery disease. PARP14 silencing promoted the M1 but suppressed the M2 slant in human and mouse macrophage cell lines and in primary macrophages, apparently via modulating STAT1 and STAT6 pathways. PARP9 silencing suppressed STAT1 phosphorylation and the M1 polarization, however. Co-immunoprecipitation indicated that PARP14 and PARP9 may physically interact with each other. ADP-ribosylation assays indicated that PARP9 may impair PARP14-induced ribosylation. Mass spectrometry demonstrated that PARP14 can ADP-ribosylate at least two sites in STAT1?, which PARP9 suppressed. In vivo, mechanically injured arteries of PARP14–/– mice accelerated lesion formation, macrophage accumulation, and expression of M1-asssocted genes. More macrophages displayed PARP9 immunoreactivity in human plaques with "unstable" than "stable" morphologic characteristics. These findings indicate that PARP14 and PARP9 reciprocally regulate the mechanisms of macrophage activation, offering the potential for new cardiovascular disease therapies and treatments for disorders in which macrophage activity impacts outcomes.

There is a desire to treat and/or prevent and/or management of conditions where undesirable excessive or sustained inflammation is known or implicated to contribute to the onset, development and/or progression the conditions found in humans. Non-exhaustive examples of such conditions include but are not limited to atherosclerosis, obesity, type 2 diabetes, vasculitis, limb ischemia, vein graft disease, AV fistula and/or graft failure, fatty liver disease, brain damage after stroke, brain traumatic injury, cardiac remodeling after acute myocardial infarction, cardiac valve disease, tissue engineered organs, transplanted organs, cancers, Gaucher's disease, autoimmune or autoinflammatory disease, and inflammatory bowel disease.

Accordingly, in one embodiment, provided herein is a method of treating and/or preventing and/or management atherosclerosis and/or a vascular disease in a subject in need thereof comprising contacting a population of monocytes and/or macrophages from the subject with an effective amount of a composition comprising of an inhibitor of PARP9 and/or an activator of PARP14.

In one embodiment, also provided herein is a method of treating and/or preventing and/or management atherosclerosis and/or a vascular disease in a subject in need thereof comprising contacting a population of monocytes or macrophages from the subject with an effective amount of a composition comprising an inhibitor of PARP9.

In one embodiment, provided herein is a method of treating and/or preventing and/or management atherosclerosis and/or a vascular disease in a subject in need thereof comprising contacting a population of monocytes or macrophages from the subject with an effective amount of a composition comprising an activator of PARP14.

In one embodiment, provided herein is a method of treating and/or preventing and/or management atherosclerosis and/or a vascular disease in a subject in need thereof comprising contacting a population of monocytes or macrophages from the subject with an effective amount of a composition comprising an inhibitor of PARP9 and an activator of PARP14.

In one embodiment, provided herein is a method of treating and/or preventing and/or management atherosclerosis and/or a vascular disease in a subject in need thereof comprising the steps of (a) providing a population of monocytes or macrophages or a mixture of both cell types from the subject; and (b) contacting the population of monocytes and/or macrophages from the subject with an effective amount of a composition comprising an inhibitor of PARP9 and/or an activator of PARP14.

In one embodiment, provided herein is a method of inhibiting excessive or sustained inflammation in a subject in need thereof comprising contacting a population of monocytes and/or macrophages from the subject with an effective amount of a composition comprising an inhibitor of PARP9 and/or an activator ofPARP14.

In one embodiment, provided herein is a method of inhibiting excessive or sustained inflammation in a subject in need thereof comprising administering to the subject an effective amount of a pharmaceutical composition comprising of an inhibitor of PARP9 and/or an activator of PARP14 and a pharmaceutically acceptable carrier or diluent.

In one embodiment, provided herein is a method of treating or preventing atherosclerosis and/or a vascular disease in a subject in need thereof comprising the step of (a) identifying a subject who has or is at risk of atherosclerosis; and (b) administering to the subject an effective amount of a pharmaceutical composition comprising of an inhibitor of PARP9 and/or an activator of PARP14 and a pharmaceutically acceptable carrier or diluent.

The inventors have explored key regulators of macrophage polarization for modulating pathological activation of macrophages as novel therapeutic targets of various of inflammatory diseases. The tandem mass tagging strategy (TMT) was used to quantify the changes in the proteomes of mouse and human macrophage cell lines, RAW264.7 and THP-1 respectively, in response to either interferon gamma (IFNγ) as an M1 stimulator or interleukin 4 (IL-4) as an M1 inducer. 5816 proteins from mouse and 4723 in human cell line were quantified. By cluster analysis of these data, poly(ADP-ribose) polymerase 9 (PARP9), PARP14 and DTX3L were identified as candidates of master regulators of macrophage polarization. Network analysis closely linked the PARP9-PARP14 network with the coronary artery disease gene module. Silencing of PARP14 gene induced pro-inflammatory M1 genes (TNF-α, IL-1β and iNOS), while decrease anti-inflammatory M2 markers (Arg1 and MRC1), indicating that PARP14 suppresses M1 pro-inflammatory macrophage activation and promotes anti-inflammatory M2 polarization with inducing phosphorylation of STAT1 and reducing STAT6 phosphorylation, indicating their roles in the signal tranduction mechanisms. Additionally, in primary macrophages derived from PARP14-deficient mice, M1 genes dramatically increased (more than 40 times), while M2 markers drastically decreased (less than 1/30). In contrast, siRNA silencing experiments demonstrated that PARP9 promotes M1 activation via STAT1 phosphorylation with suppressing STAT6 activation.

In one embodiment of any one method, the inhibition of macrophage M1 activation comprises inhibiting pro-inflammatory M1 polarization in the monocytes and/or macrophages.

In one embodiment of any one method, the inhibition of macrophage activation comprises inhibiting pro-inflammatory polarization, such as M1, in the monocytes and/or macrophages.

In one embodiment of any one method, the inhibition of pro-inflammatory M1 polarization in the monocytes and/or macrophages comprises the suppression of a pro-inflammatory M1 gene.

In one embodiment of any one method, the inhibition of pro-inflammatory polarization in the monocytes and/or macrophages comprises the suppression of a pro-inflammatory M1 gene.

In one embodiment of any one method, the inhibition of excessive or sustained inflammation in the subject comprises inhibiting pro-inflammatory M1 polarization in the monocytes and/or macrophages in the subject. The objective is to suppress monocytes and/or macrophages M1 polarization. At the same time, or separately, to promote monocytes and/or macrophages M2 polarization. With this strategy, the microenvironment that typical in chronic inflammation where there is dominant in pro-inflammatory M1 macrophages and lacking anti-inflammatory M2 macrophages, can be shifted to a microenvironment that is quite opposite, a microenvironment where there is dominant anti-inflammatory M2 macrophages and relatively lacking in pro-inflammatory M1 macrophages.

In one embodiment of any one method, the inhibition of excessive or sustained inflammation in the subject comprises inhibiting pro-inflammatory macrophage polarization, such as M1, in the monocytes and/or macrophages in the subject. The objective is to suppress monocytes and/or macrophages polarization (e.g., M1). At the same time, or separately, to promote none/anti-inflammatory polarization of monocytes and/or macrophages (e.g., M2). With this strategy, the microenvironment that typical in chronic inflammation where there is dominant in pro-inflammatory macrophages and the paucity of anti-inflammatory macrophages, can be shifted to a microenvironment that is quite opposite, a microenvironment where there is dominant anti-inflammatory macrophages and relatively lacking in pro-inflammatory macrophages.

In one embodiment of any one method, the inhibition of macrophage M1 activation comprises increasing the expression of an anti-inflammatory M2 marker in the monocytes and/or macrophages.

In one embodiment of any one method, the inhibition of pro-inflammatory macrophage activation (e.g., M1) comprises increasing the expression of a marker of an anti-inflammatory polarization (e.g., M2) in the monocytes and/or macrophages.

In one embodiment of any one method where the pro-inflammatory M1 polarization of contacted monocytes and/or macrophages is inhibited in the subject, the expression of inflammatory factors (IL-1γ, TNFα, IL-6) are decreased, relative to expression prior to such contacting.

In one embodiment of any one method where the pro-inflammatory polarization of contacted monocytes and/or macrophages is inhibited in the subject, the expression of inflammatory factors typical of M1 macrophages (IL-1γ, TNFα, IL-6) are decreased, relative to expression prior to such contacting.

In one embodiment of any one method, whereby an anti-inflammatory M2 marker expression in monocytes and/or macrophages in the subject is increased.

In one embodiment of any one method, whereby an anti-inflammatory macrophage marker expression in monocytes and/or macrophages in the subject is increased.

In one embodiment of any one method, the pro-inflammatory M1 gene suppressed is selected from the group consisting of but not limited to tumor necrosis factor alpha (TNF-α), interleukin 1β (IL-1β), IL-6, and inducible nitric oxide synthase (iNOS).

In one embodiment of any one method, the pro-inflammatory gene suppressed is selected from the group consisting of but not limited to tumor necrosis factor alpha (TNF-α), interleukin 1β (IL-1β), IL-6, and inducible nitric oxide synthase (iNOS).

In one embodiment of any one method, the inhibition of macrophage M1 activation comprises increasing the expression of an anti-inflammatory M2 marker.

In one embodiment of any one method, the inhibition of macrophage pro-inflammatory activation (e.g., M1) comprises increasing the expression of a marker of an anti-inflammatory macrophages (e.g., M2).

In one embodiment of any one method, the anti-inflammatory M2 markers include but are not limited to arginase 1 (Arg1) or mannose receptor, C type 1 (MRC1).

In one embodiment of any one method, the population of monocytes or macrophage is contacted with the PARP9 inhibitor and/or the PARP14 activator ex vivo or in vitro or in vivo.

In one embodiment, the monocytes or non-activated macrophages are contacted ex vivo or in vitro. In a specific embodiment, the cell being contacted is a cell of the myeloid lineage. Cells of the myeloid lineage give rise to monocytes which in turn give rise to macrophages. In one embodiment, the composition inhibits PARP9 expression.

In some embodiment, the monocyte or non-activated macrophage has at least one of the following cell surface markers characteristics of cell derived from the myeloid lineage: CD68, F4/80 (EMR1) and CD11b.

In one embodiment of any one method, the atherosclerosis is chronic, meaning the atherosclerosis has been occurring for at least the past 3 months.

In one embodiment of any one method, the vascular disease is acute or chronic.

Vascular disease includes any condition that affects your circulatory system, such as coronary or peripheral artery disease. This ranges from diseases of your arteries, veins and lymph vessels to blood disorders that affect circulation.

In one embodiment of any one method, the vascular disease includes but is not limited to coronary artery atherosclerosis, carotid artery atherosclerosis, peripheral artery (or arterial) disease, in-stent restenosis, renal artery disease, diabetic vasculopathy, vasculitis (e.g., Behçet's disease, giant cell arteritis, Takayasu's arteritis, Buerger's disease, Kawasaki disease), aortic aneurysms, cerebrovascular disease, transplant arteriopathy, narrowing or occlusion of vein grafts for peripheral artery (or arterial) disease, narrowing or occlusion of vein grafts for coronary arteries, narrowing or occlusion of AV fistulas/grafts, narrowing or occlusion of tissue-engineered vessels. In some embodiments of any one method described here, the vascular disease includes its complications such as ventricular remodeling after acute myocardial infarction (AMI), and brain damage after stroke.

In one embodiment of any one method, the composition comprises a lipid encapsulation formulation of the inhibitor of PARP9 and/or the activator of PARP14. In one embodiment of any one method, the lipid encapsulation formulation is formulated such that the inhibitor of PARP9 and/or the activator of PARP14 are target to primarily monocytes and non-activated macrophages.

Accordingly, in one embodiment of any one method, the lipid encapsulates the inhibitor of PARP9 and/or the activator of PARP14 for delivery into to monocytes and macrophages. In one embodiment, the inhibitor of PARP9 and/or the activator of PARP14 described herein are condensed with a cationic polymer, e.g., PEI, polyamine spermidine, and spermine, or a cationic peptide, e.g., protamine and poly-lysine, and encapsulated in the lipid particle. The liposomes can comprise multiple layers assembled in a step-wise fashion.

Lipid materials well known and routinely utilized in the art to produce liposomes. Lipids may include relatively rigid varieties, such as sphingomyelin, or fluid types, such as phospholipids having unsaturated acyl chains. "Phospholipid" refers to any one phospholipid or combination of phospholipids capable of forming liposomes. Phosphatidylcholines (PC), including those obtained from egg, soy beans or other plant sources or those that are partially or wholly synthetic, or of variable lipid chain length and unsaturation are suitable for use in the present invention. Synthetic, semisynthetic and natural product phosphatidylcholines including, but not limited to, distearoylphosphatidylcholine (DSPC), hydrogenated soy phosphatidylcholine (HSPC), soy phosphatidylcholine (soy PC), egg phosphatidylcholine (egg PC), hydrogenated egg phosphatidylcholine (HEPC), dipalmitoylphosphatidylcholine (DPPC) and dimyristoylphosphatidylcholine (DMPC) are suitable phosphatidylcholines for use in this invention. All of these phospholipids are commercially available. Further, phosphatidylglycerols (PG) and phosphatic acid (PA) are also suitable phospholipids for use in the present invention and include, but are not limited to, dimyristoylphosphatidylglycerol (DMPG), dilaurylphosphatidylglycerol (DLPG), dipalmitoylphosphatidylglycerol (DPPG), distearoylphosphatidylglycerol (DSPG) dimyristoylphosphatidic acid (DMPA), distearoylphosphatidic acid (DSPA), dilaurylphosphatidic acid (DLPA), and dipalmitoylphosphatidic acid (DPPA). Distearoylphosphatidylglycerol (DSPG) is a negatively-charged lipid often used in formulations.

Other suitable phospholipids include phosphatidylethanolamines, phosphatidylinositols, sphingomyelins, and phosphatidic acids containing lauric, myristic, stearoyl, and palmitic acid chains. For the purpose of stabilizing the lipid membrane, one may add an additional lipid component, such as cholesterol. Lipids for producing liposomes according to the invention may include phosphatidylethanolamine (PE) and phosphatidylcholine (PC) in further combination with cholesterol (CH). For example, a combination of lipids and cholesterol for producing the liposomes of the invention comprise a PE:PC:Chol molar ratio of 3:1:1. Further, incorporation of polyethylene glycol (PEG) containing phospholipids is also contemplated by the present invention.

In addition, in order to prevent the uptake of the liposomes into the cellular endothelial systems and enhance the uptake of the liposomes into the tissue of interest, the outer surface of the liposomes may be modified with a long-circulating agent. The modification of the liposomes with a hydrophilic polymer as the long-circulating agent is known to enable to prolong the half-life of the liposomes in the blood Liposomes encapsulating the nucleic acid segments described herein can be obtained by any method known to the skilled artisan. For example, the liposome preparation of the present invention can be produced by reverse phase evaporation (REV) method (see U.S. Pat. No. 4,235,871), infusion procedures, or detergent dilution. A review of these and other methods for producing liposomes may be found in 1 LIPOSOMES, (Marc Ostro, ed., Marcel Dekker, Inc., NY, 1983). See also Szoka et al., 9 Ann. Rev. Biophys. Bioeng. 467 (1980).

In one embodiment of any one method, the lipid encapsulation formulation comprises lipid particles that are liposomes. In one embodiment of any one method, the lipid encapsulation formulation comprises lipid particles that are micelles.

In one embodiment of any one method, the inhibitor of PARP9 inhibits the expression of PARP9.

In one embodiment of any one method, the inhibitor of PARP9 is a small molecule or a nucleic acid.

In one embodiment of any one method, the nucleic acid is a PARP9-specific RNA interference agent, or a vector encoding a PARP9 specific RNA interference agent or an aptamer that binds PARP9.

In one embodiment of any one method, the PARP9-specific RNA interference agent is a single stranded (ssRNA), a double stranded RNA (dsRNA) or a short hairpin RNA (shRNA).

In one embodiment of any one method, the RNA interference agent hybridizes to a PARP9 nucleic acid sequence.

In one embodiment of any one method, the RNA interference agent comprises a nucleic sequence derived from the human PARP9 gene having a GENBANK™ Accession number BC039580.

In one embodiment of any one method, the PARP9-specific RNA interference agent comprises one or more of the nucleotide sequences selected from a group consisting of SEQ ID NOS: 1-28, 33-36, and 41-44.

In one embodiment of any one method, the PARP9-specific RNA interference agent nucleotide sequences include but are not limited to GATTTAACTTGTTCTGTAA (SEQ ID NO:1), TTGAAGATATGCTTTGTAA (SEQ ID NO:2), GCCATAGGCTGTTTCAGCA (SEQ ID NO:3), GTCTCCATCACAGAAATTA (SEQ ID NO:4), TGGTGATTTGAAATCCAA (SEQ ID NO:5), GAGTTGAAATGAAATCGGA (SEQ ID NO:6), CTTTAAAGCTGCTTCAGAA (SEQ ID NO:7), ATGACAGTGTGGTTGACAA (SEQ ID NO:8), CAAACAGTTTGTTGCCAGA (SEQ ID NO:9), TCCTGTGCCTCCAACTCAA (SEQ ID NO:10), GACTGGTGCTCTTGGAGAA (SEQ ID NO:11), GGAAGCCAATGATGAGTAA (SEQ ID NO:12), TTCAGAATTTCCTAAACCT (SEQ ID NO:13), CTGGAAACATGGAAATAAA (SEQ ID NO:14), CTCTGAATTTGTGTACAAA (SEQ ID NO:15), CCATCAATCTGATGGGATT (SEQ ID NO:16), CAGATAAGCTGATCTATGT (SEQ ID NO:17), GGGTTAGTTTGCAAGGGAA (SEQ ID NO:18), CAGATTTGGAGATATATAA (SEQ ID NO:19), TGCTGAGTTTGAACAATTA (SEQ ID NO:20), CCATTAACCACAATGACTT (SEQ ID NO:21), GCAGACGGCAGATGTAATT (SEQ ID NO:22), CCCACATGATATTACAGTT (SEQ ID NO:23), GCAGGAGTTGAAATGAAAT (SEQ ID NO:24), GCCATCAATCTGATGGGAT (SEQ ID NO:25), GCTGGTATGGCCTTACCTT (SEQ ID NO:26), CCTCTTGCAGTTGTTCTTT (SEQ ID NO:27), CCTTTACTAGAGGAGATAA (SEQ ID NO:28), AAUUACAUCUGCCGUCUGC (SEQ ID NO: 33), UUUGUGGCAAGAAAUUCCG (SEQ ID NO: 34), UUAAUCAACAGGGCUGCCA (SEQ ID NO: 35), UACAGCCAAACUUAUUCUG (SEQ ID NO: 36), ACACAAUGUCUUCGAAAUU (SEQ ID NO: 41), CCAGACAGCUAUCGAAUUA (SEQ ID NO: 42), CCAAAUAUGAUCUACGCAU (SEQ ID NO: 43), and CGUACACAUUUCAACGAUA (SEQ ID NO: 44).

In one embodiment of any one method, the inhibitor of PARP9 inhibits PARP9 protein's activity. In some embodiments, the inhibitor of PARP9 interferes or inhibits the regulation of transcription by PARP9. In some embodiments, the inhibitor of PARP9 interferes or inhibits with the catalyzes the post-translational modification of proteins by the addition of multiple ADP-ribose moieties by PARP9, and/or interferes or inhibits directly or indirectly with the induction of the expression of IFN-gamma-responsive genes.

In one embodiment of any one method, the inhibitor of PARP9 is selected from the group consisting of an antibody against PARP9 or an antigen-binding fragment thereof, a small molecule, and a nucleic acid.

In one embodiment of any one method, the activator of PARP14 increases the expression of PARP14 and/or PARP14 protein's activity.

In one embodiment of any one method, the activator of PARP14 is selected from the group consisting of an antibody against PARP9 or an antigen-binding fragment thereof, a small molecule, and a nucleic acid.

In one embodiment of any one method, the composition comprising the inhibitor of PARP9 and/or the activator of PARP14 further comprises a pharmaceutically acceptable carrier or diluent.

In one embodiment of any one method, the composition is administered by injection, infusion, or instillation.

In one embodiment of any one method, the pharmaceutical composition is administered by injection, infusion, or instillation.

In one embodiment of any one method, the pharmaceutical composition comprises a formulation comprising lipid encapsulation of the inhibitor of PARP9 and/or an activator of PARP14 and a pharmaceutically acceptable carrier or diluent.

In one embodiment of any one method, the excessive or sustained inflammation is found in a condition including but is not limited to atherosclerosis, obesity, type 2 diabetes, vasculitis, limb ischemia, vein graft disease, AV fistulas and/or grafts, fatty liver disease, brain damage after stroke, brain traumatic injury, cardiac remodeling after acute myocardial infarction, cardiac valves, tissue engineered organs, transplanted organs, cancers, Gaucher's disease, autoimmune or autoinflammatory disease, and inflammatory bowel disease.

In one embodiment of any one method, the autoimmune or autoinflammatory disease is selected from the group consisting of rheumatoid arthritis, lupus erythematosus, and Behçet's disease.

In one embodiment of any of the methods, the method further comprises selecting a subject who has atherosclerosis or is at risk of developing atherosclerosis. The risk factors for developing atherosclerosis are well known in the art. Exemplary risk factors are diabetes, dyslipidemia (high LDL, low HDL), hypertension, smoking habit, obesity, and male gender. A physician can readily assess a subject's risk and determine whether to prevent atherosclerosis from eventually developing in the subject.

In one embodiment of any one method, further comprising selecting a subject having excessive or sustained inflammation. Such a subject would be one who has been diagnosed with any medical conditions where chronic inflammation has been implicated. For example, medical conditions such as but not limited to atherosclerosis, obesity, type 2 diabetes, vasculitis, limb ischemia, vein graft disease, AV fistulas and/or grafts, fatty liver disease, brain damage after stroke, brain traumatic injury, cardiac remodeling after acute myocardial infarction, cardiac valve diseases, tissue engineered organs, transplanted organs, cancers, Gaucher's disease, autoimmune or autoinflammatory disease, and inflammatory bowel disease. A skilled clinician would be able to diagnosed the medical condition and selecting a subject for the treatment method when the subject has a medical condition where inflammation has been implicated.

In one embodiment of any one method, further comprises selecting a subject at risk of developing excessive or sustained inflammation that could lead to any medical conditions where excessive or sustained inflammation has been implicated. The risk factors for developing medical conditions where excessive or sustained inflammation has been implicated are well known in the art. For example, excess body weight gain for obesity, type 2 diabetes, vasculitis, limb ischemia; and acute myocardial infarction for cardiac remodeling; and high blood LDL or TG or low HDL for atherosclerosis. A skilled clinician would be able to assess the presence of relevant risk factors in a subject and select the subject for the treatment or preventative method when the subject has at least one risk factor of developing excessive or sustained inflammation that could lead to any or a medical condition where chronic inflammation has been implicated.

In one embodiment of any one method, further comprising selecting a subject for administration of the pharmaceutical composition.

It is also contemplated that the methods described herein can be used as prophylaxis.

Inhibitors of PARP9

In one embodiment of any one method, the inhibitor of PARP9 is selected from the group consisting of an antibody against PARP9 or an antigen-binding fragment thereof, a small molecule, and a nucleic acid.

In one embodiment of any one method, the inhibitor of PARP9 includes but is not limited to DR 2313, 3-aminobenzamide, 4-HQN, NU 1025, PJ 34 hydrochloride, and 3-Carbamoyl-1-D-ribofuranosylpyridinium hydroxide 5'-ester with adenosine 5'-pyrophosphate and derivatives.

Antibodies that specifically bind PARP9 can be used for the inhibition of PARP9 in vivo or ex vivo or in vitro. Antibodies to PARP9 are commercially available and can be raised by one of skill in the art using well known methods. The PARP9 inhibitory activity of a given antibody, or, for that matter, any PARP9 inhibitor, can be assessed using methods known in the art or described herein. To avoid doubt, an antibody that inhibits PARP9 will bind to PARP9 and interferes or inhibits with the regulation of transcription by PARP9, and/or interferes or inhibits with catalyzes the post-translational modification of proteins by the addition of multiple ADP-ribose moieties by PARP9, and/or interferes or inhibits directly or indirectly with the induction of the expression of IFN-gamma-responsive genes.

Antibody inhibitors of PARP9 can include polyclonal and monoclonal antibodies and antigen-binding derivatives or fragments thereof. Well known antigen binding fragments include, for example, single domain antibodies (dAbs; which consist essentially of single VL or VH antibody domains), Fv fragment, including single chain Fv fragment (scFv), Fab fragment, and F(ab')2 fragment. Methods for the construction of such antibody molecules are well known in the art.

Nucleic Acid Inhibitors of PARP9 Expression.

A powerful approach for inhibiting the expression of selected target polypeptides is through the use of RNA interference agents. RNA interference (RNAi) uses small interfering RNA (siRNA) duplexes that target the messenger RNA encoding the target polypeptide for selective degradation. siRNA-dependent post-transcriptional silencing of gene expression involves cleaving the target messenger RNA molecule at a site guided by the siRNA. "RNA interference (RNAi)" is an evolutionarily conserved process whereby the expression or introduction of RNA of a sequence that is identical or highly similar to a target gene results in the sequence specific degradation or specific post-transcriptional gene silencing (PTGS) of messenger RNA (mRNA) transcribed from that targeted gene (see Coburn, G. and Cullen, B. (2002) J. of Virology 76(18): 9225), thereby inhibiting expression of the target gene. In one embodiment, the RNA is double stranded RNA (dsRNA). This process has been described in plants, invertebrates, and mammalian cells. In nature, RNAi is initiated by the dsRNA-specific endonuclease Dicer, which promotes processive cleavage of long dsRNA into double-stranded fragments termed siRNAs. siRNAs are incorporated into a protein complex (termed "RNA induced silencing complex," or "RISC") that recognizes and cleaves target mRNAs. RNAi can also be initiated by introducing nucleic acid molecules, e.g., synthetic siRNAs or RNA interfering agents, to inhibit or silence the expression of target genes. As used herein, "inhibition of target gene expression" includes any decrease in expression or protein activity or level of the target gene or protein encoded by the target gene as compared to a situation wherein no RNA interference has been induced. The decrease will be of at least 10%, 20%, 30%, 40%, 50%, 60%, 70%, 80%, 90%, 95% or 99% or more as compared to the expression of a target gene or the activity or level of the protein encoded by a target gene which has not been targeted by an RNA interfering agent.

The terms "RNA interference agent" and "RNA interference" as they are used herein are intended to encompass those forms of gene silencing mediated by double-stranded RNA, regardless of whether the RNA interfering agent comprises an siRNA, miRNA, shRNA or other double-stranded RNA molecule. "Short interfering RNA" (siRNA), also referred to herein as "small interfering RNA" is defined as an RNA agent which functions to inhibit expression of a target gene, e.g., by RNAi. An siRNA may be chemically synthesized, may be produced by in vitro transcription, or may be produced within a host cell. In one embodiment, siRNA is a double stranded RNA (dsRNA) molecule of about 15 to about 40 nucleotides in length, preferably about 15 to about 28 nucleotides, more preferably about 19 to about 25 nucleotides in length, and more preferably about 19, 20, 21, 22, or 23 nucleotides in length, and may contain a 3' and/or 5' overhang on each strand having a length of about 0, 1, 2, 3, 4, or 5 nucleotides. The length of the overhang is independent between the two strands, i.e., the length of the overhang on one strand is not dependent on the length of the overhang on the second strand. Preferably the siRNA is capable of promoting RNA interference through degradation or specific post-transcriptional gene silencing (PTGS) of the target messenger RNA (mRNA).

siRNAs also include small hairpin (also called stem loop) RNAs (shRNAs). In one embodiment, these shRNAs are composed of a short (e.g., about 19 to about 25 nucleotide) antisense strand, followed by a nucleotide loop of about 5 to about 9 nucleotides, and the analogous sense strand. Alternatively, the sense strand may precede the nucleotide loop structure and the antisense strand may follow. These shRNAs may be contained in plasmids, retroviruses, and lentiviruses and expressed from, for example, the pol III U6 promoter, or another promoter (see, e.g., Stewart, et al. (2003) RNA April; 9(4):493-501, incorporated by reference herein in its entirety). The target gene or sequence of the RNA interfering agent may be a cellular gene or genomic sequence, e.g. the PARP9 sequence. An siRNA may be substantially homologous to the target gene or genomic sequence, or a fragment thereof. As used in this context, the term "homologous" is defined as being substantially identical, sufficiently complementary, or similar to the target mRNA, or a fragment thereof, to effect RNA interference of the target. In addition to native RNA molecules, RNA suitable for inhibiting or interfering with the expression of a target sequence include RNA derivatives and analogs. Preferably, the siRNA is identical to its target. The siRNA preferably targets only one sequence. Each of the RNA interfering agents, such as siRNAs, can be screened for potential off-target effects by, for example, expression profiling. Such methods are known to one skilled in the art and are described, for example, in Jackson et al. Nature Biotechnology 6:635-637, 2003. In addition to expression profiling, one may also screen the potential target sequences for similar sequences in the sequence databases to identify potential sequences which may have off-target effects. For example, according to Jackson et al., 15, or perhaps as few as 11 contiguous nucleotides, of sequence identity are sufficient to direct silencing of non-targeted transcripts. Therefore, one may initially screen the proposed siRNAs to avoid potential off-target silencing using the sequence identity analysis by any known sequence comparison methods, such as BLAST. siRNA sequences are chosen to maximize the uptake of the antisense (guide) strand of the siRNA into RISC and thereby maximize the ability of RISC to target human GGT mRNA for degradation. This can be accomplished by scanning for sequences that have the lowest free energy of binding at the 5'-terminus of the antisense strand. The lower free energy leads to an enhancement of the unwinding of the 5'-end of the antisense strand of the siRNA duplex, thereby ensuring that the antisense strand will be taken up by RISC and direct the sequence-specific cleavage of the human PARP9 mRNA. siRNA molecules need not be limited to those molecules containing only RNA, but, for example, further encompasses chemically modified nucleotides and non-nucleotides, and also include molecules wherein a ribose sugar molecule is substituted for another sugar molecule or a molecule which performs a similar function. Moreover, a non-natural linkage between nucleotide residues can be used, such as a phosphorothioate linkage. The RNA strand can be derivatized with a reactive functional group of a reporter group, such as a fluorophore. Particularly useful derivatives are modified at a terminus or termini of an RNA strand, typically the 3' terminus of the sense strand. For example, the 2'-hydroxyl at the 3' terminus can be readily and selectively derivatizes with a variety of groups. Other useful RNA derivatives incorporate nucleotides having modified carbohydrate moieties, such as 2'O-alkylated residues or 2'-O-methyl ribosyl derivatives and 2'-O-fluoro ribosyl derivatives. The RNA bases may also be modified. Any modified base useful for inhibiting or interfering with the expression of a target sequence may be used. For example, halogenated bases, such as 5-bromouracil and 5-iodouracil can be incorporated. The bases may also be alkylated, for example, 7-methylguanosine can be incorporated in place of a guanosine residue. Non-natural bases that yield successful inhibition can also be incorporated. The most preferred siRNA modifications include 2'-deoxy-2'-fluorouridine or locked nucleic acid (LAN) nucleotides and RNA duplexes containing either phosphodiester or varying numbers of phosphorothioate linkages. Such modifications are known to one skilled in the art and are described, for example, in Braasch et al., Biochemistry, 42: 7967-7975, 2003. Most of the useful modifications to the siRNA molecules can be introduced using chemistries established for antisense oligonucleotide technology. Preferably, the modifications involve minimal 2'-O-methyl modification, preferably excluding such modification. Modifications also preferably exclude modifications of the free 5'-hydroxyl groups of the siRNA. The Examples herein provide specific examples of RNA interfering agents, such as shRNA molecules that effectively target PARP9 mRNA.

In one embodiment of any of the method, the RNA interference agent is delivered or administered in a pharmaceutically acceptable carrier. In one embodiment, the RNA interference agent is encapsulated in lipid and formulated for delivery or administration. In one embodiment, lipid encapsulation formulation comprising the RNA interference agent described is delivered or administered in a pharmaceutically acceptable carrier. Additional carrier agents, such as liposomes, can be added to the pharmaceutically acceptable carrier. In another embodiment, the RNA interference agent is delivered by a vector encoding small hairpin RNA (shRNA) in a pharmaceutically acceptable carrier to the cells in an organ of an individual. The shRNA is converted by the cells after transcription into siRNA capable of targeting, for example, PARP9.

In one embodiment of any of the method, the siRNA, ssRNA, dsRNA or shRNA as inhibitors of PARP9 comprises GATTTAACTTGTTCTGTAA (SEQ ID NO:1), TTGAAGATATGCTTTGTAA (SEQ ID NO:2), GCCATAGGCTGTTTCAGCA (SEQ ID NO:3), GTCTCCATCACAGAAATTA (SEQ ID NO:4), TGGTGGATTTGAAATCCAA (SEQ ID NO:5), GAGTTGAAATGAAATCGGA (SEQ ID NO:6), CTTTAAAGCTGCTTCAGAA (SEQ ID NO:7), ATGACAGTGTGGTTGACAA (SEQ ID NO:8), CAAACAGTTTGTTGCCAGA (SEQ ID NO:9), TCCTGTGCCTCCAACTCAA (SEQ ID NO:10), GACTGGTGCTCTTGGAGAA (SEQ ID NO:11), GGAAGCCAATGATGAGTAA (SEQ ID NO:12), TTCAGAATTTCCTAAACCT (SEQ ID NO:13), CTGGAAACATGGAAATAAA (SEQ ID NO:14), CTCTGAATTTGTGTACAAA (SEQ ID NO:15), CCATCAATCTGATGGGATT (SEQ ID NO:16), CAGATAAGCTGATCTATGT (SEQ ID NO:17), GGGTTAGTTTGCAAGGGAA (SEQ ID NO:18), CAGATTTGGAGATATATAA (SEQ ID NO:19), TGCTGAGTTTGAACAATTA (SEQ ID NO:20), CCATTAACCACAATGACTT (SEQ ID NO:21), GCAGACGGCAGATGTAATT (SEQ ID NO:22), CCCACATGATATTACAGTT (SEQ ID NO:23), GCAGGAGTTGAAATGAAAT (SEQ ID NO:24), GCCATCAATCTGATGGGAT (SEQ ID NO:25), GCTGGTATGGCCTTACCTT (SEQ ID NO:26), CCTCTTGCAGTTGTTCTTT (SEQ ID NO:27), CCTTTACTAGAGGAGATAA (SEQ ID NO:28), AAUUACAUCUGCCGUCUGC (SEQ ID NO: 33), UUUGUGGCAAGAAAUUCCG (SEQ ID NO: 34), UUAAUCAACAGGGCUGCCA (SEQ ID NO: 35), UACAGCCAAACUUAUUCUG (SEQ ID NO: 36), ACACAAUGUCUUCGAAAUU (SEQ ID NO: 41), CCAGACAGCUAUCGAAUUA (SEQ ID NO: 42), CCAAAUAUGAUCUACGCAU (SEQ ID NO: 43), and CGUACACAUUUCAACGAUA (SEQ ID NO: 44).

In one embodiment of any of the method, the vector is a regulatable vector, such as tetracycline inducible vector. Methods described, for example, in Wang et al. Proc. Natl. Acad. Sci. 100: 5103-5106, using pTet-On vectors (BD Biosciences Clontech, Palo Alto, Calif.) can be used. In one embodiment, the RNA interference agents used in the methods described herein are taken up actively by cells in vivo following intravenous injection, e.g., hydrodynamic injection, without the use of a vector, illustrating efficient in vivo delivery of the RNA interfering agents. One method to deliver the siRNAs is catheterization of the blood supply vessel of the target organ. Other strategies for delivery of the RNA interference agents, e.g., the siRNAs or shRNAs used in the methods of the invention, may also be employed, such as, for example, delivery by a vector, e.g., a plasmid or viral vector, e.g., a lentiviral vector. Such vectors can be used as described, for example, in Xiao-Feng Qin et al. Proc. Natl. Acad. Sci. U.S.A., 100: 183-188. Other delivery methods include delivery of the RNA interfering agents, e.g., the siRNAs or shRNAs of the invention, using a basic peptide by conjugating or mixing the RNA interfering agent with a basic peptide, e.g., a fragment of a TAT peptide, mixing with cationic lipids or formulating into particles. The RNA interference agents, e.g., the siRNAs targeting PARP9 mRNA, may be delivered singly, or in combination with other RNA interference agents, e.g., siRNAs, such as, for example siRNAs directed to other cellular genes. PARP9 siRNAs may also be administered in combination with other pharmaceutical agents which are used to treat or prevent diseases or disorders associated with oxidative stress, especially respiratory diseases, and more especially asthma. Synthetic siRNA molecules, including shRNA molecules, can be obtained using a number of techniques known to those of skill in the art. For example, the siRNA molecule can be chemically synthesized or recombinantly produced using methods known in the art, such as using appropriately protected ribonucleoside phosphoramidites and a conventional DNA/RNA synthesizer (see, e.g., Elbashir, S. M. et al. (2001) Nature 411:494-498; Elbashir, S. M., W. Lendeckel and T. Tuschl (2001) Genes & Development 15:188-200; Harborth, J. et al. (2001) J. Cell Science 114:4557-4565; Masters, J. R. et al. (2001) Proc. Natl. Acad. Sci., USA 98:8012-8017; and Tuschl, T. et al. (1999) Genes & Development 13:3191-3197). Alternatively, several commercial RNA synthesis suppliers are available including, but not limited to, Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA), and Cruachem (Glasgow, UK). As such, siRNA molecules are not overly difficult to synthesize and are readily provided in a quality suitable for RNAi. In addition, dsRNAs can be expressed as stem loop structures encoded by plasmid vectors, retroviruses and lentiviruses (Paddison, P. J. et al. (2002) Genes Dev. 16:948-958; McManus, M. T. et al. (2002) RNA 8:842-850; Paul, C. P. et al. (2002) Nat. Biotechnol. 20:505-508; Miyagishi, M. et al. (2002) Nat. Biotechnol. 20:497-500; Sui, G. et al. (2002) Proc. Natl. Acad. Sci., USA 99:5515-5520; Brummelkamp, T. et al. (2002) Cancer Cell 2:243; Lee, N. S., et al. (2002) Nat. Biotechnol. 20:500-505; Yu, J. Y., et al. (2002) Proc. Natl. Acad. Sci., USA 99:6047-6052; Zeng, Y., et al. (2002) Mol. Cell 9:1327-1333; Rubinson, D. A., et al. (2003) Nat. Genet. 33:401-406; Stewart, S. A., et al. (2003) RNA 9:493-501). These vectors generally have a polIII promoter upstream of the dsRNA and can express sense and antisense RNA strands separately and/or as a hairpin structures. Within cells, Dicer processes the short hairpin RNA (shRNA) into effective siRNA. The targeted region of the siRNA molecule of the present invention can be selected from a given target gene sequence, e.g., a PARP9 coding sequence, beginning from about 25 to 50 nucleotides, from about 50 to 75 nucleotides, or from about 75 to 100 nucleotides downstream of the start codon. Nucleotide sequences may contain 5' or 3' UTRs and regions nearby the start codon. One method of designing a siRNA molecule of the present invention involves identifying the 23 nucleotide sequence motif AA(N19)TT (SEQ. ID. NO. 63) (where N can be any nucleotide) and selecting hits with at least 25%, 30%, 35%, 40%, 45%, 50%, 55%, 60%, 65%, 70% or 75% G/C content. The "TT" portion of the sequence is optional. Alternatively, if no such sequence is found, the search may be extended using the motif NA(N21), where N can be any nucleotide. In this situation, the 3' end of the sense siRNA may be converted to TT to allow for the generation of a symmetric duplex with respect to the sequence composition of the sense and antisense 3' overhangs. The antisense siRNA molecule may then be synthesized as the complement to nucleotide positions 1 to 21 of the 23 nucleotide sequence motif. The use of symmetric 3' TT overhangs may be advantageous to ensure that the small interfering ribonucleoprotein particles (siRNPs) are formed with approximately equal ratios of sense and antisense target RNA-cleaving siRNPs (Elbashir et al., (2001) supra and Elbashir et al., 2001 supra). Analysis of sequence databases, including but not limited to the NCBI, BLAST, Derwent and GenSeq as well as commercially available oligosynthesis companies such as OLIGOENGINE®, may also be used to select siRNA sequences against EST libraries to ensure that only one gene is targeted.

Delivery of RNA Interfering Agents

Methods of delivering RNA interference agents, e.g., an siRNA, or vectors containing an RNA interference agent, to the target cells, e.g., macrophages, lymphocytes or other desired target cells, for uptake include injection of a composition containing the RNA interference agent, e.g., an siRNA, or directly contacting the cell, e.g., a macrophage, with a composition comprising an RNA interference agent, e.g., an siRNA. In another embodiment, RNA interference agent, e.g., an siRNA may be injected directly into any blood vessel, such as vein, artery, venule or arteriole, via, e.g., hydrodynamic injection or catheterization. Administration may be by a single injection or by two or more injections. The RNA interference agent is delivered in a pharmaceutically acceptable carrier. One or more RNA interference agent may be used simultaneously. In one preferred embodiment, only one siRNA that targets human PARP9 is used. In one embodiment, specific cells are targeted with RNA interference, limiting potential side effects of RNA interference caused by non-specific targeting of RNA interference. The method can use, for example, a complex or a fusion molecule comprising a cell targeting moiety and an RNA interference binding moiety that is used to deliver RNA interference effectively into cells. For example, an antibody-protamine fusion protein when mixed with siRNA, binds siRNA and selectively delivers the siRNA into cells expressing an antigen recognized by the antibody, resulting in silencing of gene expression only in those cells that express the antigen. The siRNA or RNA interference-inducing molecule binding moiety is a protein or a nucleic acid binding domain or fragment of a protein, and the binding moiety is fused to a portion of the targeting moiety. The location of the targeting moiety can be either in the carboxyl-terminal or amino-terminal end of the construct or in the middle of the fusion protein. A viral-mediated delivery mechanism can also be employed to deliver siRNAs to cells in vitro and in vivo as described in Xia, H. et al. (2002) Nat Biotechnol 20(10):1006). Plasmid- or viral-mediated delivery mechanisms of shRNA may also be employed to deliver shRNAs to cells in vitro and in vivo as described in Rubinson, D. A., et al. ((2003) Nat. Genet. 33:401-406) and Stewart, S. A., et al. ((2003) RNA 9:493-501). The RNA interference agents, e.g., the siRNAs or shRNAs, can be introduced along with components that perform one or more of the following activities: enhance uptake of the RNA interfering agents, e.g., siRNA, by the cell, e.g., lymphocytes or other cells, inhibit annealing of single strands, stabilize single strands, or otherwise facilitate delivery to the target cell and increase inhibition of the target gene, e.g., PARP9. The dose of the particular RNA interfering agent will be in an amount necessary to effect RNA interference, e.g., post translational gene silencing (PTGS), of the particular target gene, thereby leading to inhibition of target gene expression or inhibition of activity or level of the protein encoded by the target gene.

In one embodiment, the inhibitor of PARP9 expression is selected from a small molecule and a nucleic acid. Alternatively and preferably, the inhibitor of PARP9 expression is a PARP9 specific RNA interference agent, or a vector encoding said PARP9 specific RNA interference agent or an aptamer that binds specific to PARP9. In one specific embodiment, the RNA interference agent comprises one or more of the nucleotide sequences of SEQ ID NO:1-28, 33-36, and 41-44.

In one embodiment, a drug-eluting stent or bioabsorbable scaffold can be used to deliver the PARP9 inhibitor. In one embodiment, balloons for coronary, cervical, or peripheral (including renal and limb arteries) arteries can be used to deliver the PARP9 inhibitor. In one embedment, a vein graft can be incubated with a PARP9 inhibitor (e.g., siRNA or antisense oligos) before implantation to the artery. In one embodiment, drug-coated sutures can be used to deliver the PARP9 inhibitor.

Activators of PARP14

Without wishing to be bound by theory, it was discovered that PARP9 silencing tends to increase PARP14 mRNA (for example, see FIG. 10A). And thus a compound that is an inhibitor of PARP9 can also be used as an activator of PARP14.

In one embodiment of any one method, the activator of PARP14 is selected from the group consisting of an antibody against PARP9 or an antigen-binding fragment thereof, a small molecule, and a nucleic acid.

Methods used for the delivery of PARP9 inhibitors can be also used for the delivery of PAPR14 activators.

Formulation and Application

Routes of administration include, but are not limited to aerosol, direct injection, intradermal, transdermal (e.g., in slow release polymers), intravitreal, intramuscular, intraperitoneal, intravenous, subcutaneous, intranasal, epidural, topical, oral, transmucosal, buccal, rectal, vaginal, transdermal, intranasal and parenteral routes. "Parenteral" refers to a route of administration that is generally associated with injection, including but not limited to intraorbital, infusion, intraarterial, intracapsular, intracardiac, intradermal, intrahepatic, intrarogan, intramuscular, intraperitoneal, intrapulmonary, intraspinal, intrasternal, intrathecal, intrauterine, intravenous, subarachnoid, subcapsular, subcutaneous, transmucosal, or transtracheal. Any other therapeutically efficacious route of administration can be used, for example, infusion or bolus injection, absorption through epithelial or mucocutaneous linings, or by gene therapy wherein a DNA molecule encoding the therapeutic protein or peptide is administered to the patient, e.g., via a vector, which causes the protein or peptide to be expressed and secreted at therapeutic levels in vivo. In various embodiments, administration can be inhaled in to the lung via aerosol administration, e.g. with nebulization. Administration also can be systemic or local.

In some embodiments, the compositions described herein can be administered as a formulation adapted for systemic delivery. In some embodiments, the compositions described herein can be administered as a formulation adapted for delivery to specific organs, for example but not limited to the liver, spleen, the bone marrow, and the skin.

In other embodiments, the compositions described herein can be formulated for delayed or sustained release after delivery, eg, via encapsulation in liposomes or nanoparticles.

The precise dose to be employed in the formulation of the agent will also depend on the route of administration, and the seriousness of the disease or disorder, and should be decided according to the judgment of the practitioner and each patient's circumstances. Effective doses may be extrapolated from dose-response curves derived from in vitro or animal model test systems.

Efficacy testing can be performed during the course of treatment using the methods described herein. Measurements of the degree of severity of a number of symptoms associated with a particular ailment are noted prior to the start of a treatment and then at later specific time period after the start of the treatment. For example, when treating an autoimmune disease such as rheumatoid arthritis, the severity of joint pain can be scored from a number of 1-10, with a score of 1 representing mild discomfort and a score of 10 represent constant unbearable pain with or without movement; the range of motion of an affected joint can also are be measured as a degree of angle for which that joint can move. The joint pain and range of motion are noted before and after a treatment. The severity of joint pain and range of motion after the treatment are compared to those before the treatment. A decrease in the pain score and/or an increase in the degree of angle of joint movement indicate that the treatment is effective in reducing inflammation in the affected joint, thereby decreasing pain and improving joint movement.

Alternately, the treatment efficacy can be determined by measuring distribution of the population of IL-12$^{high}$, IL-23$^{high}$ and IL-10$^{low}$ M1 macrophages subtype and IL-12$^{low}$ and IL-10$^{high}$ M2 macrophages subtype in the subject prior to and after the start of treatment. The population of macrophages can be determined by FACS analysis using the markers characteristic of M1 and M2 macrophages subtype as disclosed herein from a sample of peripheral blood.

The skilled artisan will appreciate that certain factors may influence the dosage and timing required to effectively treat a subject, including but not limited to the severity of the disease or disorder, previous treatments, the general health and/or age of the subject, and other diseases present. The dose levels can also depend on whether number of risk factors, the severity of the symptoms and the susceptibility of the subject to side effects. Moreover, treatment of a subject with a therapeutically effective dose can include a single treatment or a series of treatments. Estimates of effective dosages and in vivo half-lives for the compositions described herein can be made using conventional methodologies or on the basis of in vivo testing using an appropriate animal model, as known in the art, or as described herein. Preferred dosages for a given compositions described herein are readily determinable by those of skill in the art by a variety of means.

Some embodiments of the invention are listed in the following numbered paragraphs.

[1] A composition comprising an inhibitor of poly (ADP-ribose) polymerase family, member 9 (PARP9) and/or an activator of poly (ADP-ribose) polymerase family, member 14 (PARP14) for use in inhibiting macrophage M1 activation.

[2] The composition of paragraph 1, comprising a lipid encapsulation formulation of the inhibitor of PARP9 and/or the activator of PARP14.

[3] The composition of paragraph 1 or 2, wherein the inhibitor of PARP9 inhibits the expression of PARP9.

[4] The composition of any one of paragraphs 1-3, wherein the inhibitor of PARP9 is a small molecule or a nucleic acid.

[5] The composition of paragraph 4, wherein the nucleic acid is a PARP9 specific RNA interference agent, or a vector encoding a PARP9 specific RNA interference agent.

[6] The composition of paragraph 5, wherein the RNA interference agent hybridizes to a PARP9 nucleic acid sequence.

[7] The composition of paragraph 5 or paragraph 6, wherein the RNA interference agent comprises a nucleic sequence derived from the human PARP9 gene having a GENBANK™ Accession number BC039580.

[8] The composition of any one of paragraphs 5-7, wherein the RNA interference agent comprises one or more of the nucleotide sequences selected from a group consisting of SEQ ID NOS: 1-28, 33-36, and 41-44.

[9] The composition of paragraph 1 or 2, wherein the inhibitor of PARP9 inhibits PARP9 protein's activity.

[10] The composition of paragraph 9, wherein the inhibitor of PARP9 is selected from the group consisting of an antibody against PARP9 or an antigen-binding fragment thereof, a small molecule, and a nucleic acid.

[11] The composition of any one of paragraphs 1-10, wherein the activator of PARP14 increases the expression of PARP14 and/or PARP14 protein's activity.

[12] The composition of paragraph 11, wherein the activator of PARP14 is selected from the group consisting of an antibody against PARP9 or an antigen-binding fragment thereof, a small molecule, and a nucleic acid.

[13] A composition comprising an inhibitor of poly (ADP-ribose) polymerase family, member 9 (PARP9) and/or an activator of poly (ADP-ribose) polymerase family, member 14 (PARP14) for use in the manufacture of a medicament for inhibiting macrophage M1 activation.

[14] The composition of paragraph 13, comprising a lipid encapsulation formulation of the inhibitor of PARP9 and/or the activator of PARP14.

[15] The composition of paragraph 13 or 14, wherein the inhibitor of PARP9 inhibits the expression of PARP9.

[16] The composition of any one of paragraphs 13-15, wherein the inhibitor of PARP9 is a small molecule or a nucleic acid.

[17] The composition of paragraph 16, wherein the nucleic acid is a PARP9 specific RNA interference agent, or a vector encoding a PARP9 specific RNA interference agent.

[18] The composition of paragraph 17, wherein the RNA interference agent hybridizes to a PARP9 nucleic acid sequence.

[19] The composition of paragraph 17 or paragraph 18, wherein the RNA interference agent comprises a nucleic sequence derived from the human PARP9 gene having a GENBANK™ Accession number BC039580.

[20] The composition of any one of paragraphs 17-19, wherein the RNA interference agent comprises one or more of the nucleotide sequences selected from a group consisting of SEQ ID NOS: 1-28, 33-36, and 41-44.

[21] The composition of paragraph 13 or 14, wherein the inhibitor of PARP9 inhibits PARP9 protein's activity.

[22] The composition of paragraph 21, wherein the inhibitor of PARP9 is selected from the group consisting of an antibody against PARP9 or an antigen-binding fragment thereof, a small molecule, and a nucleic acid.

[23] The composition of any one of paragraphs 13-22, wherein the activator of PARP14 increases the expression of PARP14 and/or PARP14 protein's activity.

[24] The composition of paragraph 23, wherein the activator of PARP14 is selected from the group consisting of an antibody against PARP9 or an antigen-binding fragment thereof, a small molecule, and a nucleic acid.

[25] A method of inhibiting macrophage M1 activation comprising contacting a population of monocytes or macrophages with an effective amount of a composition comprising an inhibitor of poly (ADP-ribose) polymerase family, member 9 (PARP9) and/or an activator of poly (ADP-ribose) polymerase family, member 14 (PARP14).

[26] The method of paragraph 25, wherein the inhibition of macrophage M1 activation comprises inhibiting pro-inflammatory M1 polarization.

[27] The method of paragraph 26, wherein the inhibition of macrophage M1 activation comprises the suppression of a pro-inflammatory M1 gene.

[28] The method of paragraph 27, wherein the pro-inflammatory M1 gene suppressed is selected from the group consisting of tumor necrosis factor alpha (TNF-α), interleukin 1β (IL-1β) and inducible nitric oxide synthase (iNOS).

[29] The method of any one of paragraphs 25-28, wherein the inhibition of macrophage M1 activation comprises increasing the expression of an anti-inflammatory M2 marker.

[30] The method of paragraph 29, wherein the anti-inflammatory M2 marker is arginase 1 (Arg1) or mannose receptor, C type 1 (MRC1).

[31] The method of any one of paragraphs 25-30, wherein the population of monocytes or macrophage is contacted ex vivo or in vitro or in vivo.

[32] The method of any one of paragraphs 25-31, wherein the composition comprises a lipid encapsulation formulation of the inhibitor of PARP9 and/or the activator of PARP14.

[33] The method of any one of paragraphs 25-32, wherein the inhibitor of PARP9 inhibits the expression of PARP9.

[34] The method of any one of paragraphs 25-33, wherein the inhibitor of PARP9 is a small molecule or a nucleic acid.

[35] The method of paragraph 34, wherein the nucleic acid is a PARP9 specific RNA interference agent, or a vector encoding a PARP9 specific RNA interference agent.

[36] The method of paragraph 35, wherein the RNA interference agent hybridizes to a PARP9 nucleic acid sequence.

[37] The method of paragraph 36, wherein the RNA interference agent comprises a nucleic sequence derived from the human PARP9 gene having a GENBANK™ Accession number BC039580.

[38] The method of any one of paragraphs 34-37, wherein the RNA interference agent comprises one or more of the nucleotide sequences selected from a group consisting of SEQ ID NOS: 1-28, 33-36, and 41-44.

[39] The method of any one of paragraphs 25-32, wherein the inhibitor of PARP9 inhibits PARP9 protein's activity.

[40] The method of paragraph 39, wherein the inhibitor of PARP9 is selected from the group consisting of an antibody against PARP9 or an antigen-binding fragment thereof, a small molecule, and a nucleic acid.

[41] The method of any one of paragraphs 25-40, wherein the activator of PARP14 increases the expression of PARP14 and/or PARP14 protein's activity.

[42] The method of paragraph 41, wherein the activator of PARP14 is selected from the group consisting of an antibody against PARP9 or an antigen-binding fragment thereof, a small molecule, and a nucleic acid.

[43] A method of inhibiting M1 macrophage activation comprising contacting a primary macrophage with an effective amount of a composition comprising an inhibitor of poly (ADP-ribose) polymerase family, member 9 (PARP9).

[44] A method of inhibiting macrophage M1 activation comprising contacting a population of monocytes or macrophages with an effective amount of a composition comprising an activator of poly (ADP-ribose) polymerase family, member 14 (PARP14).

[45] A method of inhibiting macrophage M1 activation comprising contacting a population of monocytes or macrophages with an effective amount of a composition comprising an inhibitor of poly (ADP-ribose) polymerase family, member 9 (PARP9) and an activator of poly (ADP-ribose) polymerase family, member 14 (PARP14).

[46] A method of inhibiting macrophage M1 activation comprising the steps of: (a) providing a population of monocytes or macrophages; and (b) contacting the population of monocytes or macrophages with an effective amount of a composition comprising an inhibitor of poly (ADP-ribose) polymerase family, member 9 (PARP9) and/or an activator of poly (ADP-ribose) polymerase family, member 14 (PARP14).

[47] The method of any one of paragraphs 43-46, wherein the inhibition of macrophage M1 activation comprises inhibiting pro-inflammatory M1 polarization.

[48] The method of any one of paragraphs 43-47, wherein the inhibition of macrophage M1 activation comprises the suppression of a pro-inflammatory M1 gene.

[49] The method of paragraph 48, wherein the pro-inflammatory M1 gene suppressed is selected from the group consisting of tumor necrosis factor alpha (TNF-α), interleukin 1β (IL-1β) and inducible nitric oxide synthase (iNOS).

[50] The method of any one of paragraphs 43-49, wherein the inhibition of macrophage M1 activation comprises increasing the expression of an anti-inflammatory M2 marker.

[51] The method of paragraph 50, wherein the anti-inflammatory M2 marker is arginase 1 (Arg1) or mannose receptor, C type 1 (MRC1).

[52] The method of any one of paragraphs 43-51, wherein the population of monocytes or macrophage is contacted ex vivo or in vitro or in vivo.

[53] The method of any one of paragraphs 43-52, wherein the composition comprises a lipid encapsulation formulation of the inhibitor of PARP9 and/or the activator of PARP14.

[54] The method of any one of paragraphs 43, 45-53, wherein the inhibitor of PARP9 inhibits the expression of PARP9.

[55] The method of any one of paragraphs 43, 45-54, wherein the inhibitor of PARP9 is a small molecule or a nucleic acid.

[56] The method of paragraph 55, wherein the nucleic acid is a PARP9 specific RNA interference agent, or a vector encoding a PARP9 specific RNA interference agent.

[57] The method of paragraph 56, wherein the RNA interference agent hybridizes to a PARP9 nucleic acid sequence.

[58] The method of paragraph 57, wherein the RNA interference agent comprises a nucleic sequence derived from the human PARP9 gene having a GENBANK™ Accession number BC039580.

[59] The method of any one of paragraphs 55-58, wherein the RNA interference agent comprises one or more of the nucleotide sequences selected from a group consisting of SEQ ID NOS: 1-28, 33-36, and 41-44.

[60] The method of any one of paragraphs 43, 45-53, wherein the inhibitor of PARP9 inhibits PARP9 protein's activity.

[61] The method of paragraph 60, wherein the inhibitor of PARP9 is selected from the group consisting of an antibody against PARP9 or an antigen-binding fragment thereof, a small molecule, and a nucleic acid.

[62] The method of any one of paragraphs 44-61, wherein the activator of PARP14 increases the expression of PARP14 and/or PARP14 protein's activity.

[63] The method of paragraph 62, wherein the activator of PARP14 is selected from the group consisting of an antibody against PARP9 or an antigen-binding fragment thereof, a small molecule, and a nucleic acid.

[64] A method of inhibiting excessive or sustained inflammation in a subject in need thereof comprising contacting a population of monocytes and/or macrophages from the subject with an effective amount of a composition comprising an inhibitor of poly (ADP-ribose) polymerase family, member 9 (PARP9) and/or poly (ADP-ribose) polymerase family, member 14 (PARP14).

[65] The method of paragraph 64, further comprising selecting a subject having excessive or sustained inflammation.

[66] The method of paragraph 64 or 65, wherein the inhibition of excessive or sustained inflammation comprises inhibiting pro-inflammatory M1 polarization.

[67] The method of any one of paragraphs 64-66, wherein the inhibition of macrophage M1 activation comprises the suppression of a pro-inflammatory M1 gene.

[68] A method of treating or preventing atherosclerosis and/or a vascular disease in a subject in need thereof comprising contacting a population of monocytes and/or macrophages from the subject with an effective amount of a composition comprising of an inhibitor of poly (ADP-ribose) polymerase family, member 9 (PARP9) and/or an activator of poly (ADP-ribose) polymerase family, member 14 (PARP14).

[69] The method of paragraph 68, whereby the pro-inflammatory M1 polarization of the contacted monocytes and/or macrophages in the subject is inhibited.

[70] The method of paragraph 69, wherein the inhibition of monocytes and/or macrophage pro-inflammatory M1 polarization comprises the suppression of a pro-inflammatory M1 gene.

[71] The method of paragraph 67 or 70, wherein the pro-inflammatory M1 gene suppressed is selected from the group consisting of tumor necrosis factor alpha (TNF-α), interleukin 1β (IL-1β) and inducible nitric oxide synthase (iNOS).
[72] The method of any one of paragraphs 64-67, and 71, wherein the inhibition of macrophage activation comprises increasing the expression of an anti-inflammatory M2 marker.
[73] The method of any one of paragraphs 68-71, whereby the expression of an anti-inflammatory M2 marker in monocytes and/or macrophages in the subject is increased.
[74] The method of paragraph 72 or 73, wherein the anti-inflammatory M2 marker is arginase 1 (Arg1) or mannose receptor, C type 1 (MRC1).
[75] The method of any one of paragraphs 64-74, wherein the population of monocytes or macrophage is contacted ex vivo or in vitro or in vivo.
[76] The method of any one of paragraphs 64-75, wherein the composition comprises a lipid encapsulation formulation of the inhibitor of PARP9 and/or the activator of PARP14.
[77] The method of any one of paragraphs 64-76, wherein the inhibitor of PARP9 inhibits the expression of PARP9.
[78] The method of any one of paragraphs 64-77, wherein the inhibitor of PARP9 is a small molecule or a nucleic acid.
[79] The method of paragraph 78, wherein the nucleic acid is a PARP9 specific RNA interference agent, or a vector encoding a PARP9 specific RNA interference agent.
[80] The method of paragraph 79, wherein the RNA interference agent hybridizes to a PARP9 nucleic acid sequence.
[81] The method of paragraph 80, wherein the RNA interference agent comprises a nucleic sequence derived from the human PARP9 gene having a GEN-BANK™ Accession number BC039580.
[82] The method of any one of paragraphs 78-81, wherein the RNA interference agent comprises one or more of the nucleotide sequences selected from a group consisting of SEQ ID NOS: 1-28, 33-36, and 41-44.
[83] The method of any one of paragraphs 64-76, wherein the inhibitor of PARP9 inhibits PARP9 protein's activity.
[84] The method of paragraph 83, wherein the inhibitor of PARP9 is selected from the group consisting of an antibody against PARP9 or an antigen-binding fragment thereof, a small molecule, and a nucleic acid.
[85] The method of any one of paragraphs 64-84, wherein the activator of PARP14 increases the expression of PARP14 and/or PARP14 protein's activity.
[86] The method of paragraph 85, wherein the activator of PARP14 is selected from the group consisting of an antibody against PARP9 or an antigen-binding fragment thereof, a small molecule, and a nucleic acid.
[87] The method of any one of paragraphs 64-86, wherein the composition comprising the inhibitor of PARP9 and/or the activator of PARP14 further comprises a pharmaceutically acceptable carrier or diluent.
[88] The method of any one of paragraphs 64-87, wherein the composition is administered by injection, infusion, or instillation.
[89] The method of any one of paragraphs 64-67, 71-72, 74-88, wherein the excessive or sustained inflammation is found in a condition selected from the group consisting of atherosclerosis, obesity, type 2 diabetes, vasculitis, limb ischemia, vein graft disease, AV fistulas and/or grafts, fatty liver disease, brain damage after stroke, brain traumatic injury, cardiac remodeling after acute myocardial infarction, cardiac valve disease, tissue engineered organs, transplanted organs, cancers, Gaucher's disease, autoimmune or autoinflammatory disease, and inflammatory bowel disease.
[90] The method of paragraph 89, wherein the autoimmune or autoinflammatory disease is selected from the group consisting of rheumatoid arthritis, lupus erythematosus, and Behçet's disease.
[91] The method of any one of paragraphs 64, 66-90 further comprises selecting a subject is at risk of developing an excessive or sustained inflammation.
[92] A method of inhibiting excessive or sustained inflammation in a subject in need thereof comprising administering to the subject an effective amount of a pharmaceutical composition comprising of an inhibitor of poly (ADP-ribose) polymerase family, member 9 (PARP9) and/or an activator of poly (ADP-ribose) polymerase family, member 14 (PARP14) and a pharmaceutically acceptable carrier or diluent.
[93] A method of treating or preventing atherosclerosis and/or a vascular disease in a subject in need thereof comprising the step of (a) identifying a subject who has or is at risk of atherosclerosis; and (b) administering to the subject an effective amount of a pharmaceutical composition comprising of an inhibitor of poly (ADP-ribose) polymerase family, member 9 (PARP9) and/or an activator of poly (ADP-ribose) polymerase family, member 14 (PARP14) and a pharmaceutically acceptable carrier or diluent.
[94] The method of paragraph 92 or 93, whereby pro-inflammatory M1 polarization of monocytes and/or macrophages in the subject is inhibited.
[95] The method of paragraph 94, wherein the inhibition of monocytes and/or macrophage pro-inflammatory M1 polarization comprises the suppression of a pro-inflammatory M1 gene.
[96] The method of paragraph 95, wherein the pro-inflammatory M1 gene suppressed is selected from the group consisting of tumor necrosis factor alpha (TNF-α), interleukin 1β (IL-1β) and inducible nitric oxide synthase (iNOS).
[97] The method of any one of paragraphs 92-96, whereby an anti-inflammatory M2 marker expression in monocytes and/or macrophages in the subject is increased.
[98] The method of paragraph 97, wherein the anti-inflammatory M2 marker is arginase 1 (Arg1) or mannose receptor, C type 1 (MRC1).
[99] The method of paragraph 92-97, wherein the inhibitor of PARP9 inhibits the expression of PARP9.
[100] The method of any one of paragraphs 92-99, wherein the inhibitor of PARP9 is a small molecule or a nucleic acid.
[101] The method of paragraph 100, wherein the nucleic acid is a PARP9 specific RNA interference agent, or a vector encoding a PARP9 specific RNA interference agent.
[102] The method of paragraph 101, wherein the RNA interference agent hybridizes to a PARP9 nucleic acid sequence.
[103] The method of paragraph 102, wherein the RNA interference agent comprises a nucleic sequence derived from the human PARP9 gene having a GEN-BANK™ Accession number BC039580.

[104] The method of any one of paragraphs 101-103, wherein the RNA interference agent comprises one or more of the nucleotide sequences selected from a group consisting of SEQ ID NOS: 1-28, 33-36, and 41-44.

[105] The method of any one of paragraphs 92-97, wherein the inhibitor of PARP9 inhibits PARP9 protein's activity.

[106] The method of paragraph 105, wherein the inhibitor of PARP9 is selected from the group consisting of an antibody against PARP9 or an antigen-binding fragment thereof, a small molecule, and a nucleic acid.

[107] The method of any one of paragraphs 92-106, wherein the activator of PARP14 increases the expression of PARP14 and/or PARP14 protein's activity.

[108] The method of paragraph 107, wherein the activator of PARP14 is selected from the group consisting of an antibody against PARP9 or an antigen-binding fragment thereof, a small molecule, and a nucleic acid.

[109] The method of any one of paragraphs 92-108, wherein the pharmaceutical composition is administered by injection, infusion, or instillation.

[110] The method of any one of paragraphs 92-109, wherein the pharmaceutical composition comprises a formulation comprising lipid encapsulation of the inhibitor of PARP9 and/or an activator of PARP14 and a pharmaceutically acceptable carrier or diluent.

[111] The method of any one of paragraphs 92, 94-110, wherein the excessive or sustained inflammation is found in a condition selected from the group consisting of atherosclerosis, obesity, type 2 diabetes, vasculitis, limb ischemia, vein graft disease, AV fistulas and/or grafts, fatty liver disease, brain damage after stroke, brain traumatic injury, cardiac remodeling after acute myocardial infarction, cardiac valve disease, tissue engineered organs, transplanted organs, cancers, Gaucher's disease, autoimmune or autoinflammatory disease, and inflammatory bowel disease.

[112] The method of paragraph 111, wherein the autoimmune or autoinflammatory disease is selected from the group consisting of rheumatoid arthritis, lupus erythematosus, and Behçet's disease.

[113] The method of any one of paragraphs 92-112 further comprises selecting a subject who has or is at risk of developing excessive or sustained inflammation.

[114] The method of any one of paragraphs 93-113 further comprising selecting the subject for administration of the pharmaceutical composition.

[115] The method of claim 89 or 111, wherein the atherosclerosis occurs in coronary, carotid, ilio-femoral, renal or other arteries.

[116] A composition comprising an inhibitor of poly (ADP-ribose) polymerase family, member 9 (PARP9) and/or an activator of poly (ADP-ribose) polymerase family, member 14 (PARP14) for use in the manufacture of a medicament for inhibiting macrophage activation.

[117] A composition comprising an inhibitor of poly (ADP-ribose) polymerase family, member 9 (PARP9) and/or an activator of poly (ADP-ribose) polymerase family, member 14 (PARP14) for use in inhibiting macrophage activation.

[118] A method of inhibiting pro-inflammatory macrophage activation comprising the steps of (a) providing a population of monocytes or macrophages or a mixture of both cell types; and (b) contacting the population of monocytes or macrophages with an effective amount of a composition comprising an inhibitor of PARP9 and/or an activator of PARP14.

[119] A method of inhibiting pro-inflammatory macrophage activation comprising contacting a population of monocytes or macrophages with an effective amount of a composition comprising an inhibitor of PARP9 and an activator of PARP14.

[120] A method of inhibiting pro-inflammatory macrophage activation comprising contacting a population of monocytes or macrophages with an effective amount of a composition comprising an inhibitor of PARP9 and/or an activator of PARP14.

[121] A method of inhibiting pro-inflammatory macrophage activation comprising contacting a population of monocytes or macrophages with an effective amount of a composition comprising an inhibitor of PARP9.

[122] A method of inhibiting pro-inflammatory macrophage activation comprising contacting a population of monocytes or macrophages with an effective amount of a composition comprising an activator of PARP14.

[123] The method or composition of any one of paragraphs 116-122, wherein the pro-inflammatory macrophage activation comprises M1 activation.

This invention is further illustrated by the following example which should not be construed as limiting. The contents of all references cited throughout this application, as well as the figures and table are incorporated herein by reference.

Those skilled in the art will recognize, or be able to ascertain using not more than routine experimentation, many equivalents to the specific embodiments of the invention described herein. Such equivalents are intended to be encompassed by the following claims.

EXAMPLE

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The following examples do not in any way limit the invention.

Example 1

The inventors have explored key regulators of macrophage polarization for modulating pathological activation of macrophages as novel therapeutic targets of various oinflammatory diseases. The tandem mass tagging strategy (TMT) was used to quantify the changes in the proteomes of mouse and human macrophage cell lines, RAW264.7 and THP-1 respectively, in response to either interferon gamma (IFNγ) as an M1 stimulator or interleukin 4 (IL-4) as an M1 inducer. The inventors quantified 5816 proteins from mouse and 4723 in human cell line. By cluster analysis of these data, poly(ADP-ribose) polymerase 9 (PARP9), PARP14 and DTX3L were identified as candidates of master regulators of macrophage polarization. Silencing of PARP14 gene induced pro-inflammatory M1 genes (TNF-α, IL-1β and iNOS), while decrease anti-inflammatory M2 markers (Arg1 and MRC1), indicating that PARP14 suppresses M1 pro-inflammatory macrophage activation and promotes anti-inflammatory M2 polarization with inducing phosphorylation of STAT1 and reducing STAT6 phosphorylation, indicating their roles in the signal tranduction mechanisms. Additionally, in primary macrophages derived from PARP14-deficient mice, M1 genes dramatically increased (more than 40 times), while M2 markers drastically decreased (less than 1/30). In contrast, siRNA silencing experiments demonstrated that PARP9 promotes M1 activation via STAT1 phosphorylation with supressing STAT6 activation. Immunoprecipitation assay indicated that PARP9, PARP14 and DTX3L (deltex 3-like, an E3 ubiquitin ligase) have direct interaction.

Example 2: PARP9 and PARP14 are Novel Regulators of Macrophage Activation

Atherosclerosis causes acute myocardial infarction, the number one killer in the United States and other developed countries (1). Despite medical advances, the global burden of ischemic heart disease has been increasing (2). Macrophage activation participates in the pathogenesis of many disorders, including atherosclerosis (3-6). Metabolic disorders such as dyslipidemia and diabetes promote recruitment of circulating monocytes into the vessel wall, where they differentiate into macrophages. Pro-inflammatory microenvironment further induces activation of macrophages. The preclinical evidence, including our own, have proposed that activated macrophages not only participate in the development of atherosclerosis but also trigger its thrombotic complications by reducing the integrity of atherosclerotic plaques (7). Accumulating clinical evidence also has linked vascular inflammation and cardiovascular events (8). Macrophage activation appears to play a key role in the pathogenesis of various other diseases such as type 2 diabetes (9, 10) Some pathways associated with macrophage activation may thus contribute to the shared mechanisms of inflammatory diseases, as demonstrated (11, 12). In cardiovascular diseases, despite potent therapies such as cholesterol lowering by statins, substantial residual risk remains (7, 13, 14), which drives the active search for novel solutions against macrophage activation.

Dissecting complex and intertwined mechanisms for macrophage activation requires well-defined mechanistic models. The concept of M1/M2 polarization provides a framework for the heterogeneity of macrophages, although a strict dichotomy may not apply particularly in humans (15-22). The present study uses this well-established in vitro construct, which has clear relationships between stimuli and responses, as a starting point to simplify long and exhausting global proteomic and bioinformatics analyses. In both mouse and human datasets, poly ADP-ribose polymerase 14 (PARP14), also known as ADP-ribosyltransferase diphtheria toxin-like 8 (ARTD8), and PARP9/ARTD9 showed promise as candidates for key molecules in macrophage polarization. The presence of the PARP catalytic domain, which transfers ADP-ribose moieties from NAD to protein acceptors, characterizes the PARP family proteins (23). The best-characterized member, PARP1/ARTD1, represents poly-ADP-ribosylation enzymes. Yet recent evidence also validates mono-ADP-ribosylation as an important regulatory mechanism (24). PARP14/ARTD8 is an intracellular mono-ADP-ribosyltransferase. Previous reports revealed that PARP14 enhances IL-4-induced transcription by interacting with a signal transducer and activator of transcription 6 (STATE) (25) in B cells, and that ADP-ribosylation of histone deacetylase 2 (HDAC2) and HDAC3 in T helper lymphocytes (26) mediates this process. Less information exists regarding the molecular function of PARP9/ARTD9. PARP9 may lack catalytic activity (27) and mediates IFNγ-STAT1 signaling in B-cell lymphoma (28). The role of PARP14 or PARP9 in macrophages, however, remains unknown.

This study has aimed to discover therapeutic targets for macrophage-mediated inflammatory diseases. To provide clinically relevant evidence for the novel mechanisms involved in macrophage activation, we took a multidisciplinary approach, involving proteomics, systems biology, and cell and molecular biology. Our multi-scale modeling has utilized mouse and human cell lines and primary macrophages, followed by in vivo validation studies in PARP14 deficient (PARP14−/−) mouse and human samples. Our data demonstrate novel mechanisms for macrophage activation and offer the potential for new therapies for cardiovascular disease and various other disorders in which macrophage activity impacts outcomes.

Materials and Methods

Liquid Chromatography Tandem Mass Spectrometry (LC-MS/MS)

The high resolution/accuracy LTQ-Orbitrap Elite (Thermo Scientific) analyzed TMT peptide samples and the Q Exactive (Thermo Scientific) analyzed in vitro ribosylated peptides. Both mass spectrometers are fronted with a Nanospray FLEX ion source, and coupled to an Easy-nLC1000 HPLC pump (Thermo Scientific). The peptides were subjected to a dual column set-up: an Acclaim PepMap RSLC C18 trap column, 75 um×20 cm (50 um×15 cm on the Q Exactive); and an Acclaim PepMap RSLC C18 analytical column 75 um×250 mm (Thermo Scientific). For TMT analysis the analytical gradient was run at 250 nl/min from 10 to 30% Solvent B (acetonitrile/0.1% formic acid) for 90 minutes, followed by five minutes of 95% Solvent B. Solvent A was 0.1% formic acid. For ribosylated peptides the gradient was run at 250 nl/min from 5 to 28% Solvent B for 30 minutes, followed by five minutes of 95% Solvent B. All reagents were HPLC-grade. The LTQ-Orbitrap was set to 120 K resolution, and the top 20 precursor ions (within a scan range of 380-2000 m/z) were subjected to higher energy collision induced dissociation (HCD, collision energy 40%, isolation width 3 m/z, dynamic exclusion enabled, starting m/z fixed at 120 m/z, and resolution set to 30 K) for peptide sequencing (MS/MS). The Q Exactive was set to 140 K resolution with a top 10 precursor selection method (scan range of 380-1500 m/z). HCD was set to a stepped normalized collision energy of 25+/−10%, isolation width of 1.6 m/z, dynamic exclusion enabled, and resolution set to 17.5 K for MS/MS. Ribosylated peptide candidates were screened in the MS/MS scan by the m6 peak of 348.1(39, 40). Unmodified forms were calculated by subtracting the mass of the ADP-ribose (541.06 Da) from the observed precursor. Modified and unmodified m/z values and corresponding retention time windows were submitted to an inclusion list and analyzed in using the data-independent acquisition module of the Q Exactive (R=35 K).

The MS/MS data were queried against the mouse or human UniProt database (downloaded on Mar. 27, 2012) using the SEQUEST search algorithm, via the Proteome Discoverer (PD) Package (version 1.3, Thermo Scientific) (41), using a 10 ppm tolerance window in the MS1 search space, and a 0.02 Da fragment tolerance window for HCD. Methionine oxidation was set as a variable modification, and carbamidomethylation of cysteine residues and 6-plex TMT tags (Thermo Scientific) were set as fixed modifications. The peptide false discovery rate (FDR) was calculated using Percolator provided by PD: the FDR was determined based on the number of MS/MS spectral hits when searched against the reverse, decoy mouse or human database(42, 43). Peptides were filtered based on a 1% FDR. Peptides assigned to a given protein group, and not present in any other protein group, were considered as unique. Consequently, each protein group is represented by a single master protein (PD Grouping feature). Master proteins with two or more unique peptides were used for TMT reporter ratio quantification (Table 2). Ribosylation spectra were manually annotated(39, 40)

Proteomics Data Mining and Filtering

The median protein abundances were normalized to time zero and transformed into log space. To extract the proteins that increase in M1 but decrease in M2, a simple filtering logic that exploited the available M0 data set was applied. In this study, M0 serves as a baseline control for the biological noise in the system; that is, M1 and M2 protein traces that exceed the edges of the baseline are more likely to be bona fide M1- or M2-specific responses. Protein profiles whose abundances surpassed the baseline after supplement of INFγ (i.e. 0 hrs) established the general threshold for the entire time M1 data set. This cut-off value (+0.13, log 10 of relative abundance) was the same value used for both RAW264.7 and THP-1 M1 data sets. Moreover, the proteins extracted from the M1 filtering step were cross-referenced not only to the M0 but also to M2 data sets where proteins were expected to possess opposite profiles, regardless of the time points, with respect to M1. Therefore, the final list of candidate proteins had profiles whose M1 and M2 abundances increased and decreased, respectively, beyond their baseline controls.

Proteomics Data Clustering

Figure 7A:
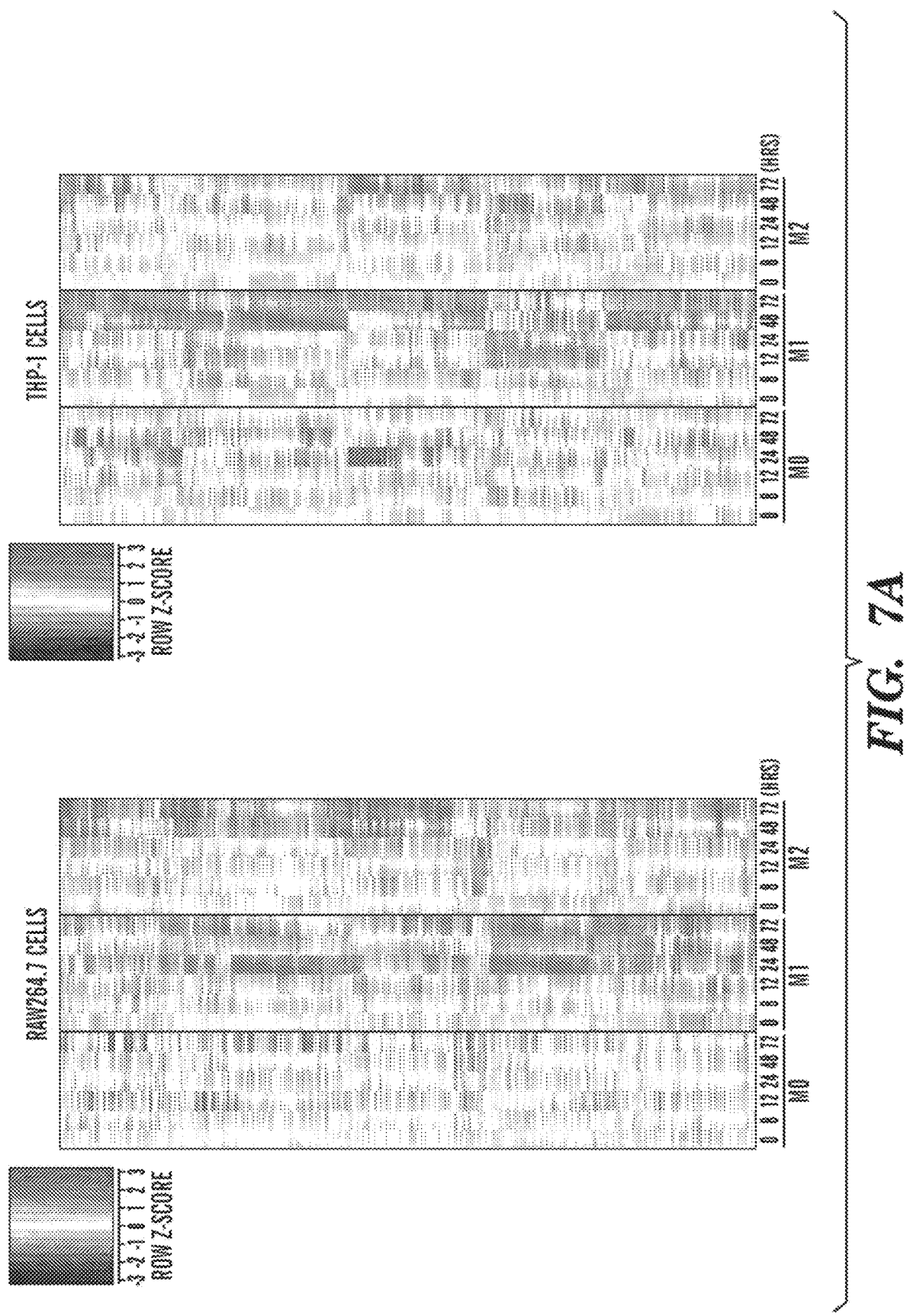
FIGS. 7A-7B show clustering strategies to identify candidates of master regulators in macrophage polarization.
Figure 7B:
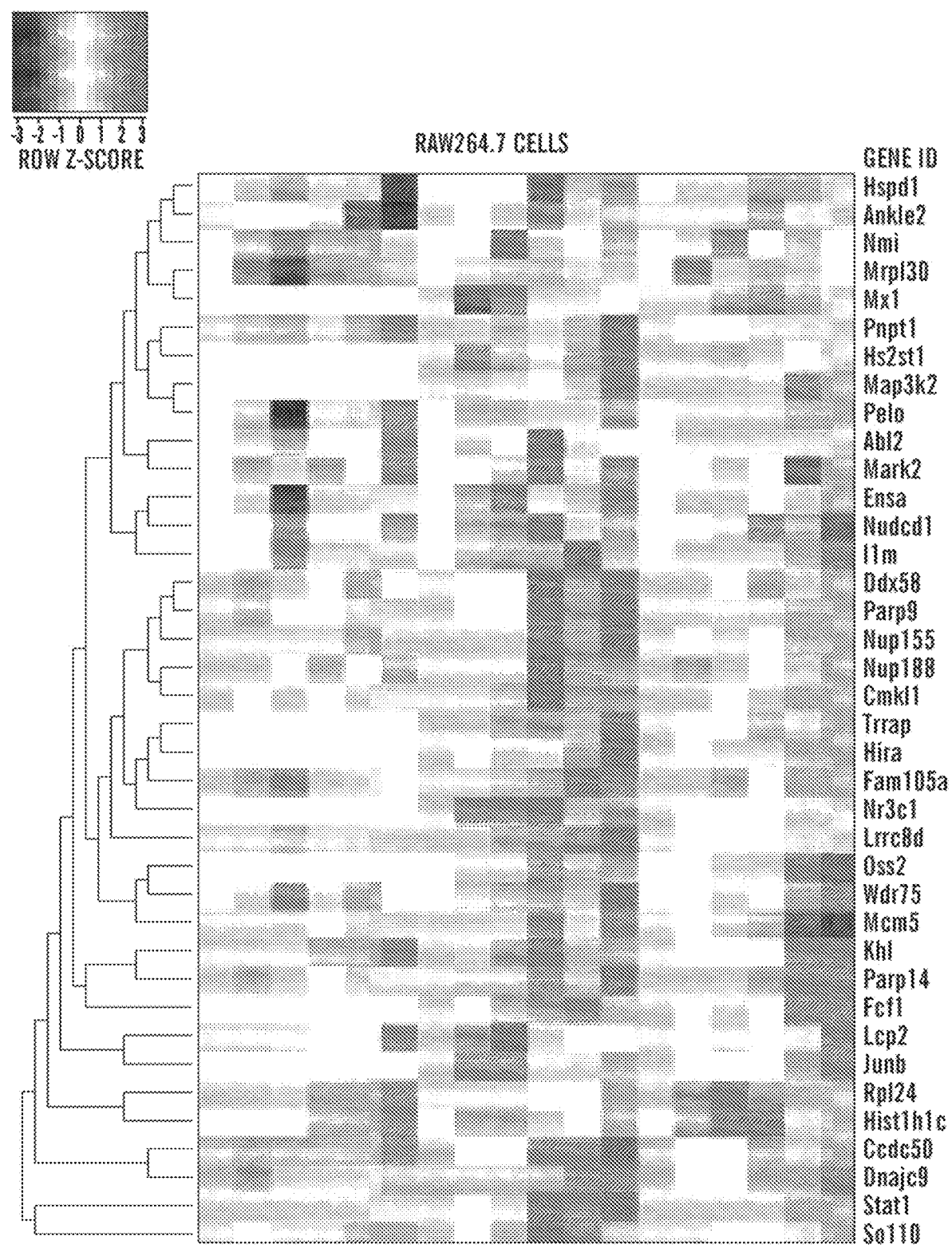
Figure 7B:
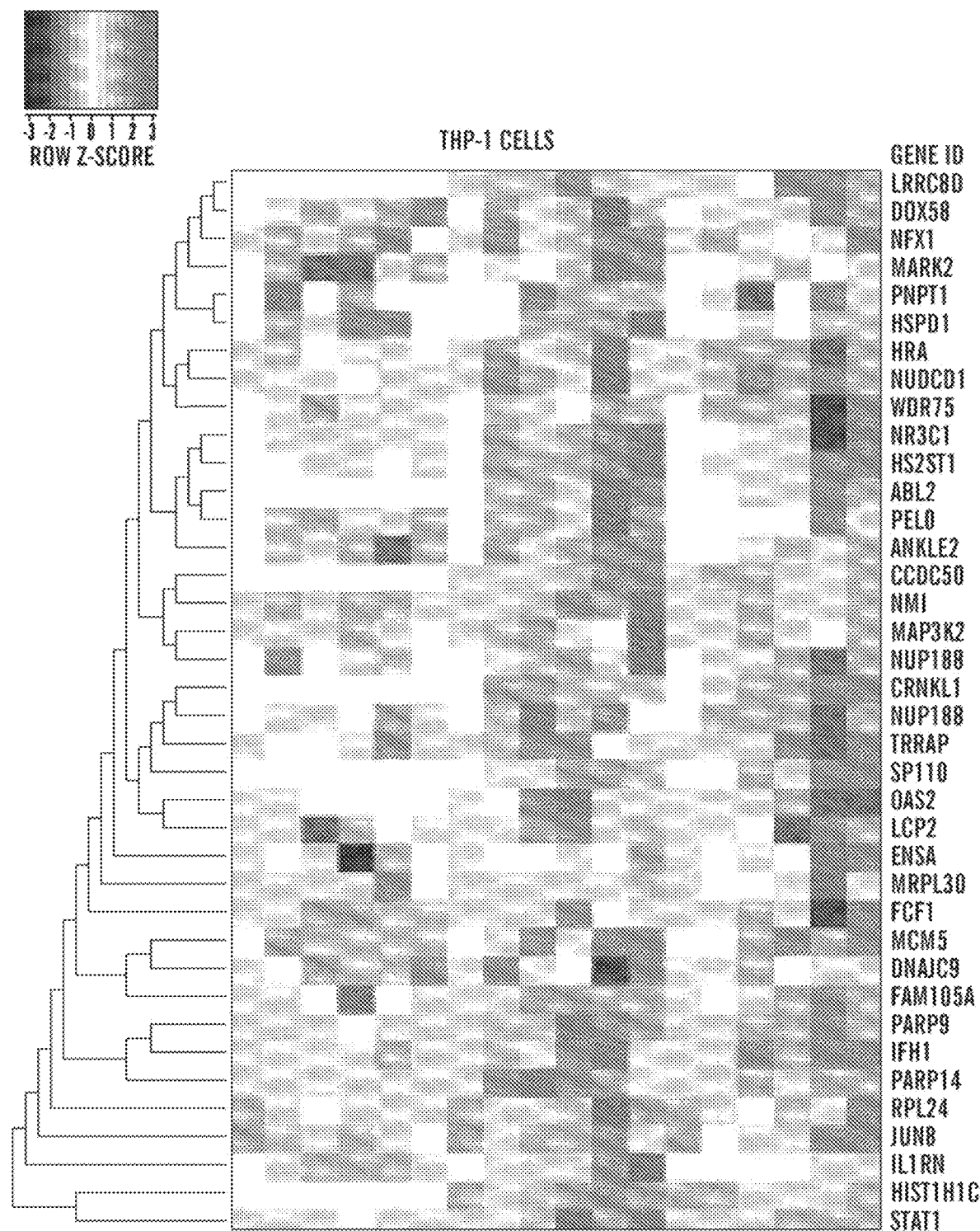

Clustering was performed using the Model-based algorithm(44) in R which is based on finite mixture models; as such it can successfully be applied to time series data analyses(43) such as those acquired for the macrophage polarization experiments. In this approach, each time series (protein profile) $y_i$, $i=1, 2, \ldots, N$ (where N is the number of TMT channels) is considered to be a single entity connected by a line. Clustering is achieved for a traditional finite mixture model by assigning each time series, $y_i$, to a cluster. The unsupervised Model-based clustering uses the Expectation Maximization algorithm (EM) to assign the profile to a specific cluster. MCLUST has the advantage of using the Bayesian Information Criteria (BIC) to determine the number of clusters that best partition the data set, by maximizing the intra-data set variability. Finally, stronger covariance (and thus also dependencies) between sets of two time points is enabled by sum-normalization (45). After clustering was performed, proteins shared in all three data sets (M0, M1 and M2) for both RAW264.7 and THP-1 cells were focused on, with the purpose of identifying proteins whose profiles increased in M1 and decreased in M2, but maintained at basal levels in M0. All clusters were inspected, looking for an increase in the relative abundance of proteins with respect to time zero at any time point in M1, and the M2 and M0 clusters were subsequently cross-referenced for proteins whose profiles decreased and remained within the baseline, respectively. The proteins that fulfilled these three criteria are shown in the heat maps for RAW264.7 and THP-1 cells data sets (FIG. 7B). Finally, to further narrow the list of proteins of interest, those that were in common to both species were prioritized (FIG. 7B), as determined by identical Uniprot protein IDs. Heat maps were used only with the aim of ordering the protein expression levels according to the row obtained Z-score (i.e. $z=(x-mean)/sd$). The proteins were clustered in the horizontal direction hierarchically using Euclidean distance and average linkage methods. In this data matrix, each column represents the TMT time-point analysis 0, 8, 12, 24, 48, 72 hours and each row corresponds to a protein gene ID.

PARP14-PARP9 Network Analysis

As a parallel approach to further investigate the candidacy of PARP14 and PARP9 as cardiovascular and metabolic diseases, in silico or network-based prediction methods were used under the premise that a potential PARP14/PARP9 interactome would be close in vicinity to its pertinent vascular disease network/module.

To evaluate the impact of PARP14/PARP9 neighbors, HumanNet interaction database was used (46). The random-walk methodology(31) was then used to construct the disease modules from the functional database using gene-disease associations extracted from genome-wide association studies (GWAS), and from the OMIM and the MalaCards databases for: Cardiomyopathy, Coronary Heart disease, Heart Failure, Hypercholestermia, Hypertension, Metabolic Traits, Osteoporosis, Cardiovascular Risk Factors and Sudden Cardiac Arrest. The PARP9-PARP14 module was determined by first neighbors in the functional database. Further, the first neighbors were restricted to those that are expressed in macrophages based on gene-expression. Based on this selection, 55 first neighbors were considered for PARP9 and 149 for PARP14 that were annotated collectively as the PARP9-PARP14 module. Further, the closeness of the first neighbors was measured using the shortest-path topology measure with the diseases modules above. For each disease module, the shortest path distances to the PARP9-PARP14 module was calculated and these distances were compared to the random distance distribution with the same module size (Wilcoxon test and Benjamini-Hochberg correction for multiple-testing). Finally, it was verified that the module size does not affect the significance of the p-values for the Coronary Heart Disease and Osteoporosis modules by recalculating the random distances by reducing the module size to the top 35 genes from random walk.

Cell Culture

In this study, mouse and human interferon gamma (IFNγ) 10 ng/ml and interleukin 4 (IL-4) 10 ng/ml (R&D systems) were used as M1 and M2 stimuli, respectively.

Cell Lines

The murine monocyte/macrophage cell line RAW264.7 was obtained from American Type Culture Collection (ATCC, Rockville, Md.) and maintained in 10% fetal bovine serum (FBS, Life Technologies) containing Dulbecco's Modified Eagle's Medium (DMEM, Sigma) supplemented with penicillin and streptomycin (Corning) at 37° C. in humidified 5% CO2. Before M1 and M2 stimuli (IFNγ 10 ng/ml and IL-4 10 ng/ml, respectively), cells were starved for 24 hours with 0.1% FBS-containing media. THP-1 was also purchased from ATCC and maintained in Roswell Park Memorial Institute (RPMI) 1640 medium in 10% FBS with penicillin and streptomycin at 37° C. in humidified 5% CO2. The macrophage-like state was obtained by treating the THP-1 monocytes for 48 hours with PMA (200 ng/ml, Sigma). *Mycoplasma* contamination test was routinely performed (once a month).

Primary Cells

Mouse Peritoneal Macrophages.

Peritoneal macrophages were obtained 4 days after intra peritoneal injection of 2.5-3 ml of 4% thioglycollate (Fisher Scientific) and $5\times10^5$ cells were cultured on 24-well plates (Corning) with RPMI containing 10% FBS. Nonadherent cells were discarded after 16 hours. After washing with PBS, cells were incubated with M1 or M2 stimuli (IFNγ 10 ng/ml and IL-4 10 ng/ml, respectively) for 24 hours until harvesting.

Mouse Bone Marrow Macrophages.

Bone marrow-derived macrophages (BMDM) were isolated and differentiated as described previously(47). Briefly, whole bone marrow cells were harvested from femurs of PARP14$^{-/-}$ males 10-12 weeks old or from age and sex-matched control wild type mice (C57BL/6 mice, Jackson Laboratory) under aseptic conditions and cultured in RPMI 1640 (Lonza) supplemented with 10% FBS, penicillin and streptomycin (Corning) in presence of M-CSF (50 ng/ml) (Peprotech) at 37° C. in humidified 5% $CO_2$. After 7 days culture, cells were incubated with M1 or M2 stimuli (IFNγ 10 ng/ml and IL-4 10 ng/ml, respectively) for 24 hours until harvesting.

Isolation of CD14+ Human Peripheral Blood Mononuclear Cells (PBMC)

Peripheral blood mononuclear cells (PBMC) were isolated from buffy coat using lymphocyte separation medium (LSM, MP Biomedicals). After isolation of PBMCs, CD14+ cells were isolated by Dynabeads in combination with anti CD14 antibody (Dynabeads FlowComp human CD14, Invitrogen), according to the manufacturer's instruction. Briefly, CD14+ dynabeads-bound cells (CD14+ cells) were isolated using a magnet. After releasing Dynabeads from cells, beads-free CD14+ PBMCs ($5 \times 10^5$ cells) were cultured in 24 well-dish plates with 0.5 ml of RPMI supplemented with 10% FBS at 37° C. in 5% $CO_2$.

Immunohistochemistry/Immunofluorescence

Samples were cut into 7 μm thin slices, and cryo-sections were fixed in acetone. After blocking in 4% of appropriate serum, sections were incubated with primary antibodies (Mac3 (1:200, M3/84, BD Pharmingen), PARP14 (1:50, HPA01206 Sigma-Aldrich), PARP9 (1:100, ab53796, Abcam), and human CD68 (1:200, M0876, Dako)), followed by biotin-labeled secondary antibody (Vector Laboratories, Burlingame, Calif., USA) and streptavidin-coupled Alexa Fluor 488 antibody (Life Technologies). For immunofluorescence double labeling, after avidin/biotin blocking (Vector Laboratories), the second primary antibody was applied overnight at 4° C., followed by biotin-labeled secondary antibody and streptavidin-coupled Alexa Fluor 594 antibody (Life Technologies). Sections were washed in PBS and embedded in mounting medium containing DAPI (Vector Laboratories). For bright field immunohistochemistry on tissue sections, following the first biotin-labeled secondary antibody incubation, sections were incubated with streptavidin-labeled HRP solution (Dako), followed by AEC solution. Slides were examined using the Eclipse 80i microscope (Nikon, Melville, N.Y., USA) or the confocal microscope A1 (Nikon). All images were processed with Elements 3.20 software (Nikon).

Human Tissue and Counting PARP14/PARP9 Positive Macrophages

Atherosclerotic carotid arteries (n=10) were collected from patients undergoing endarterectomy procedures at Brigham and Women's Hospital according to IRB protocol #1999P001348 (PL). Informed consent was not necessary, because all samples are considered as "discarded material." Samples have two groups, such as macrophage-rich ("unstable", n=5) and no macrophage-rich ("stable", n=5) plaques, respectively. Samples were embedded in OCT compound and stored at −80° C. until use. In three different fields of each sample (n=5), 200 cells (nuclei) with CD68 positive cells were evaluated whether they express PARP14 and/or PARP9 (600 cells per sample). The quantification of immunofluorescence was performed by examiners who were blinded to group allocation (unstable vs. stable plaque).

Animal Procedure, PARP14-Deficient (PARP14−/−) Mice, Wire-Induced Vascular Injury, and Evaluation of Neointima Hyperplasia PARP14-deficient (PARP14$^{-/-}$) male mice(25, 48) and age-matched wild type (PARP14$^{+/+}$) male mice were subjected to vascular injury. Transluminal arterial injury was induced as previously described(49) for 10 week-old-mice by inserting a straight spring wire (0.38 mm in diameter, C-SF-15-15, Cook) into the femoral artery under microscopic observation (Leica M80). Two weeks after injury, to collect arterial samples, mice were euthanized by intraperitoneal administration of an overdose of Pentobarbital and then perfused with 0.9% NaCl solution at a constant pressure via the left ventricle(50). The collected tissue was embedded in O.C.T. compound (Tissue-Tek) and then frozen in liquid nitrogen and stored at −80° C. until further use. The Institutional Animal Care and Use Committee at Beth Israel Deaconess Medical Center approved all procedures (protocol #017-2010). Intima and media area and their ratio of injured femoral arteries were measured by manual tracing in at least three sections of three different levels with 100 μm interval in each animal (n=5), using Elements 3.20 software (Nikon). The quantification of histology and immunohistochemistry were performed by examiners who were blinded to group allocation (PARP14+/+ vs. PARP14−/−). No randomization method was used.

RNA Interference of PARP14 and PARP14

RNA silencing was performed as described previously (51). Briefly, 20 nmol/l siRNA against PARP14 (L-023583 for human cells, L-160447 for mouse cells) and PARP9 (L-014734 for human cells, L-05024901 for mouse cells)(all ONTARGETplus SMART-pool, Thermo Scientific) or non-targeting siRNA (scramble control siRNA, ON-TARGET Non-Targeting Pool, Thermo Scientific) was transferred into macrophages using SilenceMag (BOCA Scientific, Boca Raton, Fla.), according to the manufacture's instruction. Target sequences of siRNA pool were follows:

Human PARP14:

UAAUCAAAGGUCUCUUAUG, (SEQ ID NO: 29)

UAAUGCUUAAGGUCCUCAU, (SEQ ID NO: 30)

UCAUUAUACUGCCAUUCUA (SEQ ID NO: 31)
and

GAACUCUUGACAUCAUUUC; (SEQ ID NO: 32)

Human PARP9:

AAUUACAUCUGCCGUCUGC, (SEQ ID NO: 33)

UUUGUGGCAAGAAAUUCCG, (SEQ ID NO: 34)

UUAAUCAACAGGGCUGCCA (SEQ ID NO: 35)
and

UACAGCCAAACUUAUUCUG; (SEQ ID NO: 36)

Mouse PARP14:

CUUGAAAGCUUUACGUAUA, (SEQ ID NO: 37)

-continued

CAGCAAUAGGAACGGGAAA, (SEQ ID NO: 38)

CCAAAGAACUUGAUCAACA (SEQ ID NO: 39)
and

CGUAGUAGCAAAAGCGAUA; (SEQ ID NO: 40)

Mouse PARP9:

ACACAAUGUCUUCGAAAUU, (SEQ ID NO: 41)

CCAGACAGCUAUCGAAUUA, (SEQ ID NO: 42)

CCAAAUAUGAUCUACGCAU (SEQ ID NO: 43)
and

CGUACACAUUUCAACGAUA; (SEQ ID NO: 44)

Control scramble:

UGGUUUACAUGUCGACUAA, (SEQ ID NO: 45)

UGGUUUACAUGUUGUGUGA, (SEQ ID NO: 46)

UGGUUUACAUGUUUUCUGA (SEQ ID NO: 47)
and

UGGUUUACAUGUUUUCCUA. (SEQ ID NO: 48)

Cell Proliferation (MTS), Cell Viability, and Apoptosis

Cell proliferation, viability, and apoptosis were assessed by CellTiter 96 AQueous Nonradioactive Cell Proliferation Assay Kit (MTS), Cell Titer Blue assay, and Apo-ONE Homogeneous Caspase-3/7 Assay Kit, respectively (Promega), according to the manufacturer's instructions.

RNA Preparation and Real-Time PCR

Total RNA from the cell culture was isolated using TriZol (Life Technologies), and reverse transcription was performed using the QuantiTect Reverse Transcription Kit (Qiagen, Hilden, Germany). The mRNA expression was determined by TaqMan-based real-time PCR reactions (Life Technologies). The following TaqMan probes were used: Hs99999902_m1 (human RPLP0), Mm00725448_s1 (mouse RPLP0), Hs00981511_m1 (human PARP14), Mm00520984_m1 (mouse PARP14), Hs00967084_m1 (human PARP9), Mm00518778_m1 (mouse PARP9), Hs00174128_m1 (human TNF), Mm00443258_m1 (mouse TNF), Hs00174097_m1 (human IL-113), Mm01336189_m1 (mouse IL1β) Mm00475988_m1 (mouse ARG1), Hs00267207_m1 (human MRC1), Mm00485148_m1 (mouse MRC1), Mm00440502_m1 (mouse NOS2) and Hs00234140_m1 (human CCL2). The expression levels were normalized to RPLP0. Results were calculated using the Delta-Delta Ct method, and presented as arbitrary unit.

Laser Capture Microdissection (LCM) and RNA Amplification

LCM was performed on the Leica LMD6500 Microdissection System. Neointima were cut using the following LCM parameters: power, 50 mW; pulse duration, 2 ms; and spot size, 20 Hm. RNA was isolated using using the PicoPure RNA Isoaltion Kit, followed by RNA amplification using the RiboAmp HS Plus RNA Amplification Kit (both Arcturus, Mountain View, Calif., USA), according to the manufacturer's protocol. PCR array was performed using the Fluidigm PCR system.

Western Blot Analysis

Cells were lysed with RIPA buffer containing protease inhibitor (Roche). Protein concentration was measured using the bicinchoninic acid (BCA) method (Thermo Scientific). Total protein was separated by 8-10% SDS-PAGE and transferred using the iBlot Western blotting system (Life Technologies). Primary antibodies against human and mouse PARP14 (1:250, HPA01206 Sigma-Aldrich), human and mouse PARP9 (1:250, ab53796, Abcam), human and mouse STAT1 (1:1000, #9172, cell signaling), phosphorylated STAT1 (1:1000, #9167, cell signaling), human and mouse STAT6 (1:2000, #9362, cell signaling), mouse (1:1000, ab54461, Abcam) and human (1:2000, #9361, cell signaling) phosphorylated STAT6, and human and mouse β-actin (1:5000; Novus) were used. Protein expression was detected using Pierce ECL Western Blotting substrate Reagent (Thermo Scientific) and ImageQuant LAS 4000 (GE Healthcare).

ELISA

The amounts of TNFα and IL-1β released into the culture media after stimulation were measured by an ELISA kit following manufacture instructions (Duoset Kit, R&D). The culture medium of unstimulated macrophage was used as the negative control. Standard, control, or sample solution was added to the ELISA well plate, which had been pre-coated with specific monoclonal capture antibody. After being shaken gently for 3 hours at room temperature, the polyclonal anti-TNFα antibody, conjugated with horseradish peroxidase, was added to the solution and incubated for 1 hour at room temperature. A substrate solution containing hydrogen peroxidase and chromogen was added and allowed to react for 20 minutes. The levels of cytokines were assessed by a plate reader at 450 nm and normalized with the abundance of standard solution.

Nitrate Quantification

To quantify nitric oxide in cell culture media of macrophages, mimicking iNOS concentration, Greiss Reagent Kit (G-7921, Life technologies) was used.

Co-Immunoprecipitation

Cells were lysed in immunoprecipitation (IP) lysis buffer (Thermo Scientific). 100 μg of protein was incubated with PARP14 antibody (5 μg, Invitrogen) and Dynabeads streptavidin (Life Technologies) by rotation overnight at 4° C. followed by washing 3 times with PBS/Tween 20 (0.02%), using a magnet to collect the beads after each wash. 5% of the precipitated protein sample was subjected to SDS-PAGE. Protein expression was detected using Pierce ECL Western blotting substrate Reagent and ImageQuant LAS 4000.

Ribosylation Assay

Recombinant human PARP14 and PARP9 (BPS Bioscience Inc.) proteins, and BSA (Sigma-Aldrich) were incubated with recombinant human STAT1α (OriGene Technologies, Inc.) or STAT6 protein (Sino Biological Inc.) at a final concentration of 5 ng/μl in the presence of 100 μM β-Nicotinamide adenine dinucleotide hydrate (NAD; Sigma-Aldrich) or 6-biotin-17-NAD (Trevigen, Inc.) in 50 mM Tris-HCl buffer (pH 7.4) for 1 hour at room temperature. Ribosylation of STAT1α and STAT6 was detected by LC-MS/MS after trypsin digestion or Western blotting using Streptavidin-HRP (Abcam) after SDS-PAGE. Quantification of the relative abundances of ribosylated STAT1α peptides was completed by calculating the area under the curve (AUC) of the extracted ion chromatograms (XICs) of the monoisotopic peaks of the modified versus unmodified peptides. The ratios were reported as AUC mod./(AUC mod.+AUC unmod).

Single Cell Gene Expression Analysis

For single cell analysis of CD14+ PBMCs derived from two donors, cell capture and target preamplification were performed using C1 system (Fluidigm), according to the manufacturer's instructions. Quantitative real-time PCR was performed using the BioMark 96.96 Dynamic Array platform (Fluidgm) (37). After isolation of CD14+ PBMCs from buffy coat, cells were cultured for 10 days. Cells in M0 condition were harvested on day 10 and M1 cells were harvested on day 11 after 24 hours incubation with IFNγ 10 ng/ml. Cell capture rate by C1 chip was 89.6% (86/96) in M0 and 83.3% (84/96) in M1 of Donor 1, 96.9% (93/96) in M0, 89.6% (86/96) in M1 of Donor 2 and 93.8% (90/96) in M0 and 84.3% (81/96) of Donor3. Delta-Delta Ct values of target genes in each cell were calculated by using RPLP0/GAPDH gene expression. Delta-Delta CT scores for each gene were stored as a matrix of cells vs genes. Each cell was assigned a numeric ID ranging from 1 to n, where n is total cell count. Delta-Delta CT scores are derived from direct gene measurement normalized against a house-keeping gene (GAPDH and RPLP0).

As quality control over the single cell analysis, the average gene reads across all cells were first broadly compared for Donors 1 and 2 (D1 and D2) in both M0 and M1 conditions, and both normalization factors (GAPDH and RPLP0) were considered. The Pearson correlation between all conditions was measured and represented in an ordered similarity matrix. Here, the normalization factors appeared stable, with the exception of D2 M1. Additionally, overall it was found that D2 M1 appeared inconsistent from the other conditions as well, forming a distinct separate branch from D1 M1. Thus, D2 was excluded from the analysis. To understand whether the M0 condition cells were synchronized, i.e., they exist as a homogeneous population, the same analysis was performed and the Pearson correlation score was considered for all pairwise comparisons between cells. The same procedure was performed to observe for subpopulations in the M1 phase. In order to observe gene-wise correlations across samples, the cell-gene matrix was transposed, and the Pearson similarity score calculated for each gene, across all the cell observations.

Statistical Analysis

Data are given as mean±SD. And, "n" indicates the number of independent experiments or number of animals/samples. Tests with a P value less than 0.05 were considered statistically significant. Pairwise group comparisons were performed using a Student's t test (GraphPad prism 5, Prism Software Inc. (La Jolla, Calif.)). If F test showed the variance was significantly different, unpaired t test with Welch's correction was performed. Exclusion criteria were set by Grubbs' test. No statistical method was used to predetermine sample size. The experiments were not randomized.

Results

Figure 1B:
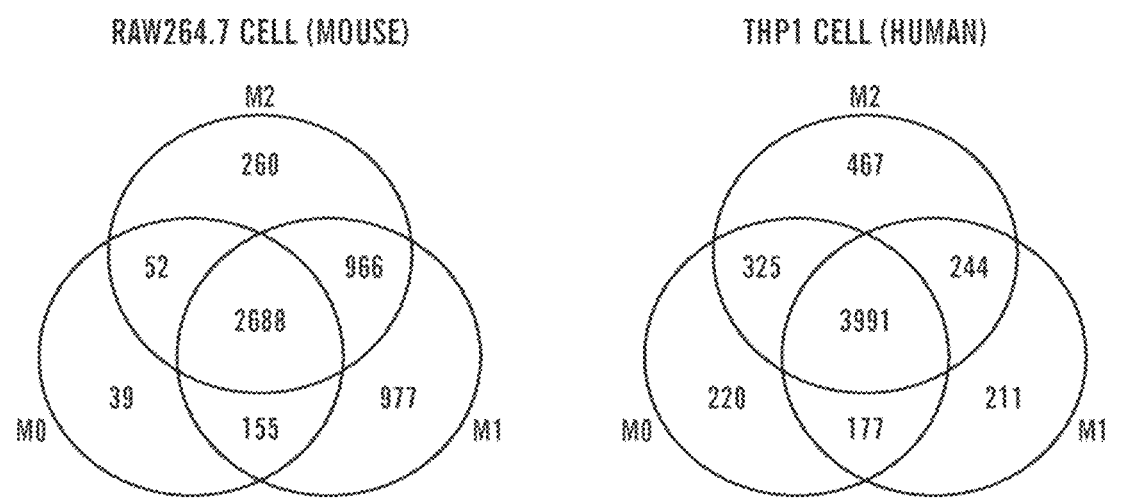
FIG. 1B shows the Venn diagrams of quantified proteins (2 or more peptides) from mouse RAW264.7 and human THP-1 cells in M0 (unstimulated), M1 (IFNγ-stimulated) and M2 (IL-4-stimulated) conditions. 5137 proteins in RAW264.7 cells and 5635 in THP1 were identified. 2688 proteins in RAW264.7 and 3991 in THP1 were commonly present in all M0, M1 and M2 conditions.
Figure 1C:
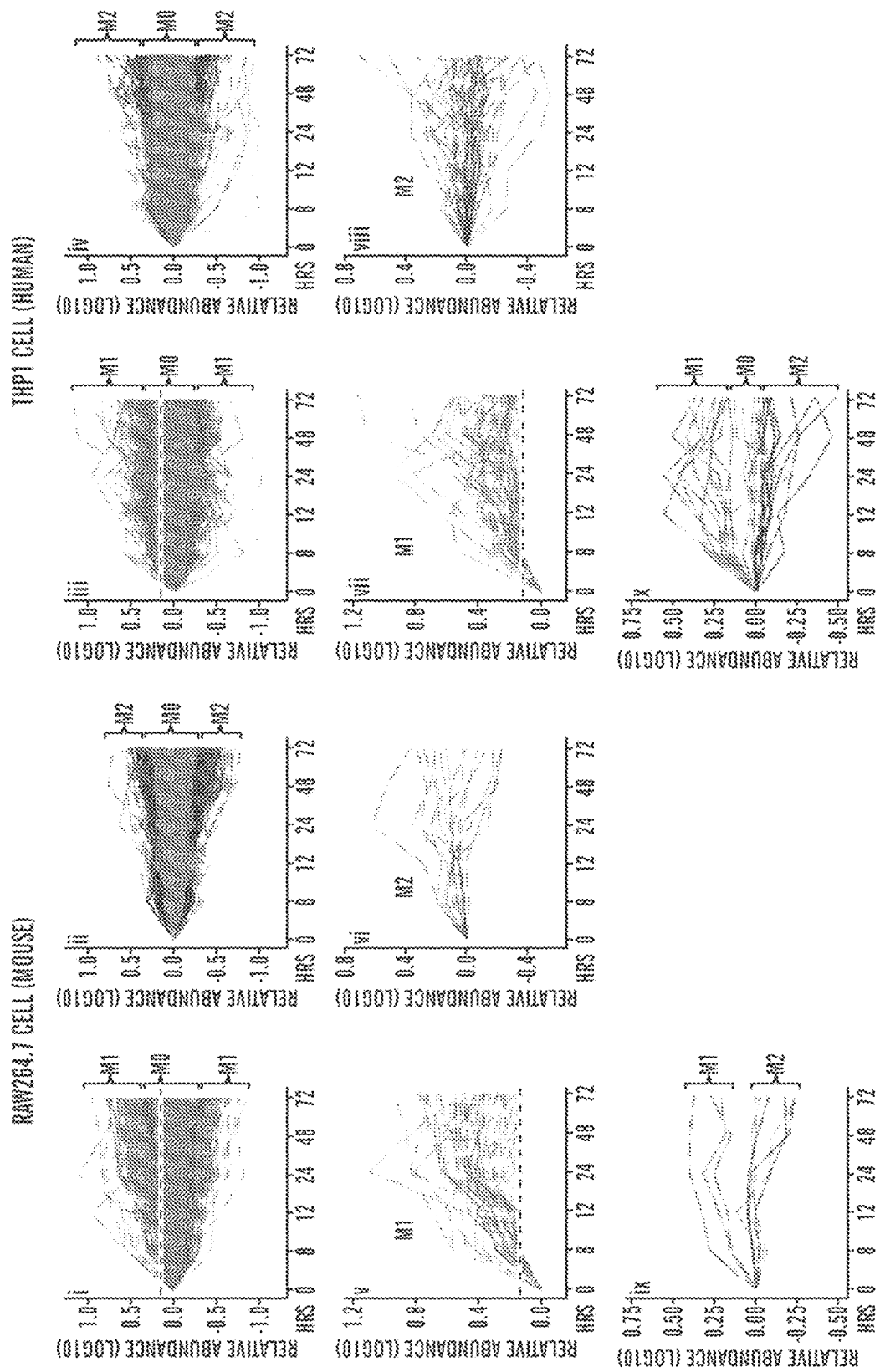
FIG. 1C shows the superimposition of the $\log_{10}$ normalized protein profiles for M0 (light grey traces) versus M1 (dark grey traces) or M2 (black traces) conditions for RAW264.7 (i, ii) and THP-1 experiments (iii, iv). The dashed line indicates the +0.13-established significant threshold (i, iii, v, vii). Extracted profiles of proteins whose abundances exceed the M1 threshold (i) from RAW264.7 (v, vi) and THP-1 (vii, viii) experiments. Extracted protein profiles for proteins increased in M1 over the threshold but decreased in M2 conditions; RAW264.7 (ix) and THP1 (x).

Global Proteomics Identified PARP9 and PARP14 as Candidates for Key Molecules in Macrophage Polarization An in vitro protocol enabled evaluation of polarization of mouse RAW264.7 and human THP-1 cells (FIG. 1A), and application of quantitative proteomics to identify upstream regulators. 5137 and 5635 proteins in RAW264.7 and THP-1 cells respectively were quantified, across three conditions: M0 (unstimulated or unpolarized macrophages), M1 (IFNγ) and M2 (IL-4) (FIG. 1B). An overview of the protein intensities across the three conditions revealed that the distribution of protein expression levels for each M1 and M2 condition exceeded the magnitude of M0 in both RAW264.7 and THP-1 cells (FIG. 1C).

Figure 14:
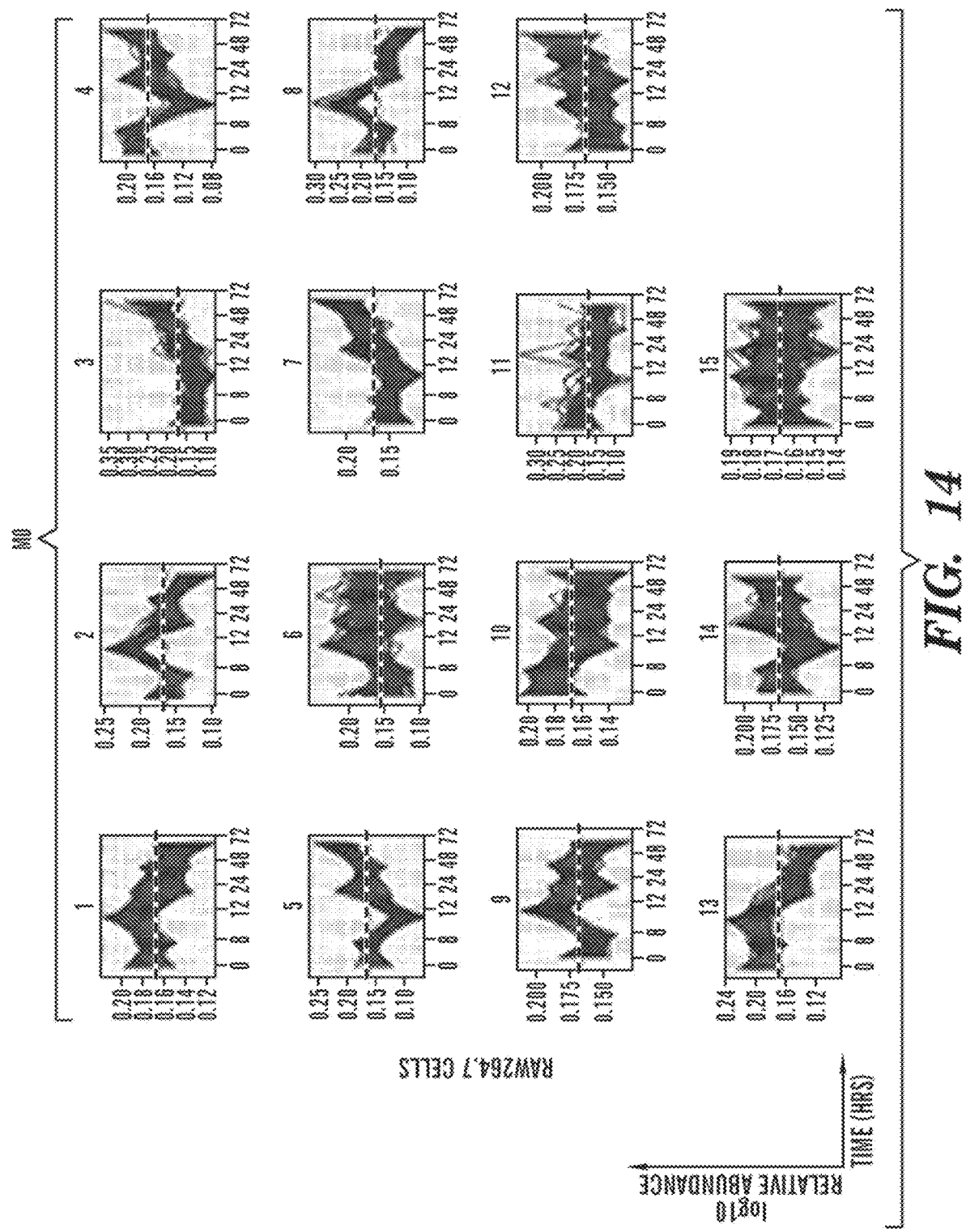
FIG. 14 shows an overview of clustered datasets in RAW264.7 and THP-1 cells. RAW264.7 cell and THP-1 cell Model-based clusters. y-axis—the sum normalized relative abundance; x-axis—the time points after stimulation collected for TMT analysis. The dashed line in each plot indicates the Y=0.16 threshold (i.e., sum-normalized no change).
Figure 14:
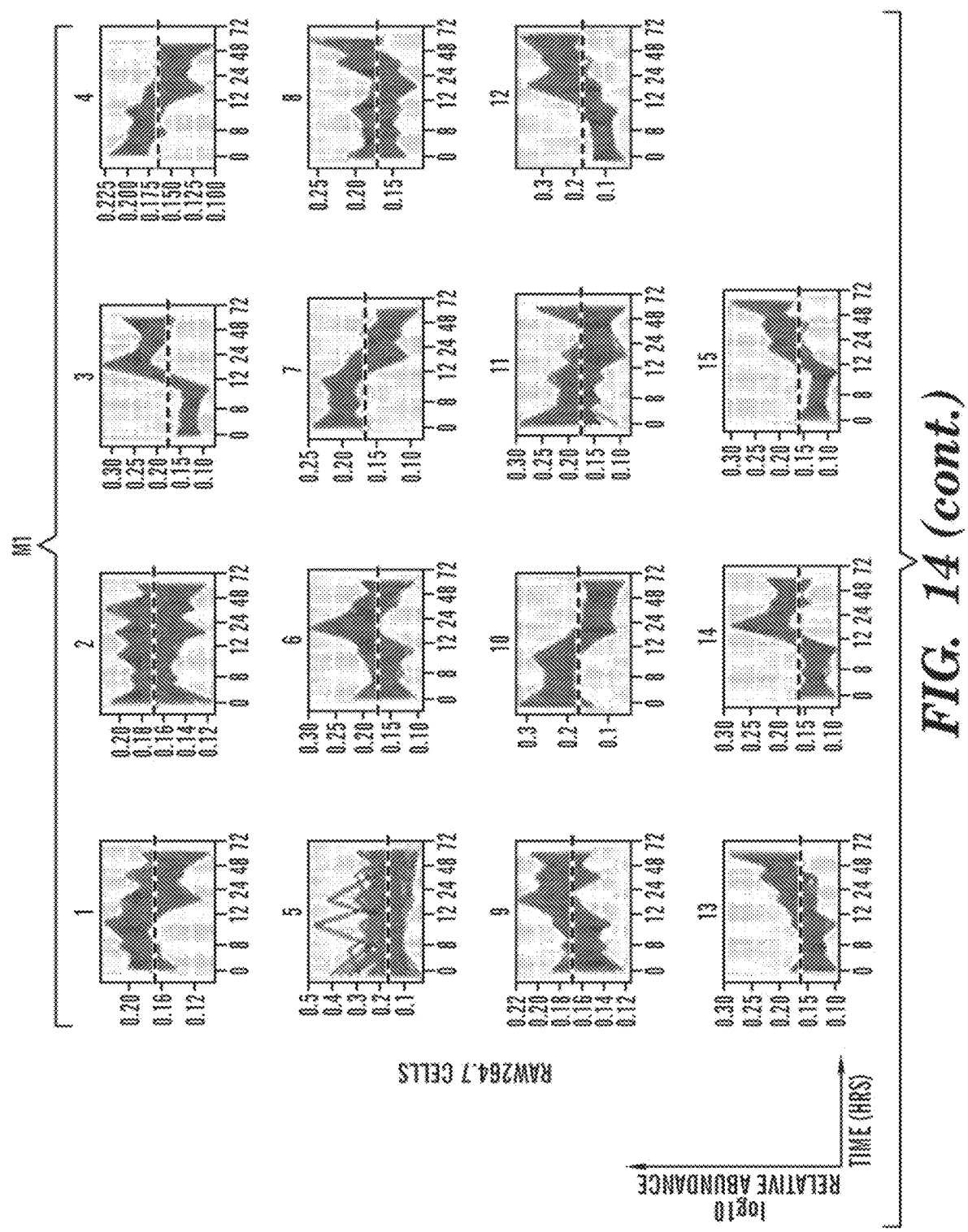
Figure 14:
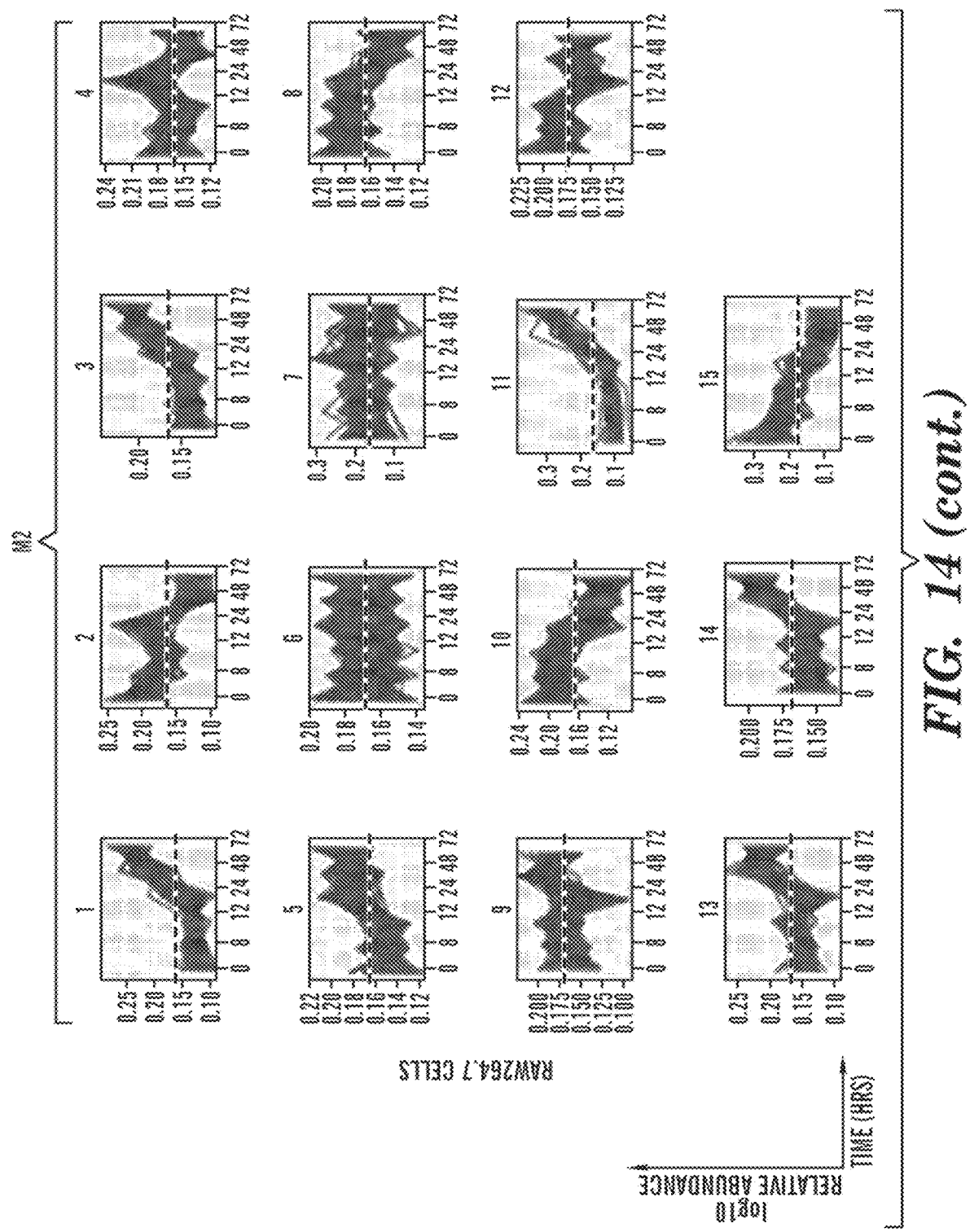
Figure 14:
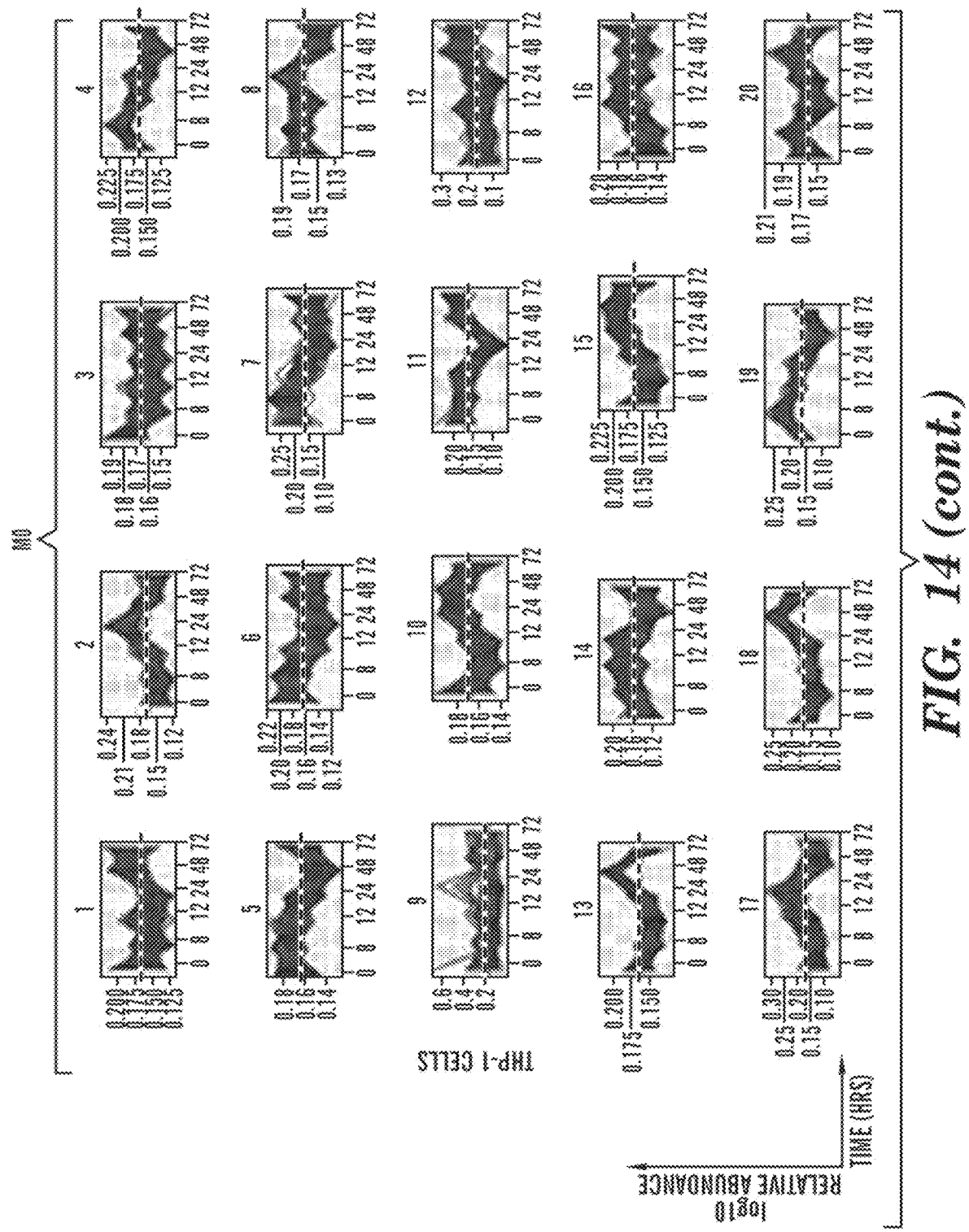
Figure 14:
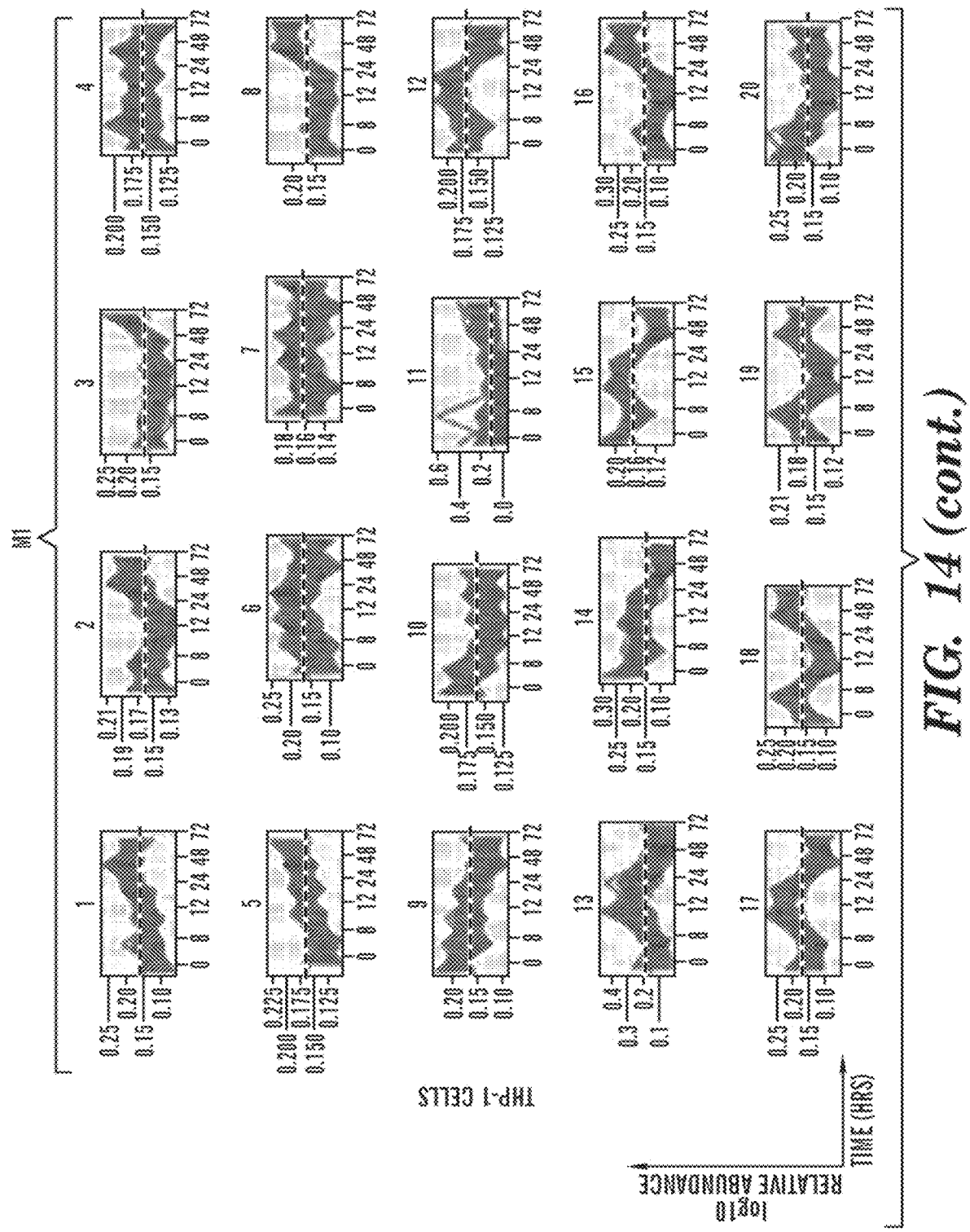
Figure 14:
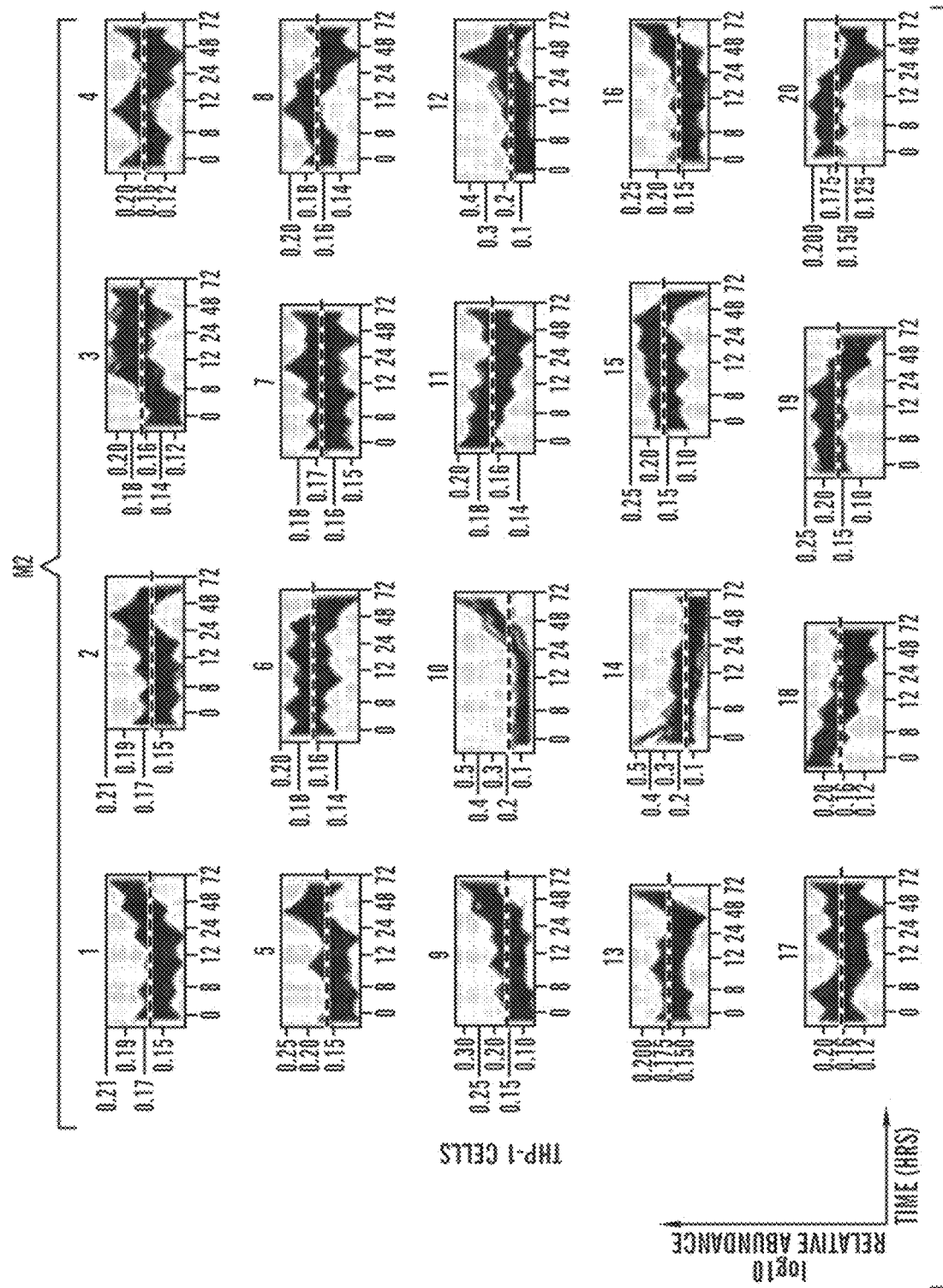

To pursue one class of regulators based on protein abundances, the following criteria were used: 1) an early induction in M1 (within 24 hours) followed by sustained levels until the later time points (up to 72 hours), 2) a decrease in expression in M2, and 3) no significant change in M0. Data filtering and model-based clustering were employed to mine the datasets for proteins with such behaviors. The M0 dataset greatly facilitated data filtering, which permitted a subtraction of the baseline noise (FIG. 1C). M1 protein abundances that surpassed the baseline threshold of 0.13 (~1.24 fold increase) were extracted, while decreasing in M2 (FIG. 1C). Model-based cluster analysis produced 15 and 20 clusters for the RAW264.7 and THP-1 datasets, respectively (FIG. 14). Clusters mined for proteins whose abundances increased in M1 but decreased in M2 with respect to M0 revealed 490 proteins in the RAW264.7 and 414 proteins in the THP-1 datasets fulfilling these criteria (FIG. 7A). Validation of the proteins shared between the human and mouse datasets precipitated a shortened list of 38 candidate proteins (FIG. 7B). Interestingly, both datasets identified PARP9 and PARP14.

Network Analysis Linked PARP9 and PARP14 with Coronary Artery Disease

Figure 8:
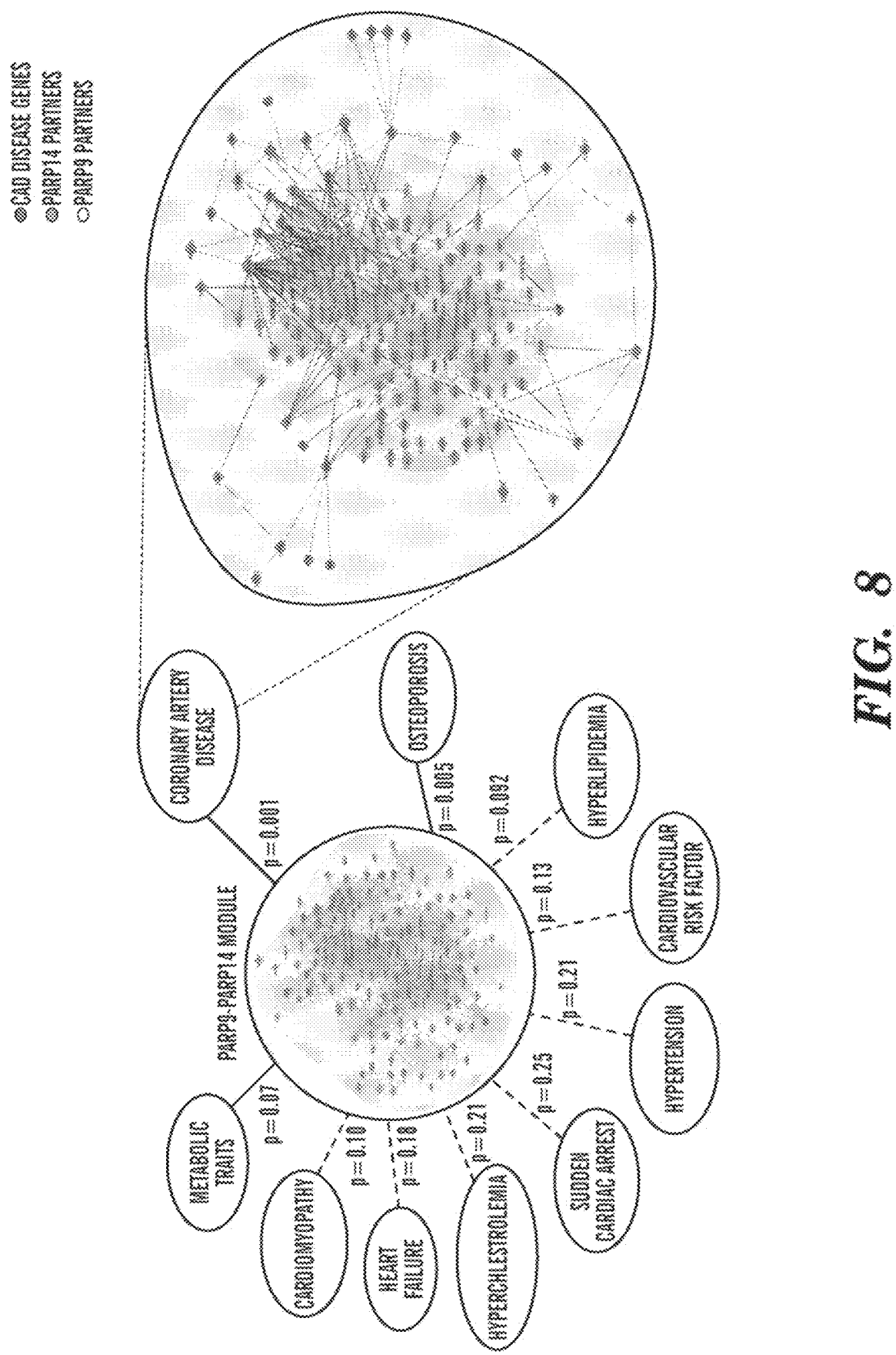
FIG. 8 shows network analysis to predict their association with cardiovascular disease. Left panel: The significance of the closeness of the PARP14-PARP9 first neighbors in the interactome and cardiovascular and metabolic disease modules compared to random expectation are indicated by p-values. The thickness of the lines connecting the modules represents the significance of the reported p-values. Right panel: All shortest paths between PARP9 and PARP14 module and the coronary artery disease (CAD) module. CAD disease genes from genome-wide association study (GWAS) analysis—PLEKHO2 (pleckstrin homology domain containing, family O member 2), LIPA, SH2B3, FN1 (fibronectin 1), HLA-DQB1 (major histocompatibility complex, class II, DQ beta 1) and ABCA1 (member 1 of human transporter sub-family ABCA)—have maximum interactions with PARP14 neighbors than other disease genes.
Figure 15:
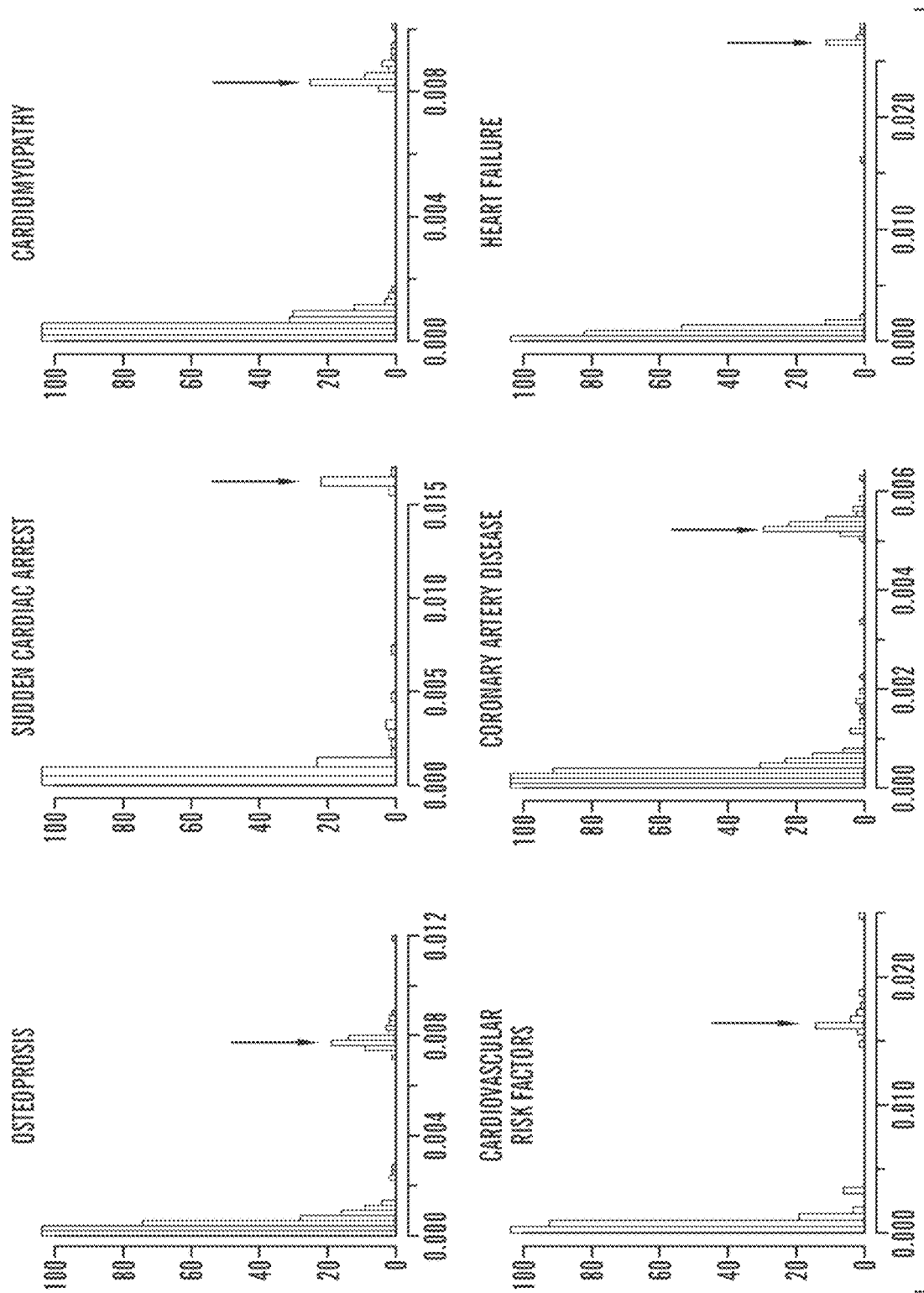
FIG. 15 shows disease modules of cardiovascular and metabolic disorders. X-axis shows the probability that the given genes cluster together in each disease (arrows).
Figure 15:
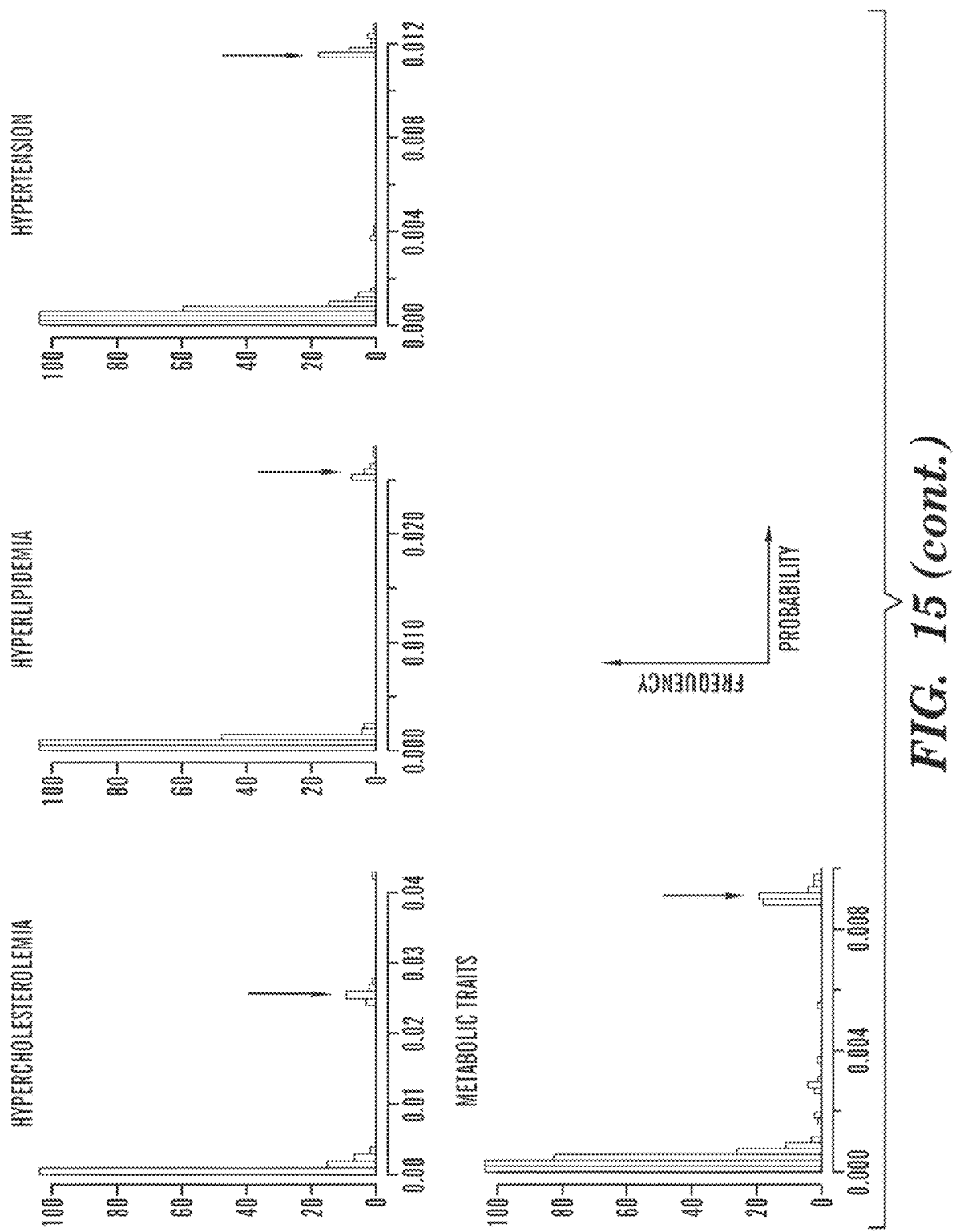

To predict the potential clinical impact of PARP9 and PARP14, a network based-analysis was applied to understand the influence of these genes in a global interaction network ("interactome") (FIG. 8). Recent advancements on molecular interaction network approaches were capitalized on to probe the knowledge for potential interdependency of PARP14 and PARP9 function on various disease modules. Increasing evidence indicates that disease genes are not distributed randomly on the interactome but rather work together in similar biological modules or pathways(29, 30). Moreover, gene products (e.g., proteins) linked to the same phenotype likely interact with each other and cluster in the same network neighborhood(30). Based on these observations, it was postulated that, if PARP9 or PARP14 influences the network neighborhood of a disease, then its immediate neighbors should be close to a disease module compared to random expectation(29, 30). The random-walk method defined a set of genes as a disease module for cardiovascular and metabolic diseases(31) (FIG. 15) using the disease genes from different sources, e.g., Genome-Wide Association Study (GWAS), Online Mendelian Inheritance in Man (OMIM) and MalaCards. The average shortest distance of the immediate neighbors of the PARP9-PARP14 network to the disease module of cardiovascular and metabolic disorders was then measured. Mostly, the interactome describes a set of physical or functional associations between proteins and do not provide the cell or tissue specificity. Thus, in this case, the expression of immediate neighbors in macrophages in public databases was examined and those that were not expressed were removed. It was found that this PARP9-PARP14 network had significantly greater proximity to the coronary artery disease module compared to other cardiovascular and metabolic diseases (FIG. 8). This result indicates the potential major impact of PARP9 and/or PARP14 on the pathogenesis of arterial disease or the onset of its clinical complications.

Figure 2A:
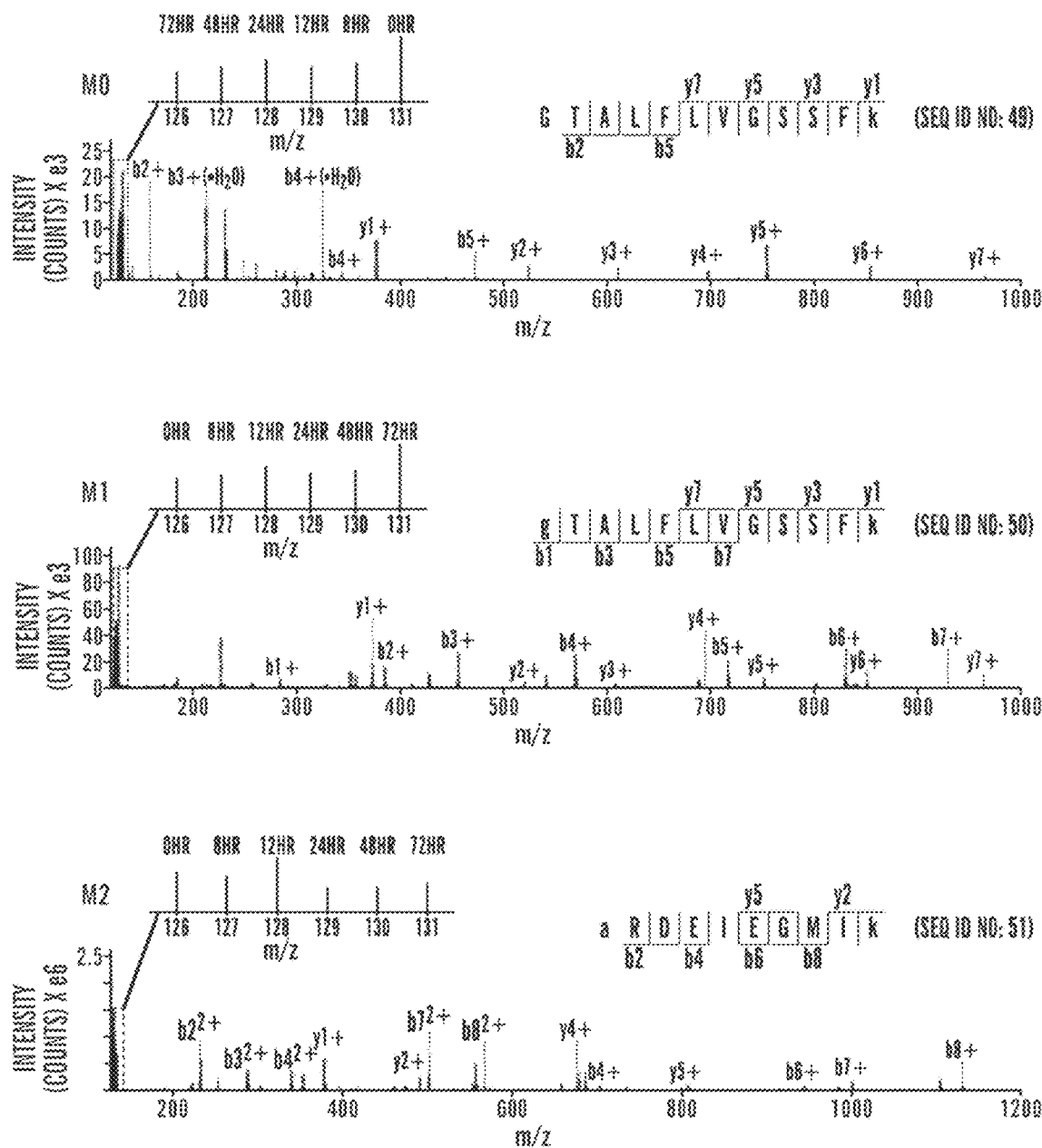
FIGS. 2A-2D show that PARP14 was raised as a possible regulator of macrophage polarization by filtering strategy, including 1) select proteins which are common in all M0, M1 and M2 conditions, 2) select proteins which significantly increase in M1 (>0.13) and decrease in M2 (<0), and 3) select proteins which are common in mouse (RAW264.7) and human (THP-1) macrophage cell lines.
Figure 2B:
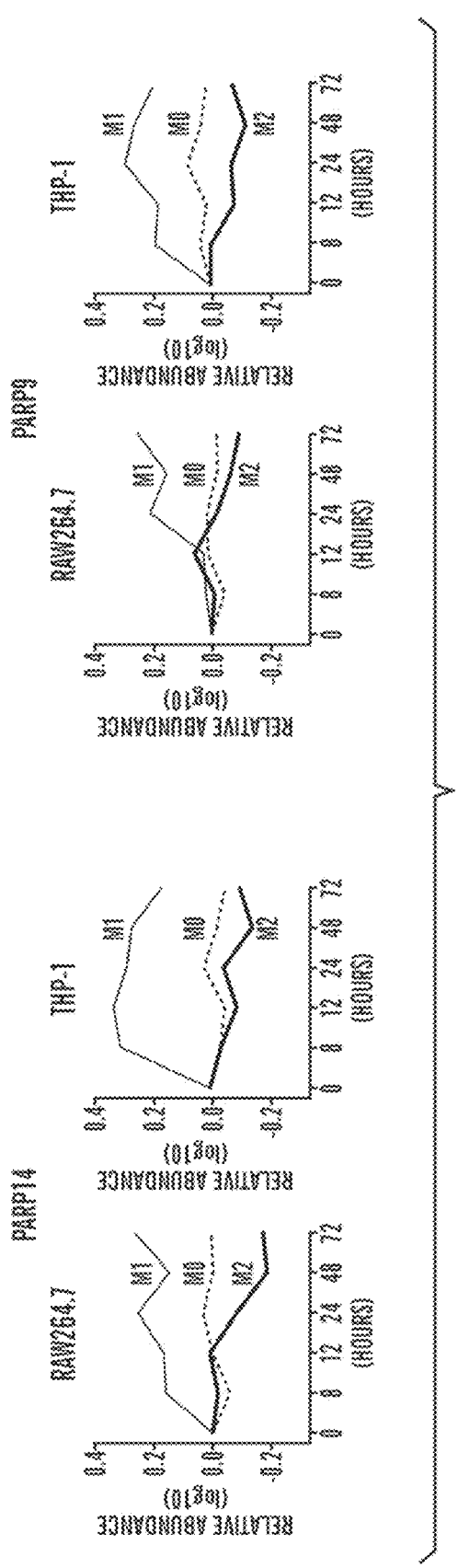
Figure 2D:
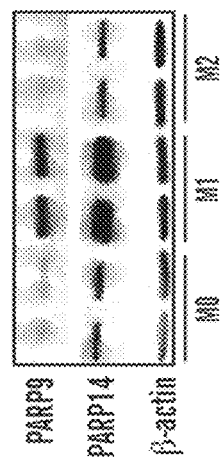
Figure 2C:
Figure 9A:
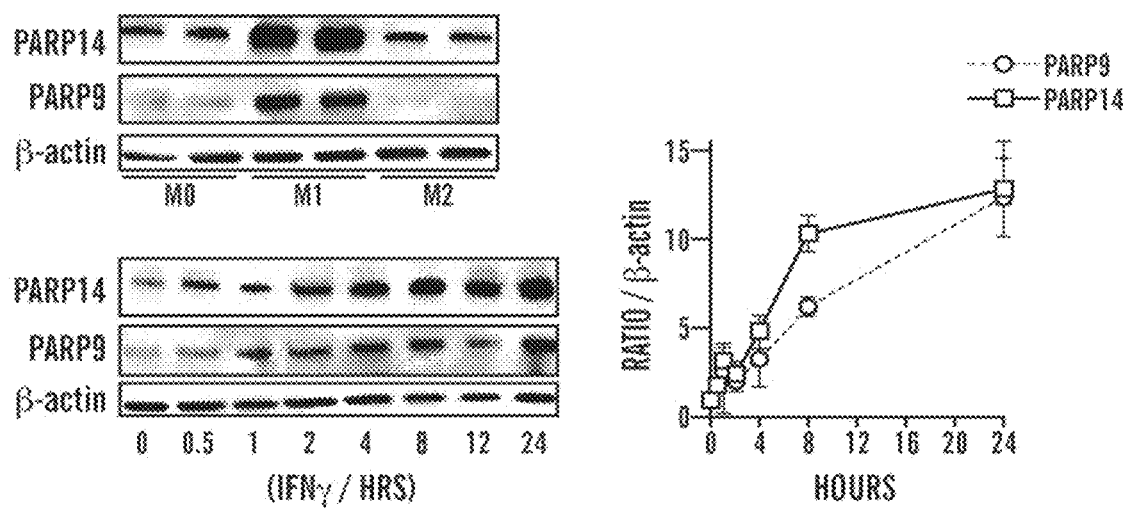
FIGS. 9A-9B show PARP14 and PARP9 expression in vitro and in vivo.
Figure 9B:
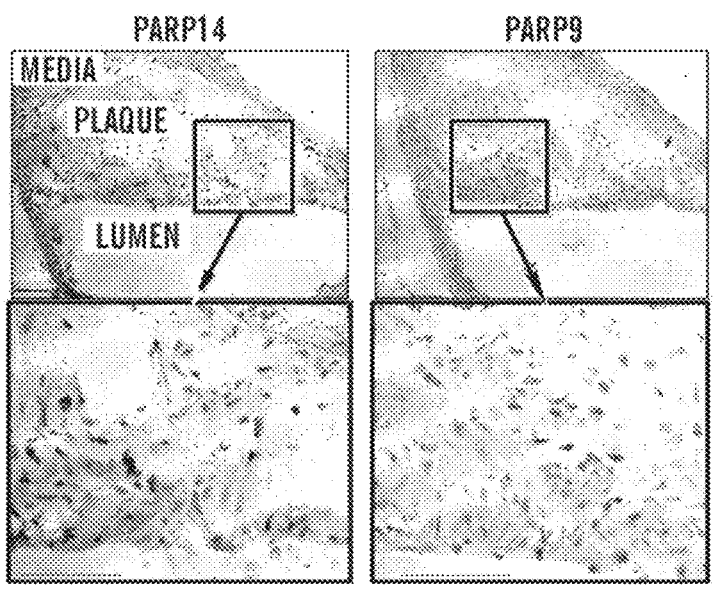
Figure 16:
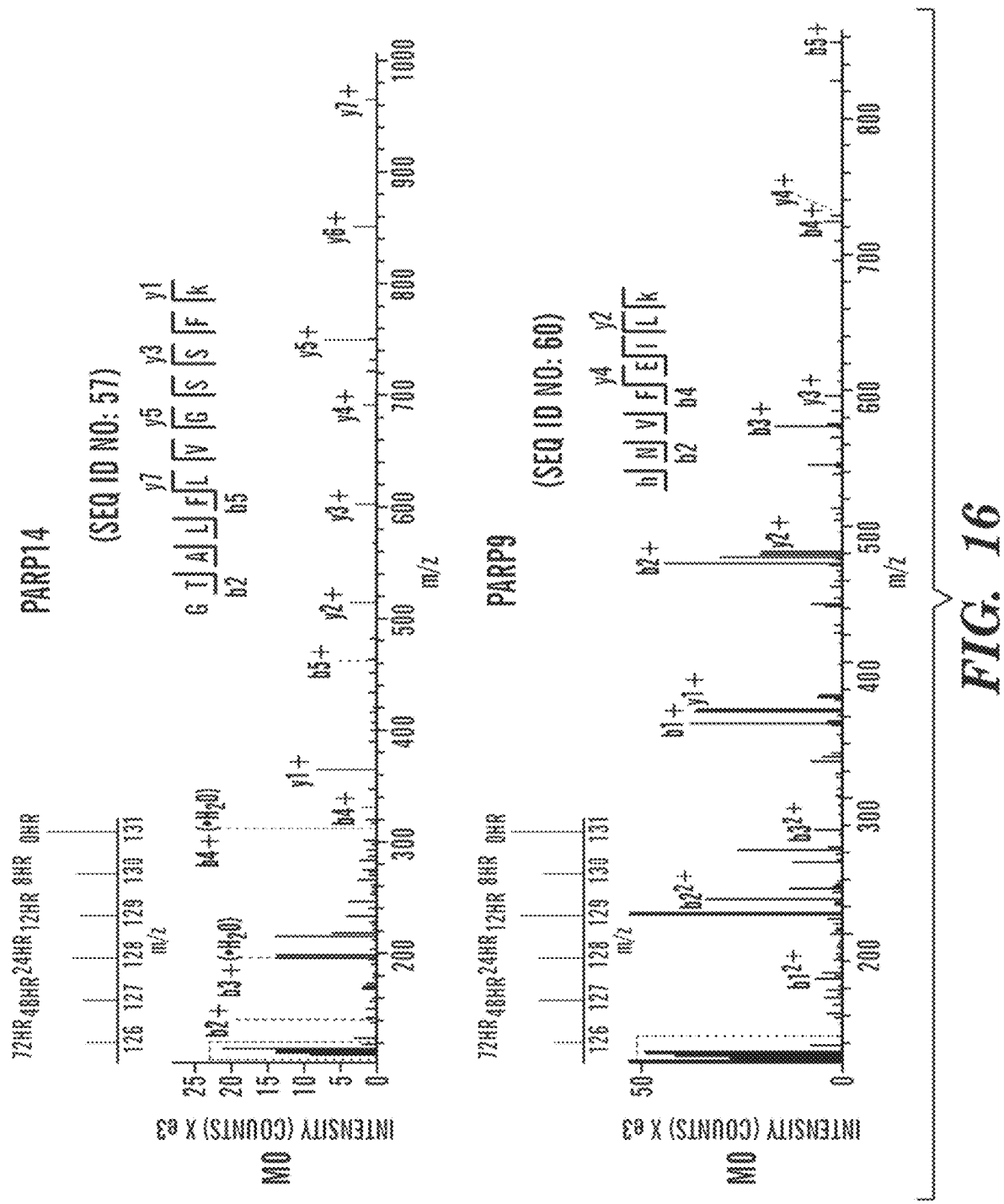
FIG. 16 is a set of example MS/MS spectra for PARP14 and 9 peptides identified in M0, M1 and M2 RAW264.7 cells. The major b and y ions are indicated. The inset contains the TMT reporter ion channels and their corresponding time points. Lower case letters indicate TMT labeled amino acids.
Figure 16:
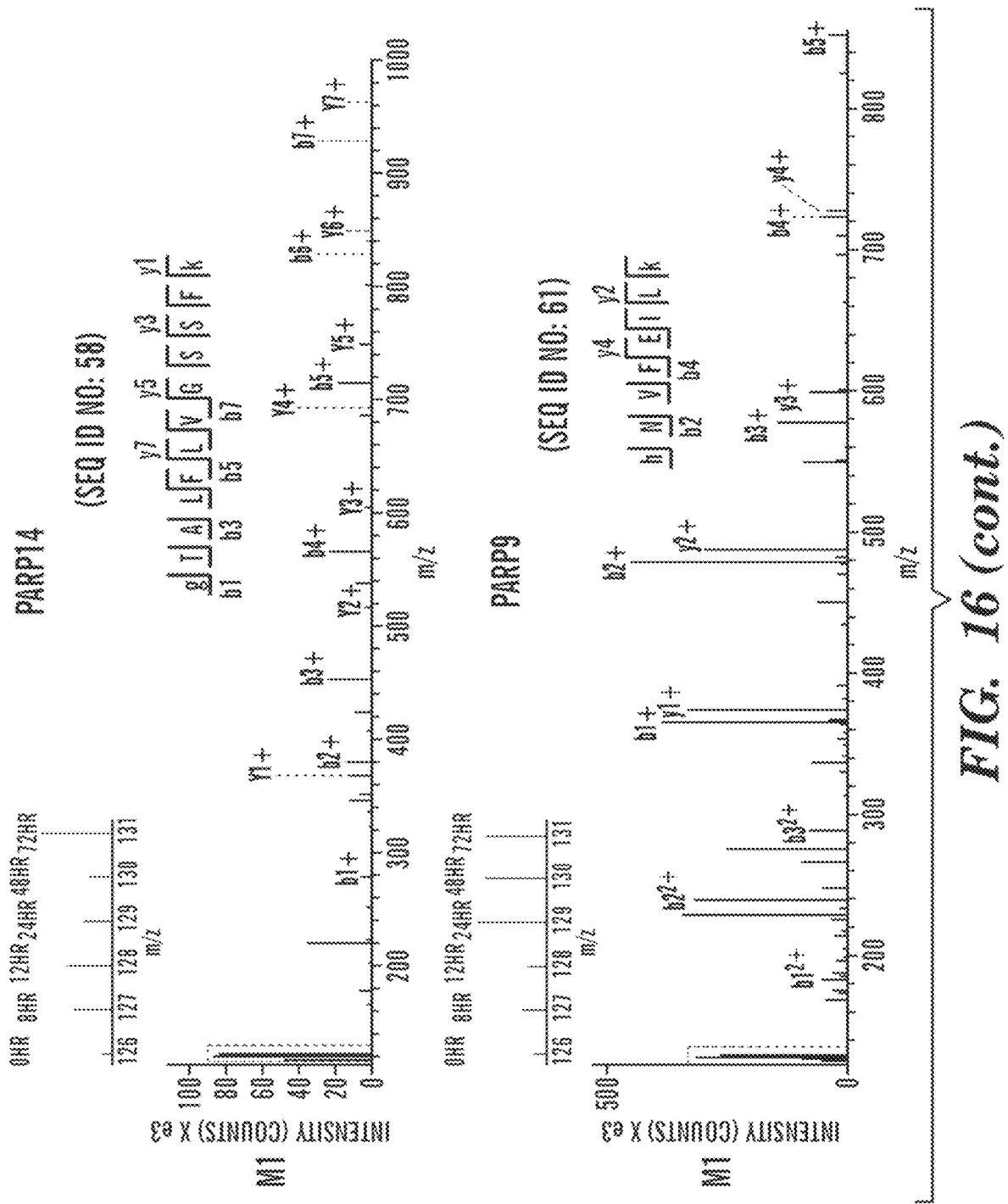
Figure 16:
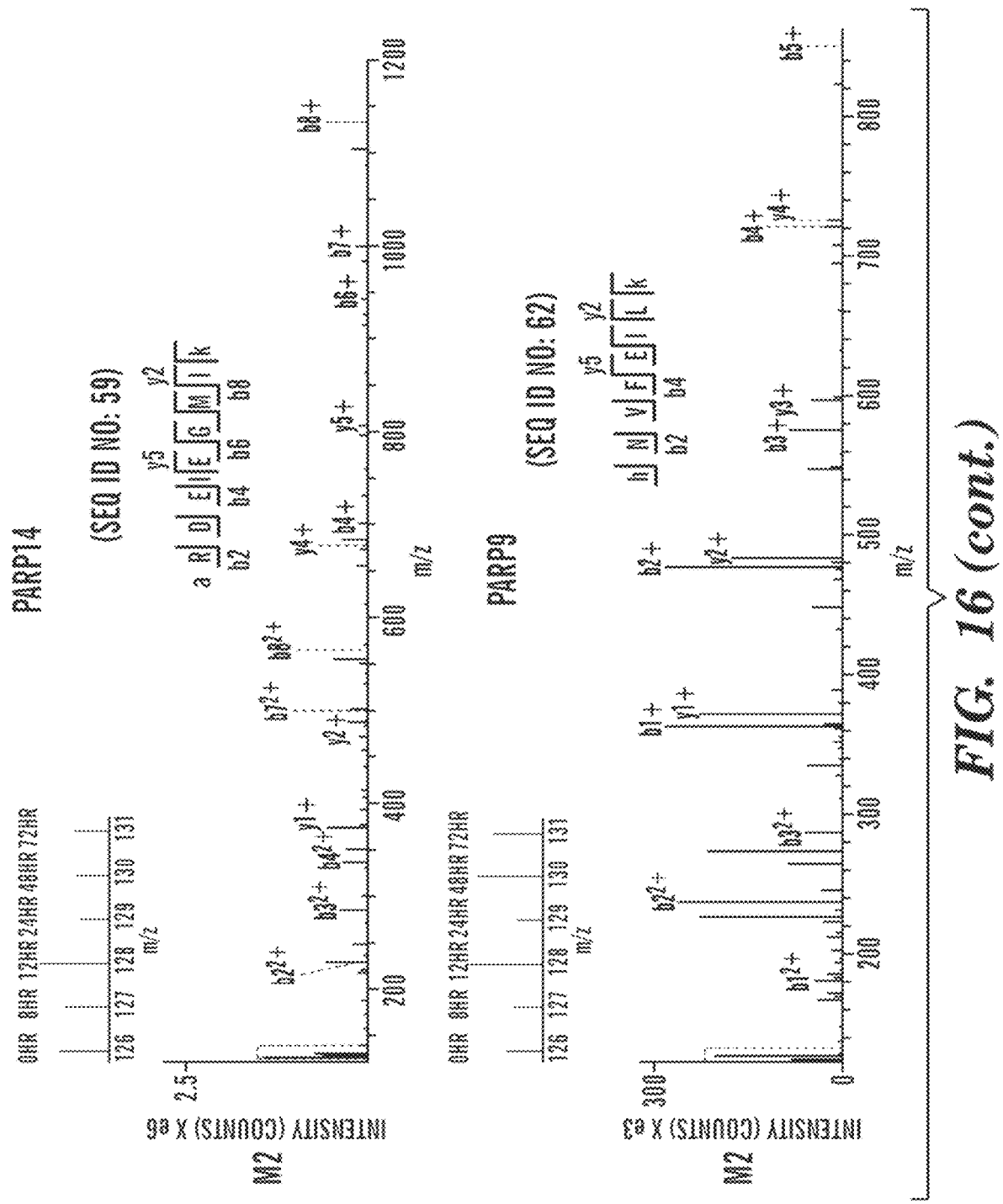
Figure 17:
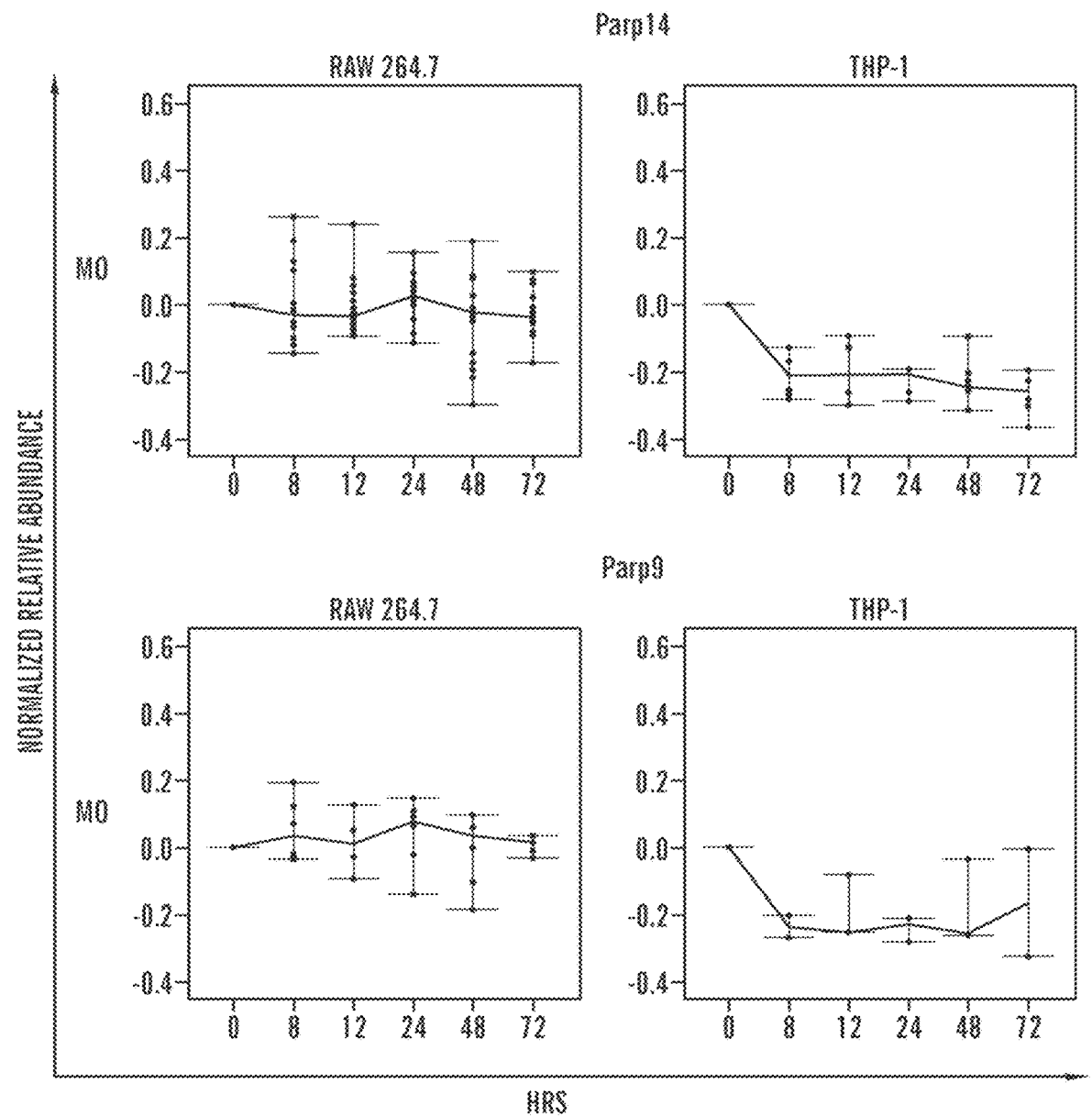
FIG. 17 shows median with relative error bars for the normalized log ratios of all PSMs used in the quantification of PARP14 and PARP9 in RAW264.7 and THP-1 cells in each conditions, M0, M1 and M2.
Figure 17:
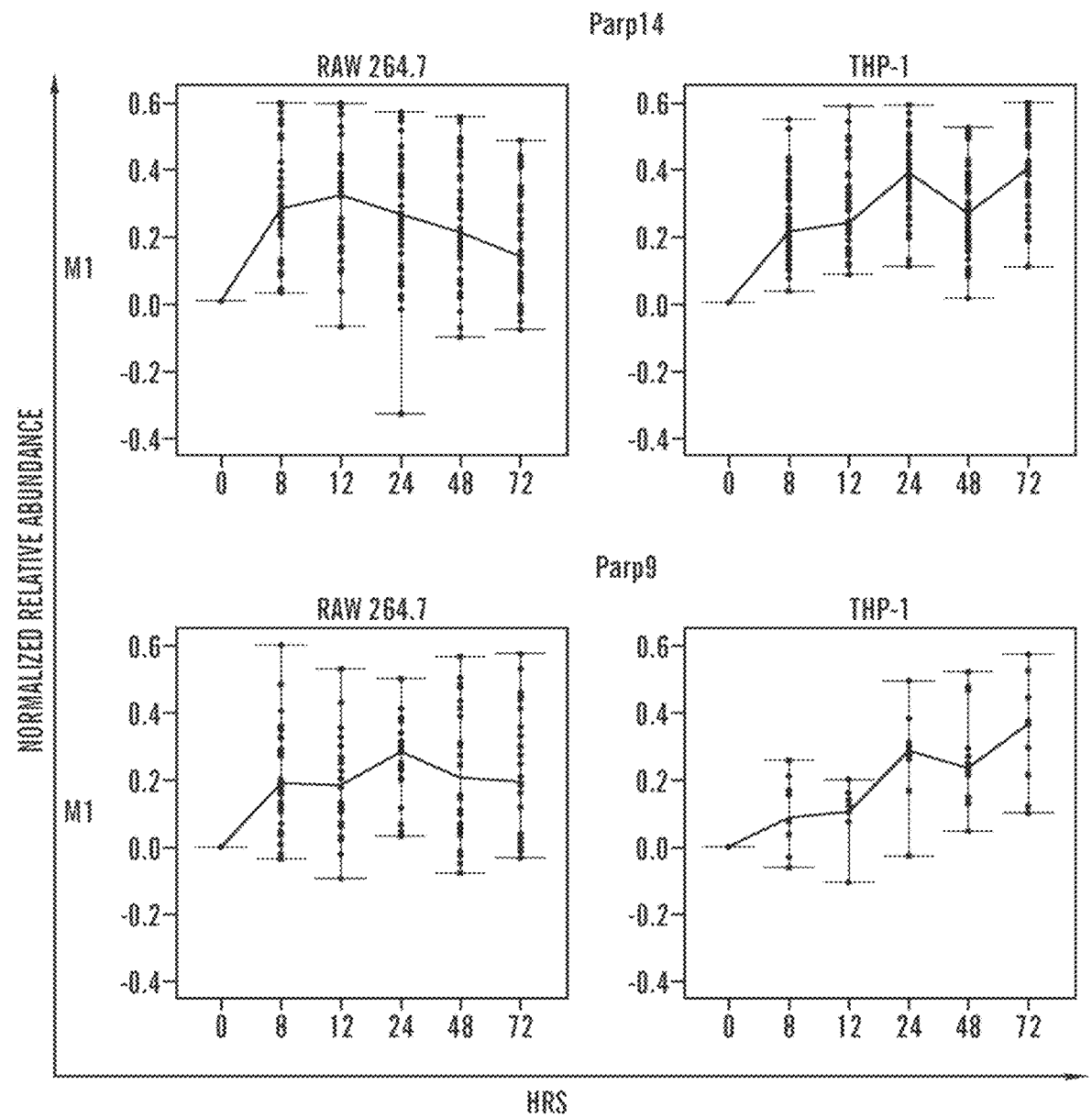
Figure 17:
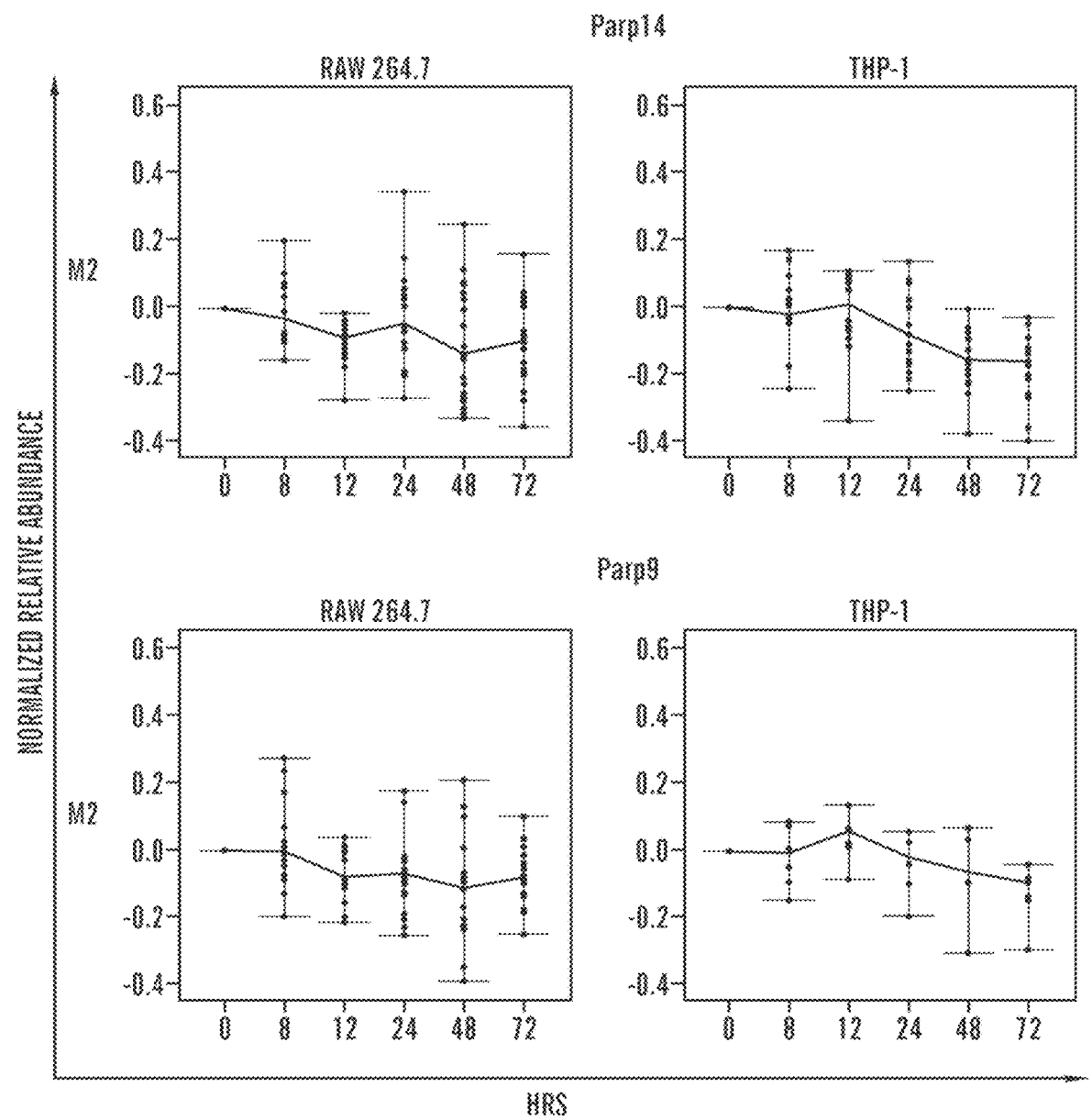

In Vitro Validation: PARP9 is a Pro-Inflammatory Molecule and PARP14 is an Anti-Inflammatory Molecule To test the novel hypothesis that PARP9 and PARP14 regulate macrophage activation and arterial disease and to examine the participation of these proteins in macrophage M1/M2 polarization, a comprehensive in vitro and in vivo approach was used. Consistent with the proteomics data (FIGS. 2B, 16 and 17), mRNA levels of PARP9 and PARP14 increased in M1 and decreased in M2 (FIG. 2C). At protein levels, PARP14 increased earlier than PARP9 upon M1 stimulation (FIG. 9A). Mouse (FIG. 9B) and human (data not shown) atherosclerotic lesions exhibited PARP14 and PARP9 proteins, further supporting the hypothesis that dysregulation of these PARPs contributes to arterial diseases.

Figure 3A:
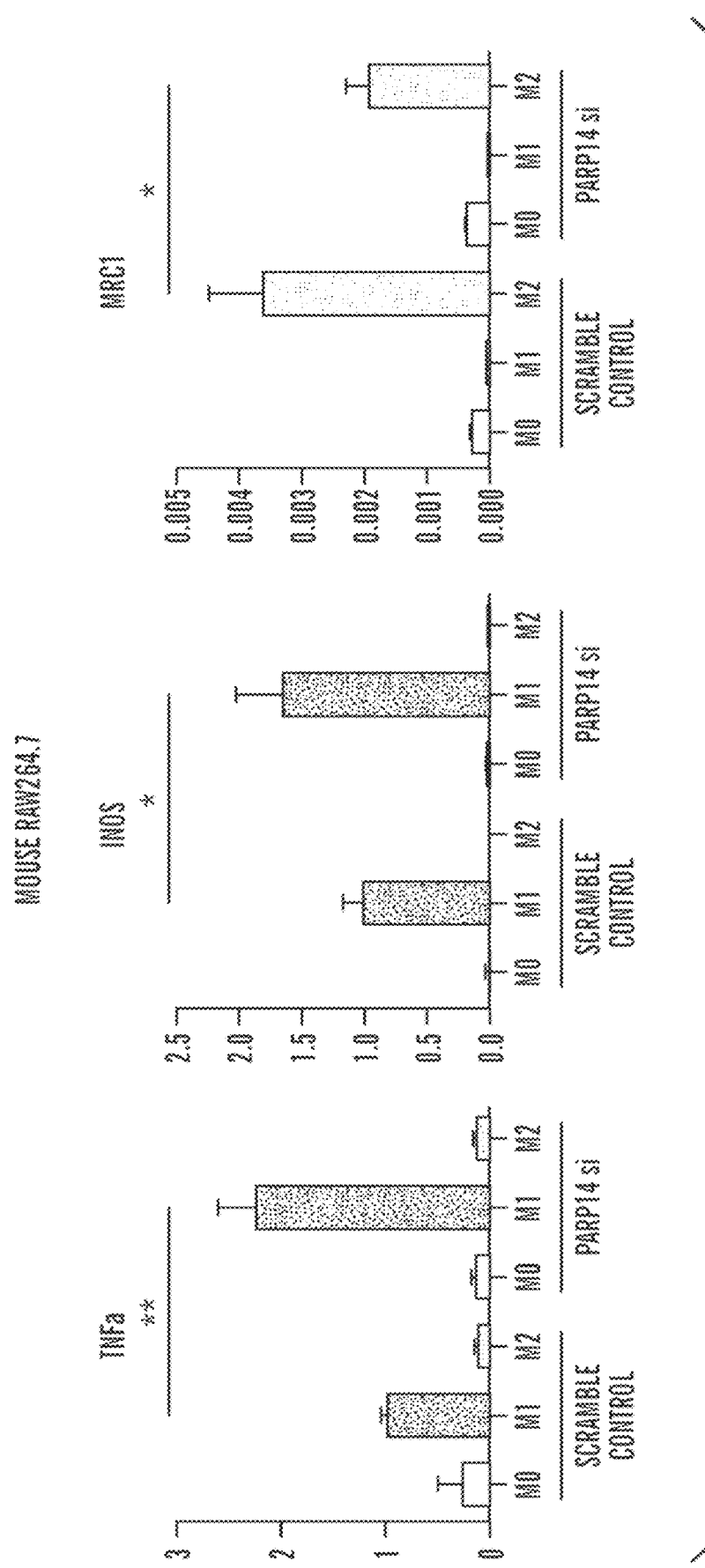
FIGS. 3A-3F show the effect of silencing PARP14 (FIGS. 3A-3D) and PARP9 (FIG. 3F) on polarization of mouse and human macrophage cell lines and primary macrophages and possible interaction of PARP14 and 9 (FIG. 3D); * and ** indicate p<0.05 and p<0.01 by student t-test, respectively.
Figure 3B:
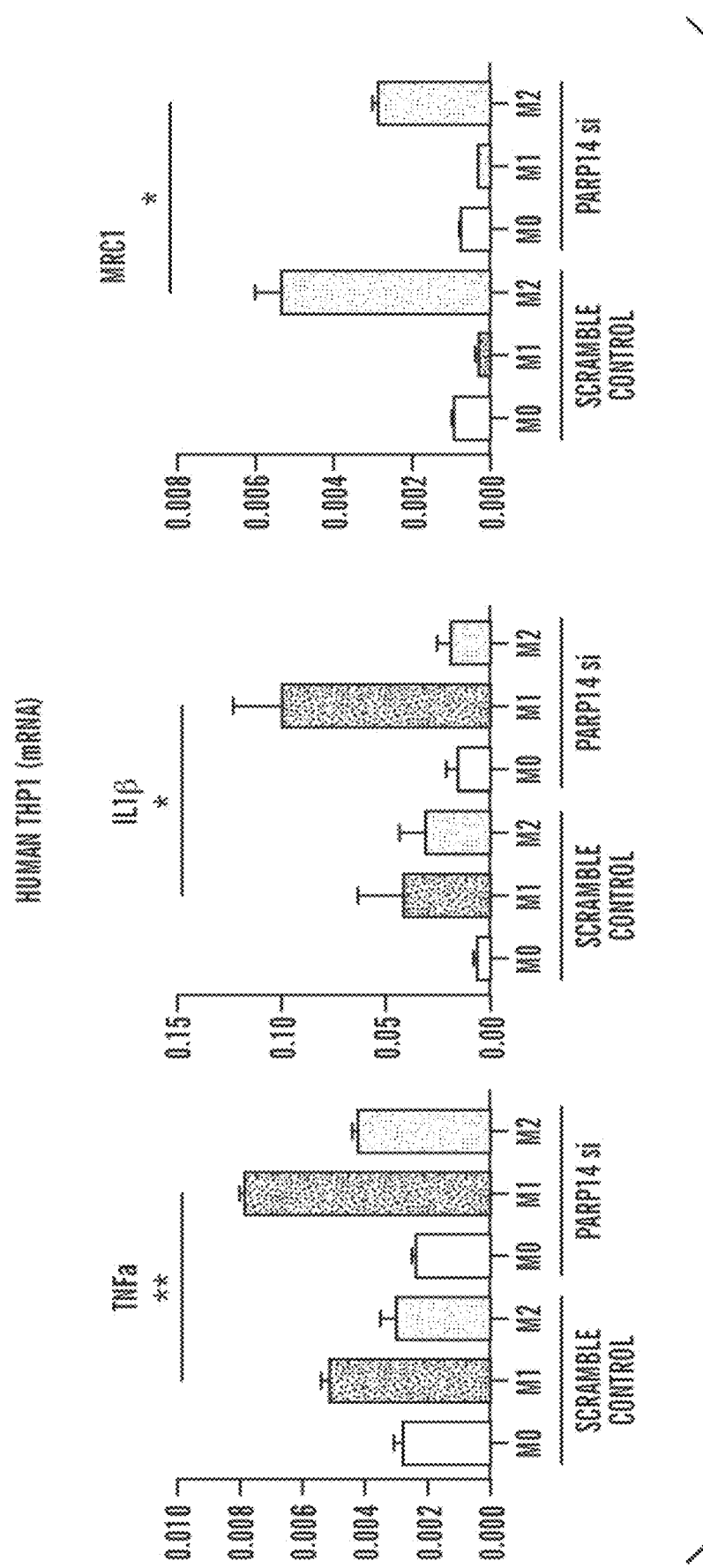
Figure 3C:
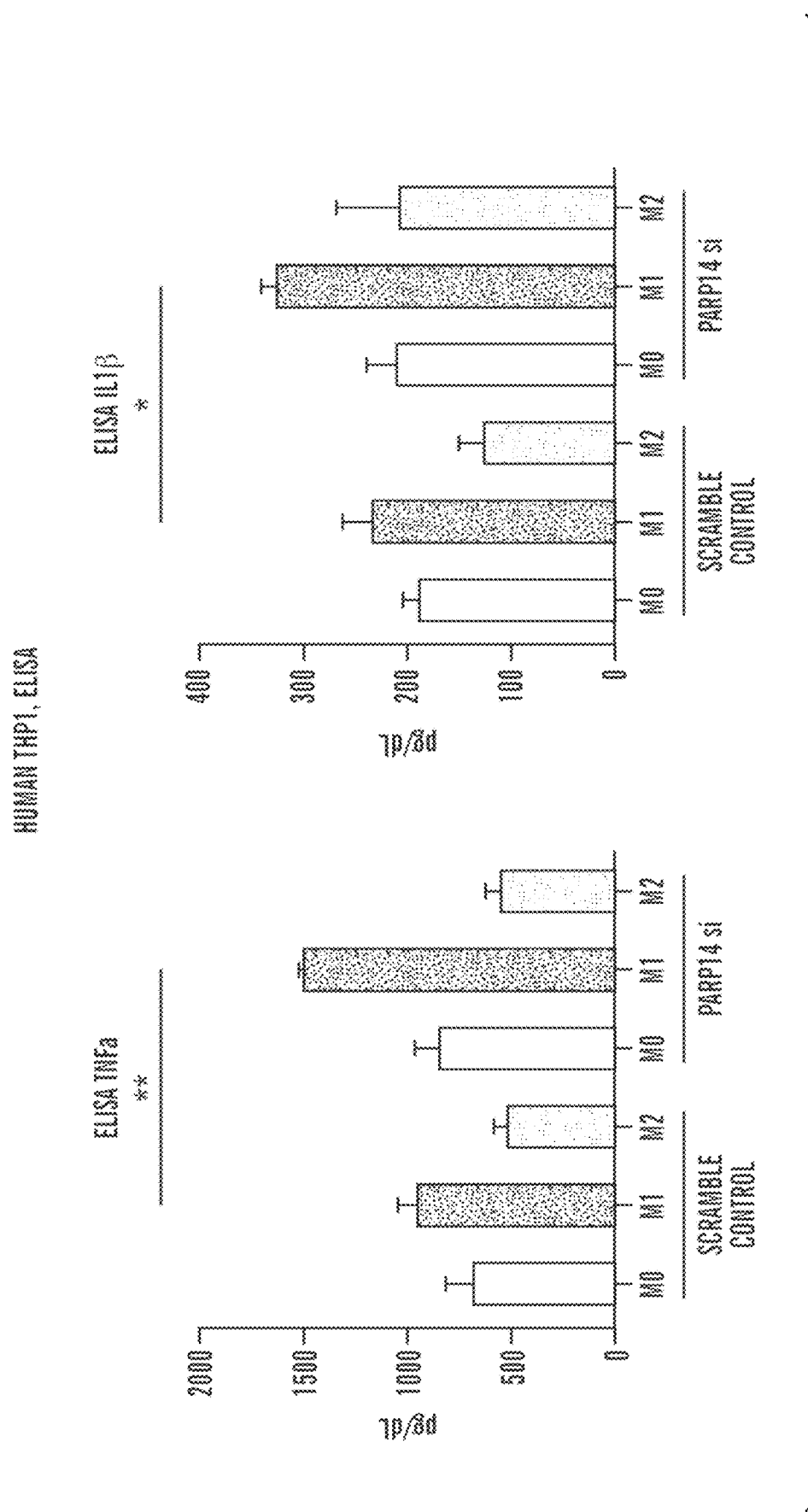
Figure 3D:
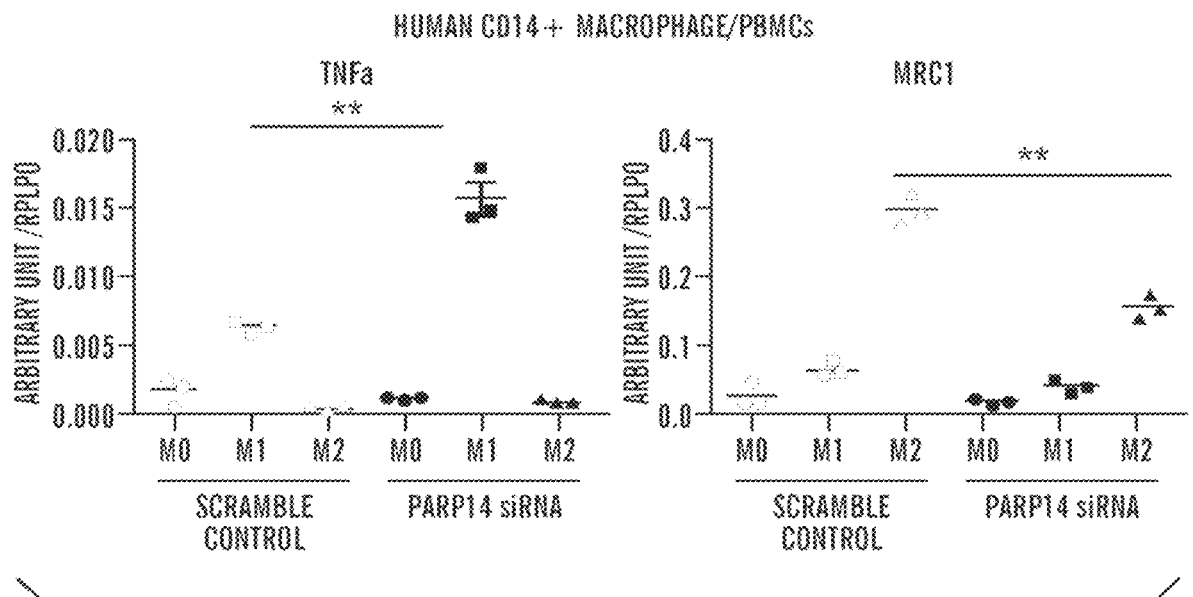
Figure 3E:
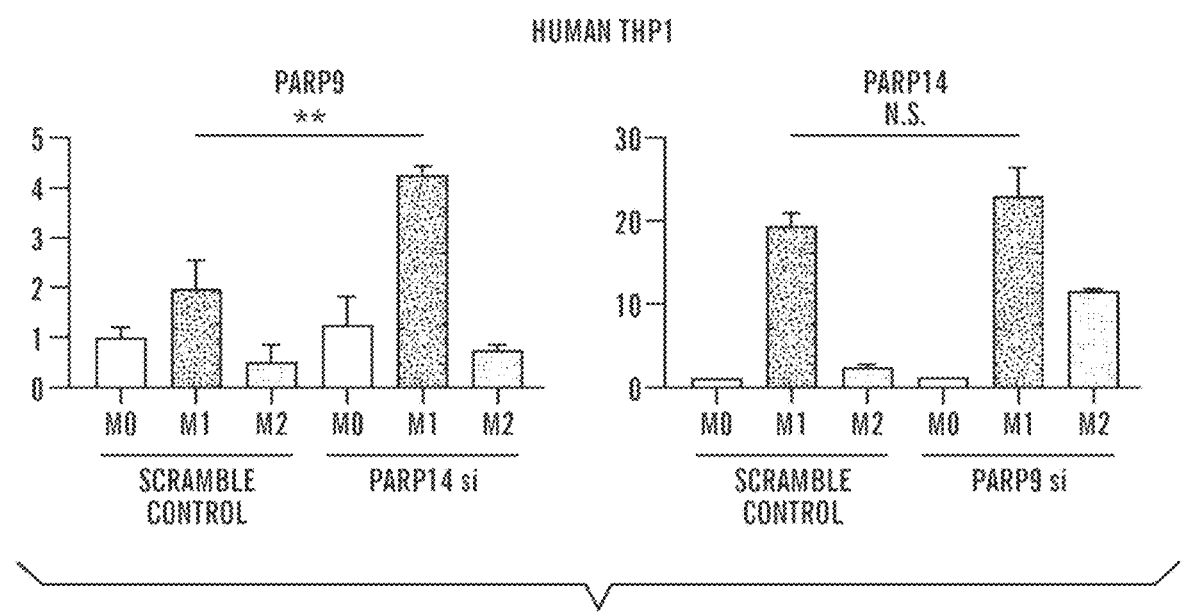
Figure 3F:
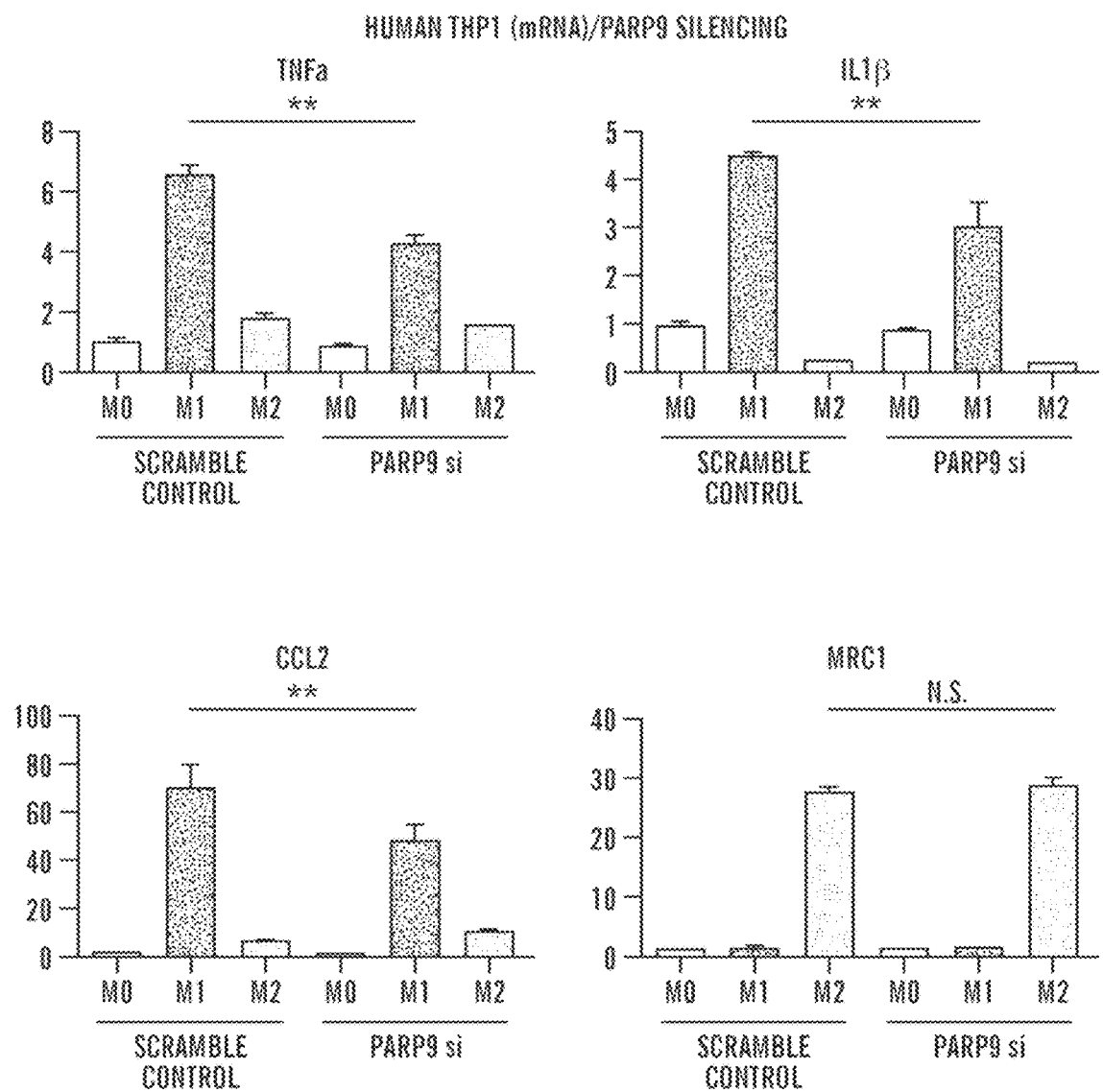
Figure 18:
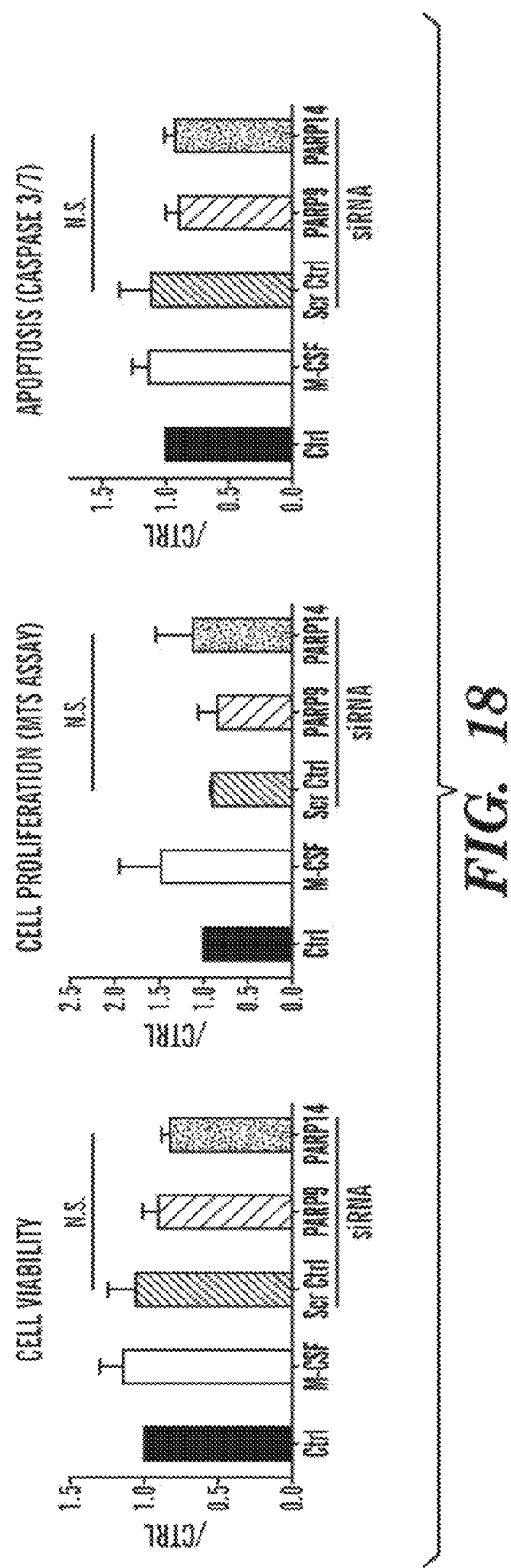
FIG. 18 shows cell viability/proliferation/apoptosis assays. PARP14 and PARP 9 silencing had no significant effects on viability, proliferation and apoptosis of mouse bone marrow-derived macrophages (n=3).

To explore the causal role of PARP14 and PARP9 in macrophage polarization, expression levels of gene products associated with macrophage polarization (e.g., TNFα, iNOS, IL-113, and CCL2/MCP-1 for the M1 responses; MRC1 and Arg1 for M2) gauged the downstream effects of the silencing of these PARPs using small interfering RNA (siRNA). PARP14 silencing significantly enhanced the induction of TNFα and iNOS by the M1 stimulator IFNγ, and suppressed the response of the M2 marker MRC1 to IL-4 in mouse RAW264.7 cells (FIG. 3A). In human THP-1 cells, PARP14 silencing also increased TNFα and IL-1β mRNA expression levels in the M1 condition and decreased MRC1 mRNA in the M2 condition (FIG. 3B). Increased levels of TNFα and IL-10 proteins in the supernatant of THP-1 cells with PARP14 silencing (FIG. 3C) supported these data. Furthermore, silencing PARP14 in human primary macrophages derived from CD14+ peripheral blood mononuclear cells (PBMCs) exerted similar effects (FIG. 3D). In contrast, silencing of PARP9 decreased mRNA levels of TNFα, IL-1β and CCL2/MCP-1 in THP-1 cells, while MRC1 showed no significant change (FIG. 3F). These findings indicate that PARP14 is an anti-inflammatory molecule and PARP9 is a pro-inflammatory molecule. PARP14 as well as PARP9 did not show significant effects on viability, proliferation, and apoptosis of mouse primary macrophages (FIG. 18).

PARP9 and PARP14 Regulate STAT1 and STAT6 Activation in Macrophages In Vitro

Figure 4A:
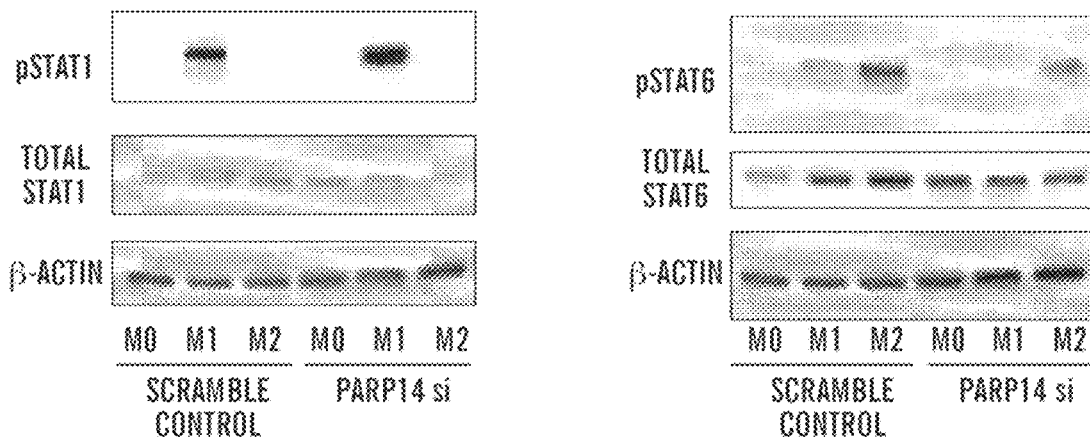
FIGS. 4A-4D show the effect of silencing PARP14 (FIGS. 4A, 4B) and PARP9 (FIG. 4C) on STAT1, STAT6 and STAT3 mediated cell signaling pathways in macrophage polarization.* and ** indicate p<0.05 and p<0.01 by student t-test, respectively.
Figure 4B:
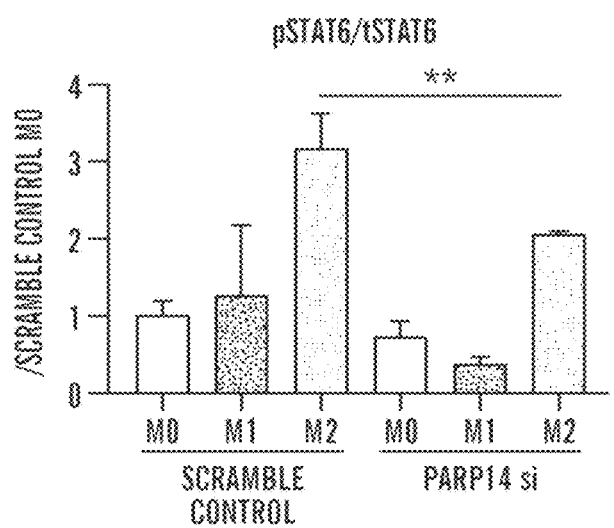
Figure 4C:
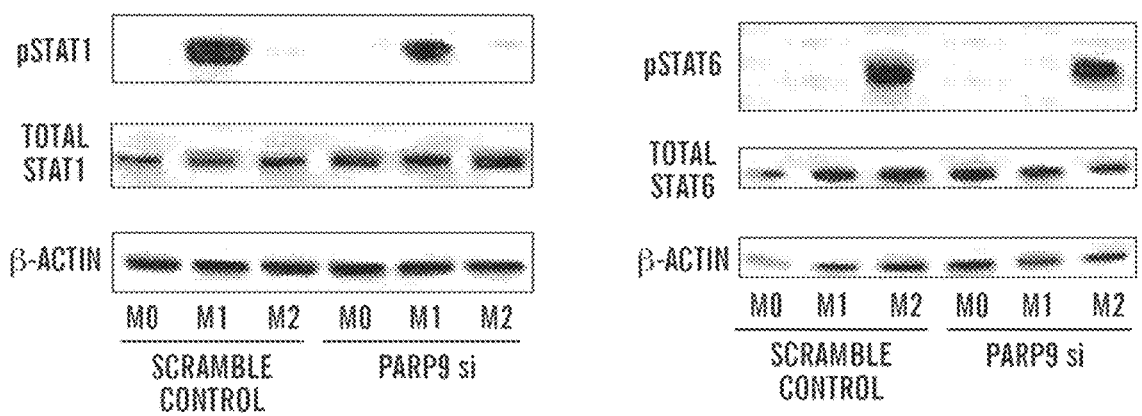
Figure 4D:
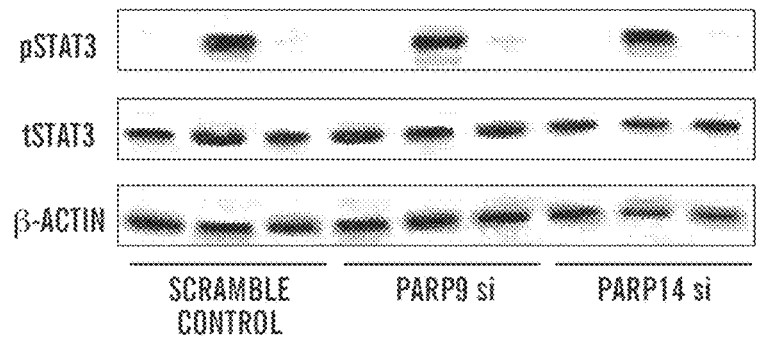
Figure 5A:
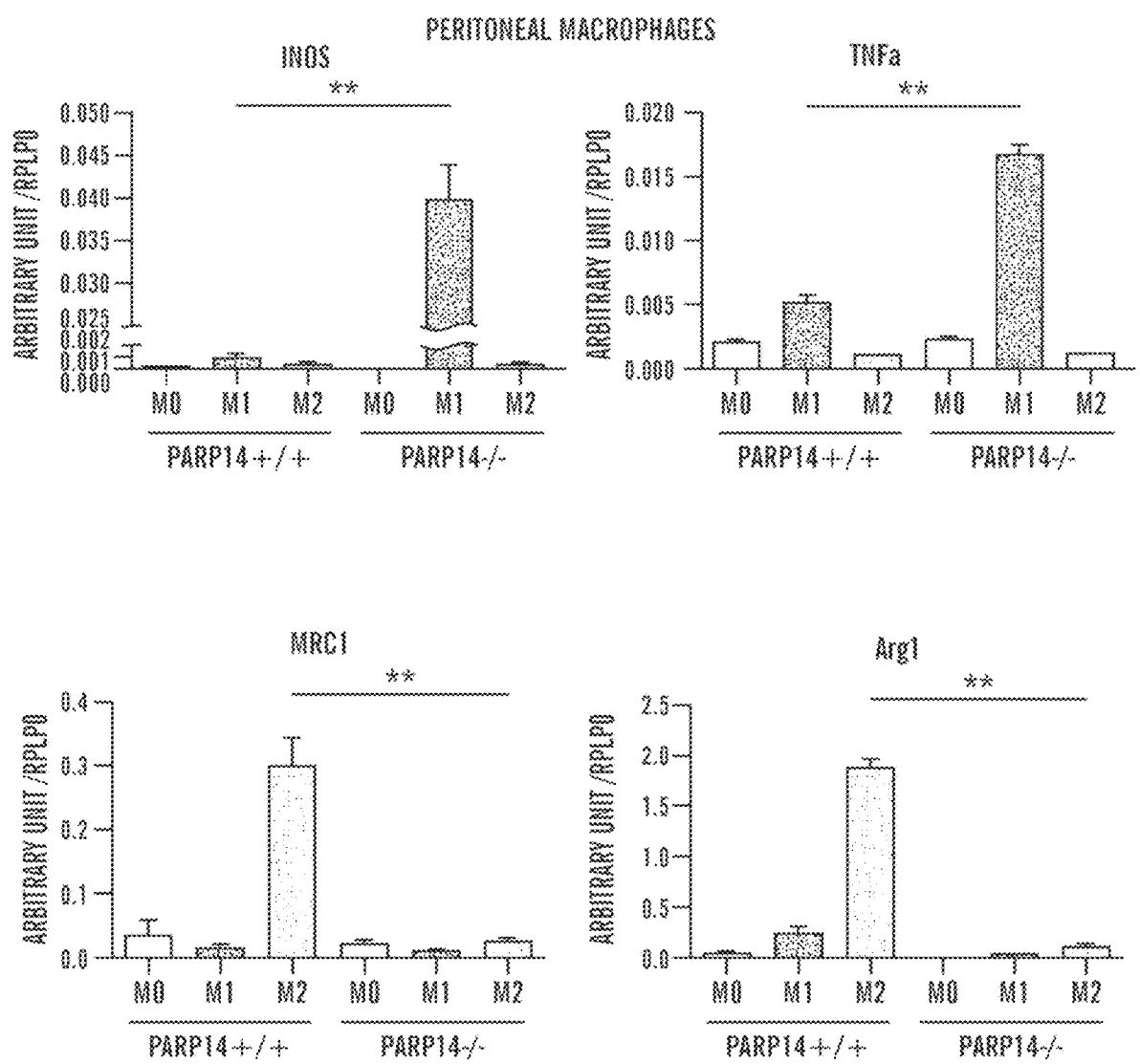
FIGS. 5A-5D show that primary macrophages comprising peritoneal macrophages (FIGS. 5A-5C), and bone marrow macrophages (FIG. 5D) isolated from PARP14 deficient mice are prone to exacerbate inflammatory property (M1) and to weaken anti-inflammatory property (M2); * and ** indicate p<0.05 and p<0.01 by student t-test, respectively.
Figure 5B:
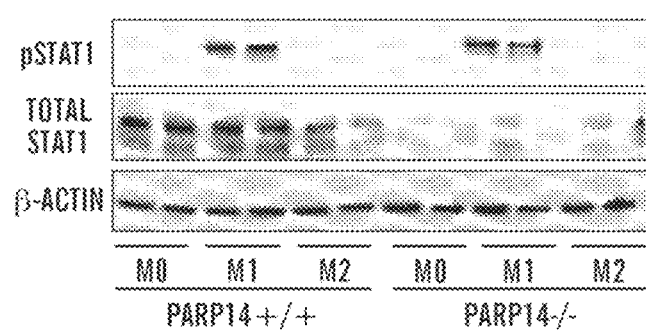
Figure 5B:
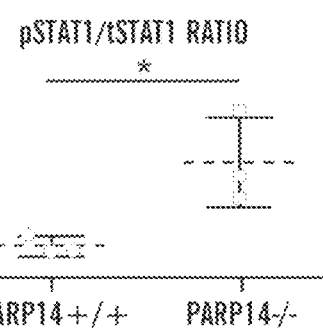
Figure 5B:
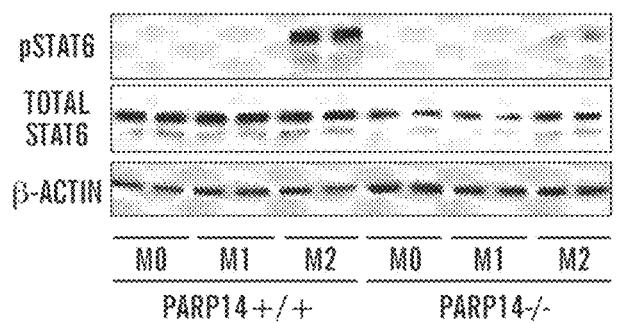
Figure 5B:
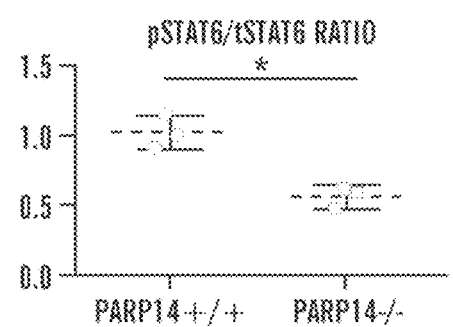
Figure 5C:
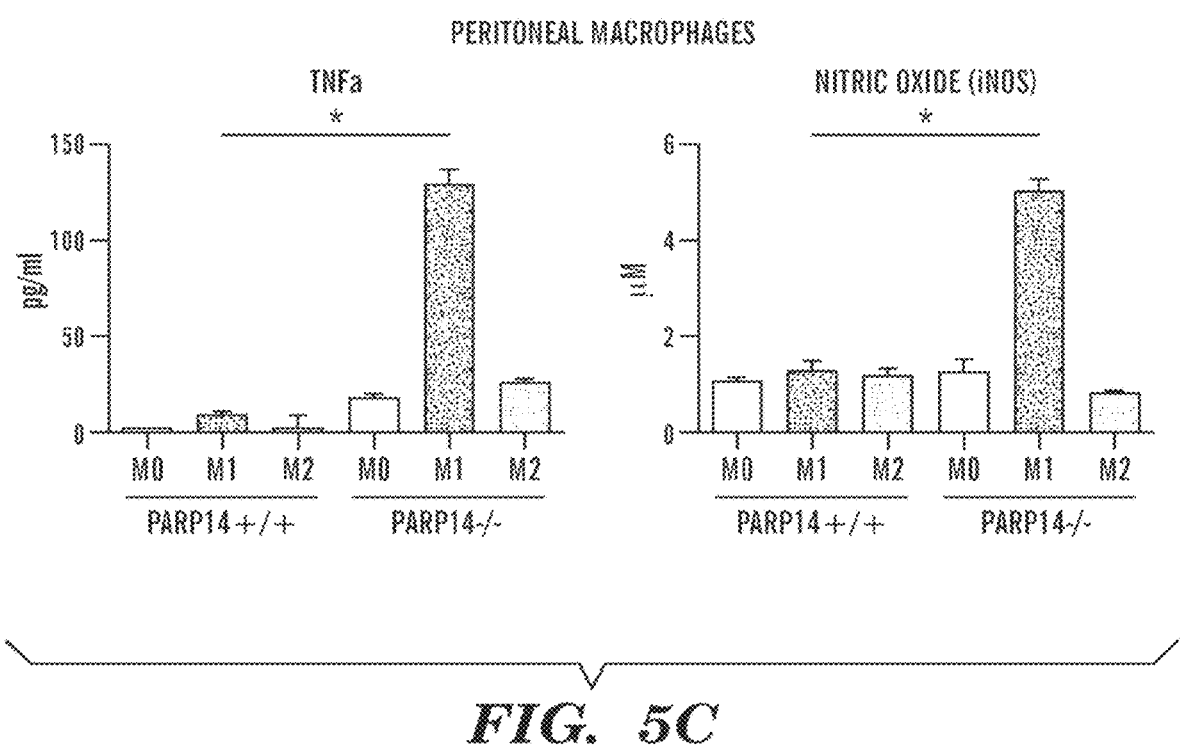
Figure 5D:
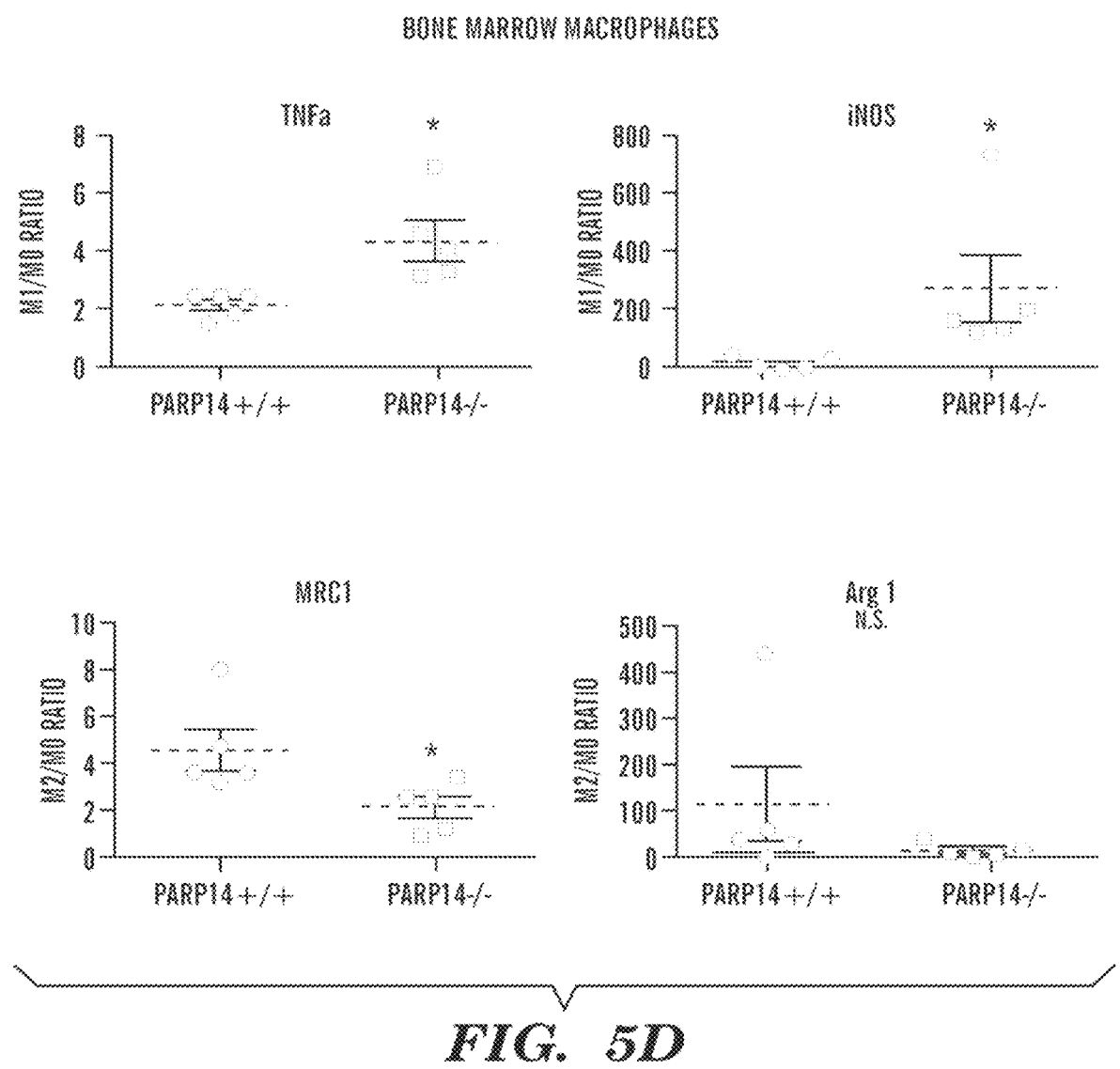
Figure 6:
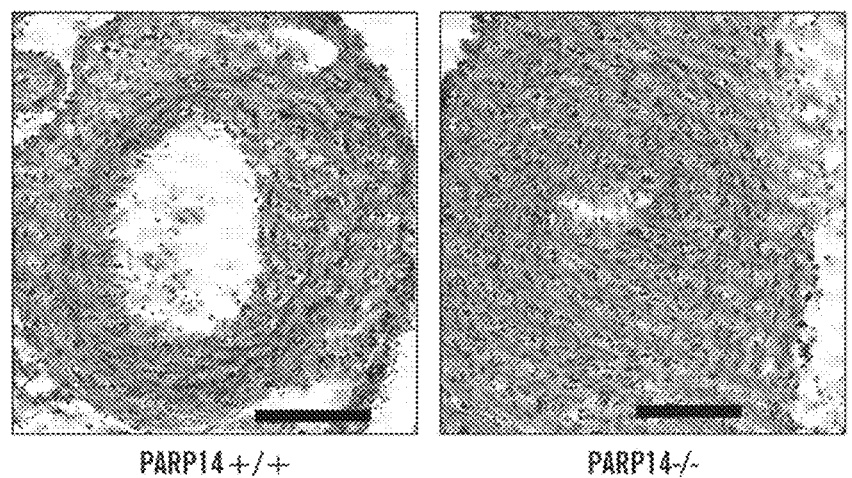
FIG. 6 shows neointima hyperplasia 2 weeks after wire-mediated vascular injury in PARP14−/− mice was higher than PARP14+/+ mice. Ratio to neointima area to media area was significantly higher in PARP14−/− mice (n=5). Scale bars indicate 100 μm.
Figure 6:
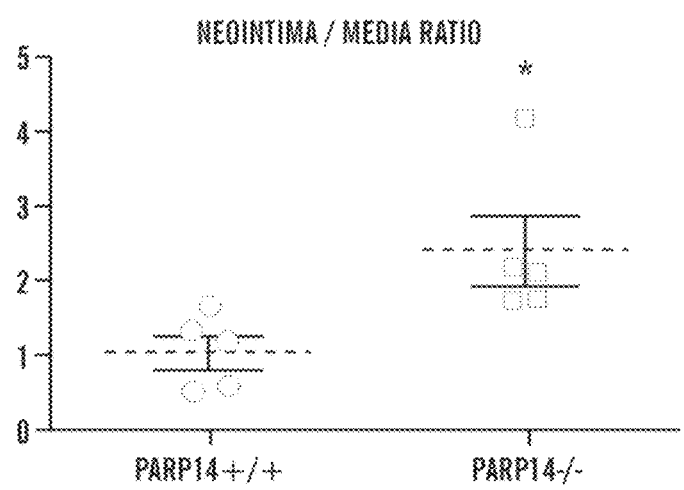
Figure 19:
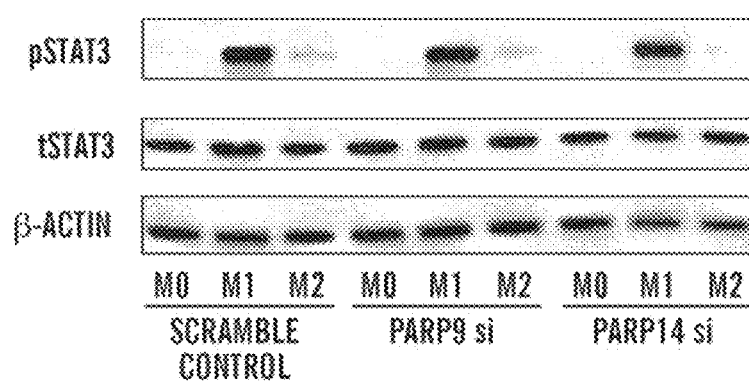
FIG. 19 shows western blot detection of STAT3 phosphorylation. Silencing of PARP14 or PARP9 had no effect on phosphorylation of STAT3 (pSTAT3) in THP-1 cells. Total STAT3 (tSTAT3).

Although expression patterns of PARP14 and PARP9 in M1 and M2 macrophages were similar (FIGS. 2B-2C), their respective siRNA experiments yielded opposing results (FIGS. 3A-3D, 3F). IFNγ signaling involves activation (phosphorylation) of pro-inflammatory STAT1, while the IL-4 pathway uses anti-inflammatory STAT6 phosphorylation(32, 33). PARP14 silencing accelerated IFNγ-induced STAT1 phosphorylation in M1 macrophages and suppressed IL-4-promoted STAT6 phosphorylation in M2 macrophages (FIG. 4A). In contrast, PARP9 silencing decreased STAT1 phosphorylation in M1 macrophages (FIG. 4C). PARP14 may thus suppress M1 polarization by modulating the IFNγ-STAT1 axis, and promote the IL-4-STAT6-M2 pathway. In contrast, PARP9 may activate IFNγ-STAT1 signaling, inducing M1 polarization. Evidence indicates the participation of STAT3 in immune responses in various contexts(34), but PARP14 or PARP9 silencing produced no significant effects on STAT3 phosphorylation (FIG. 19).

PARP9 and PARP14 Interact with Each Other

Figure 10E:
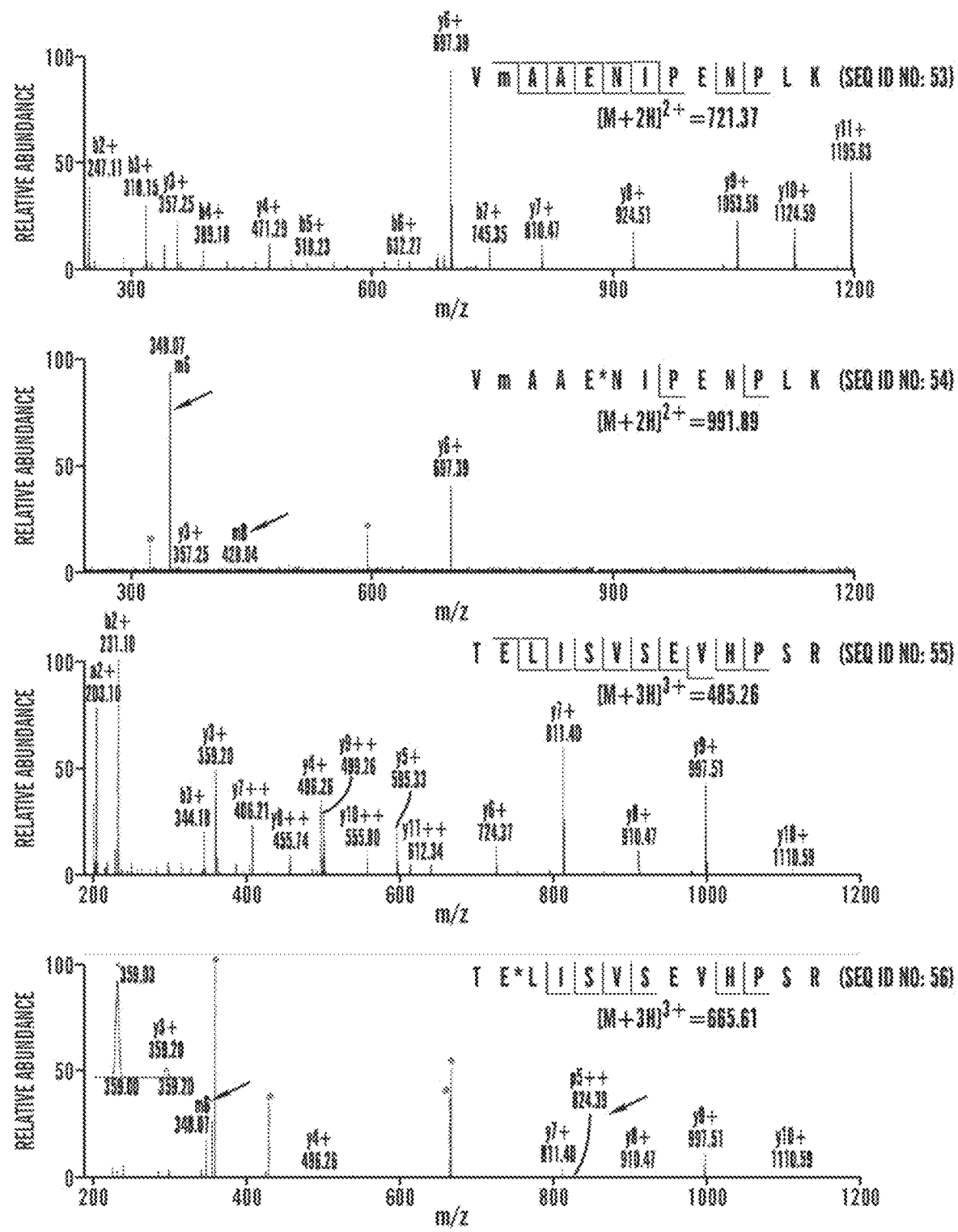
Figure 10F:
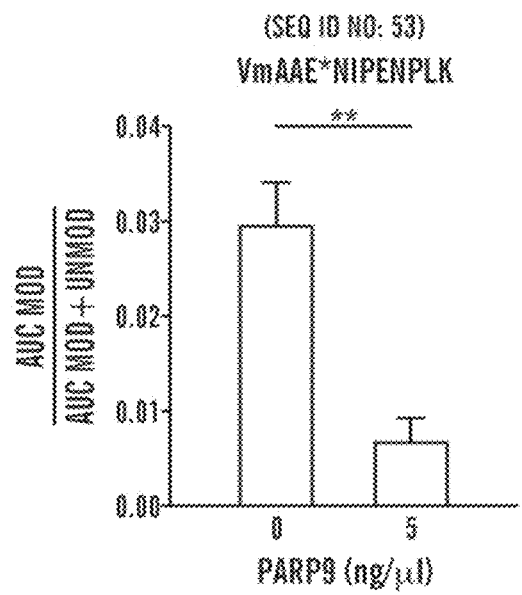
Figure 10F:
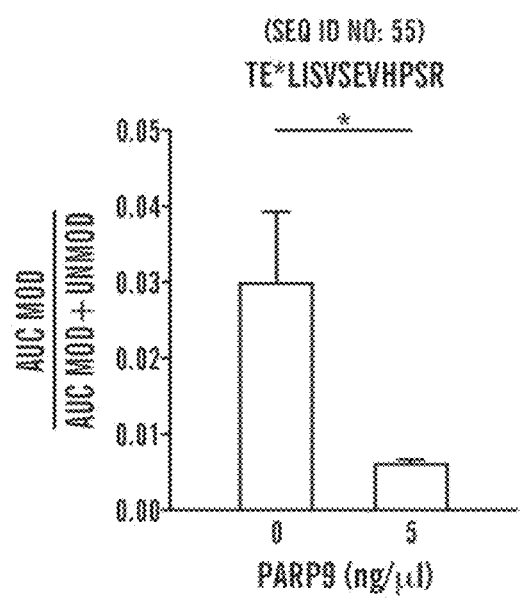

The results demonstrated above engendered the hypothesis of regulatory interplay between PARP14 and PARP9. Indeed, PARP14 silencing significantly increased PARP9 mRNA expression, while PARP9 silencing tended to increase PARP14 mRNA (FIG. 10A). Previous reports show that, in B lymphocytes, IL-4 promotes catalytic activity of PARP14, leading to ribosylation of HDAC2, HDAC3, and p100, and activation of STAT6, thereby promoting its binding to IL-4-responsive gene promoters(25, 26, 35, 36). As co-immunoprecipitation assay in THP-1 cells showed a complex formed by PARP9 and PARP14 (FIG. 10B), these two molecules may physically interact with each other in macrophages. Recombinant PARP14 protein induced ADP-ribosylation of PARP14 itself, PARP9, and STAT1a (FIG. 10C). PARP9 did not ADP-ribosylate STAT1a, which validates a previous report showing that PARP9 lacks catalytic activity(27). Interestingly, supplementation of PARP9 suppressed STAT1α ribosylation (FIG. 10C). While the majority of other PARP family members such as PARP1 are poly-ADP-ribosylation enzymes, PARP14 is a mono-ADP-ribosyltransferase(24). Liquid chromatography tandem mass spectrometry (LC-MS/MS) determined that Glu657 and Glu705 of STAT1α were mono-ADP-ribosylated by PARP14 (FIGS. 10D and 10E). Glu657 and Glu705 neighbor Tyr701, a functionally critical phosphorylation site of STAT1α (FIGS. 10D and 10E). LC-MS/MS further revealed that recombinant PARP9 inhibited PARP14-induced mono ADP-ribosylation at Glu657 and Glu705 of STAT1α (FIG. 10F). Collectively, these results indicate a potential mechanism for macrophage activation in which PARP14 may mono-ADP ribosylates pro-inflammatory STAT1a, a process that PARP9 suppresses.

Figure 11A:
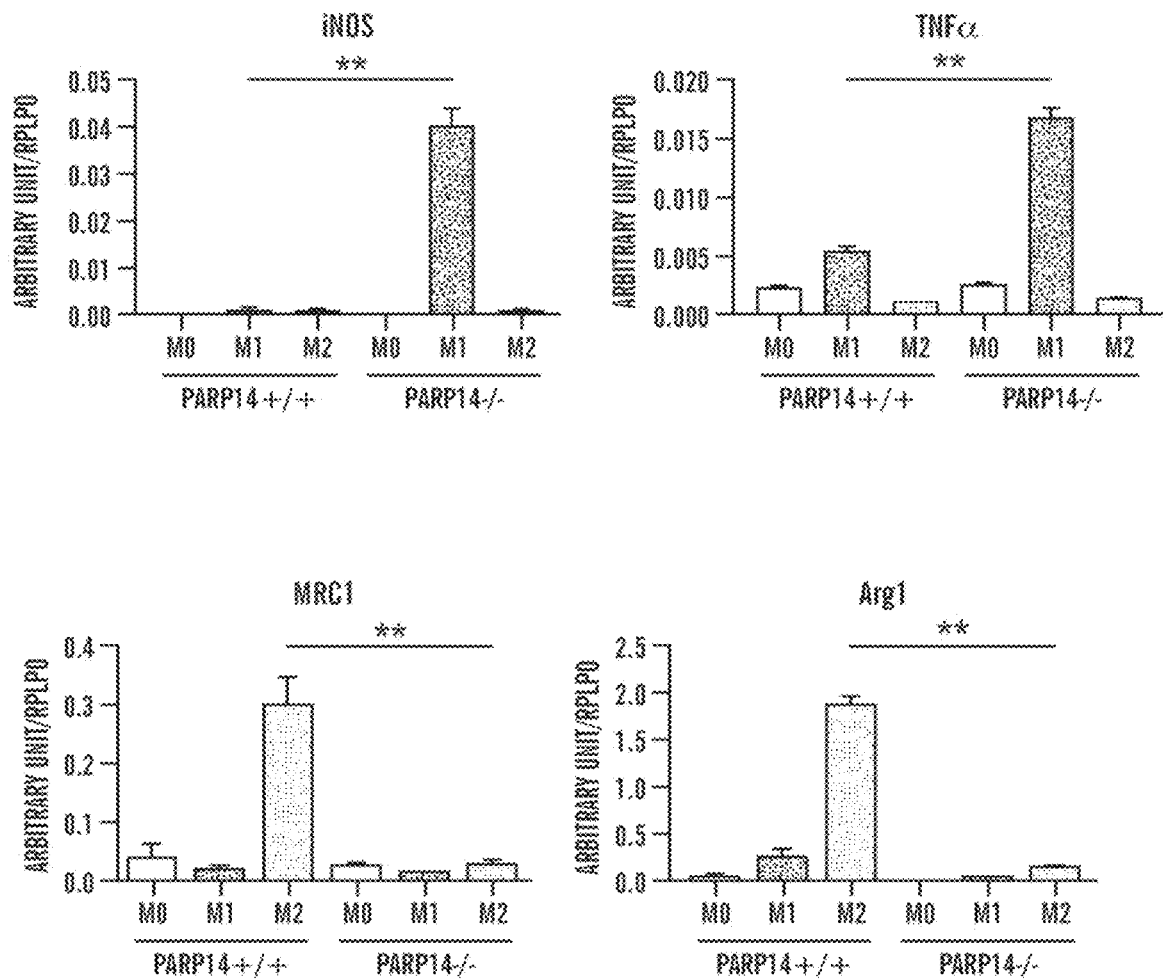
FIGS. 11A-11F show PARP14 deletion enhances macrophage activation and arterial lesion formation in vivo.
Figure 11B:
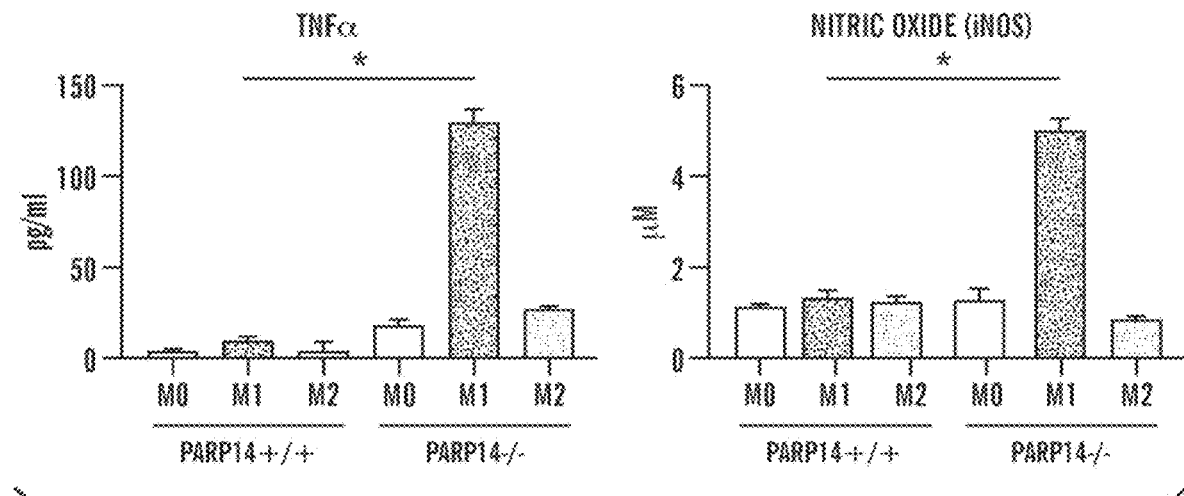
Figure 11C:
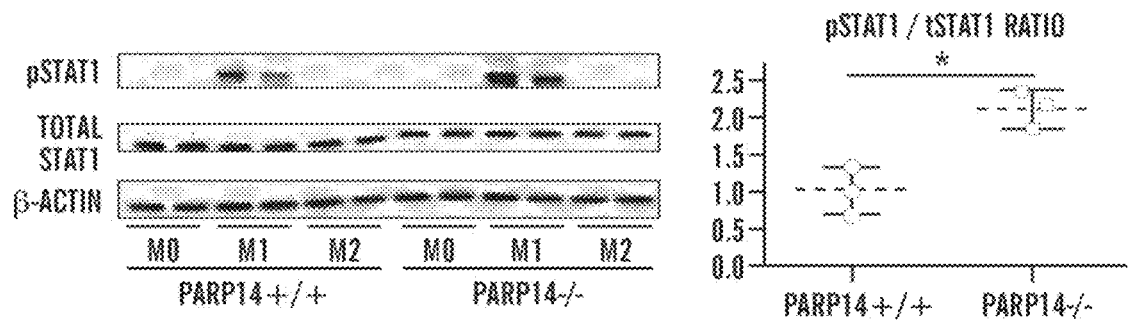
Figure 11C:
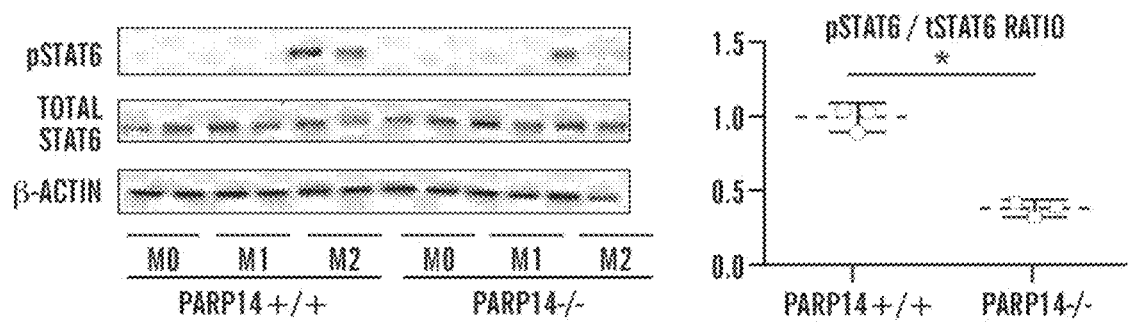
Figure 11D:
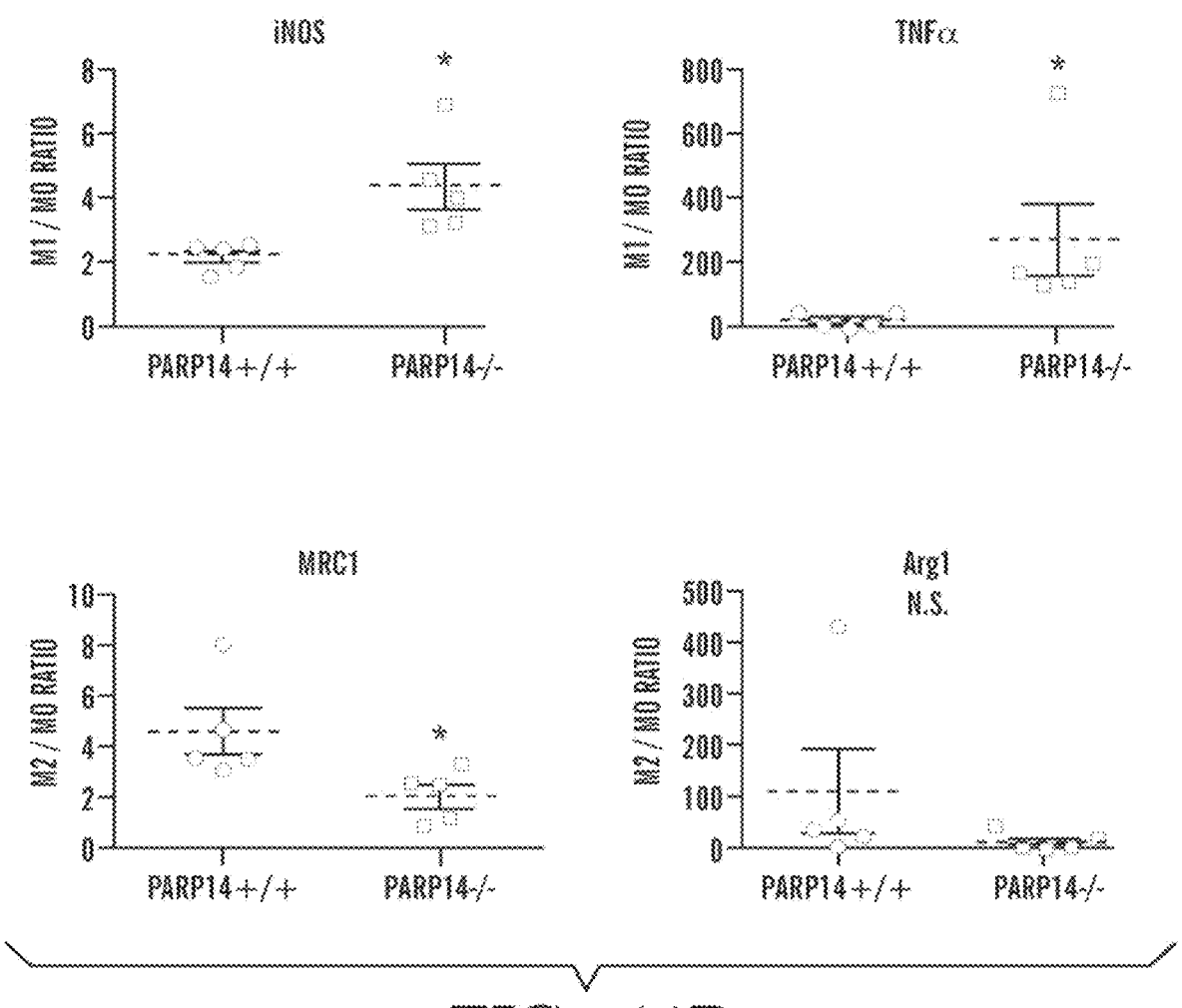

PARP14 Deficiency In Vivo Enhances Macrophage Activation and Arterial Lesion Development PARP14$^{-/-}$ mice further provided in vivo evidence that PARP14 participates in arterial lesion formation and macrophage activation. PARP14$^{-/-}$ or PARP14$^{+/+}$ mouse peritoneal macrophages enabled the examination of macrophage phenotype and vascular lesion formation. Consistent with the in vitro siRNA experiments in cultured macrophages, data showed markedly higher mRNA and protein levels of factors associated with pro-inflammatory M1 polarization and lower M2 molecules in PARP14$^{-/-}$ macrophages as compared to PARP14$^{+/+}$ cells (FIGS. 11A and 11B). PARP14 deficiency also enhanced phosphorylation of STAT1 induced in M1 condition and decreased STAT6 phosphorylation in M2 in peritoneal macrophages (FIG. 11C). Primary macrophages derived from PARP14$^{-/-}$ bone marrow cells showed similar results for the M1 and M2 genes (FIG. 11D).

Figure 11E:
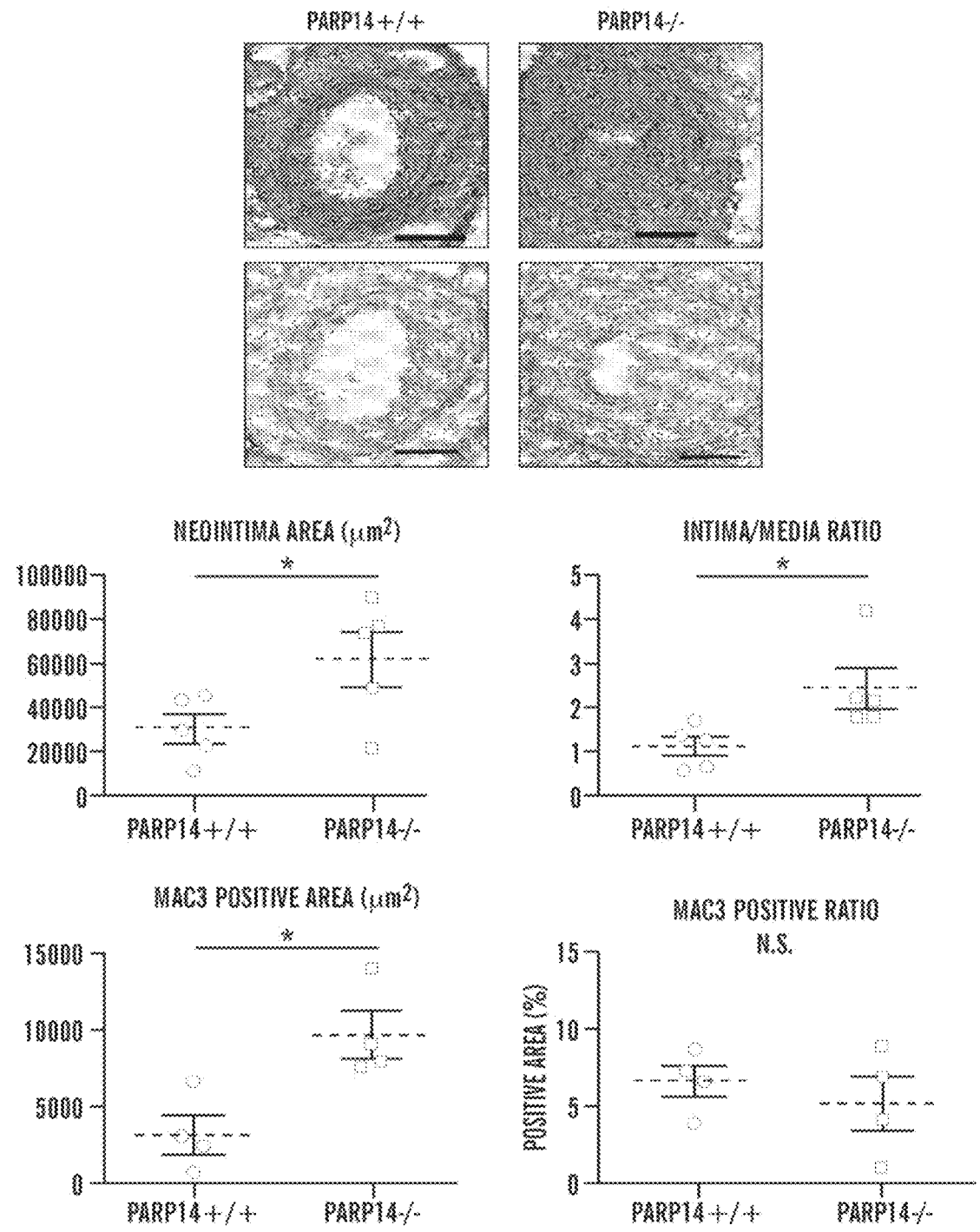
Figure 11F:
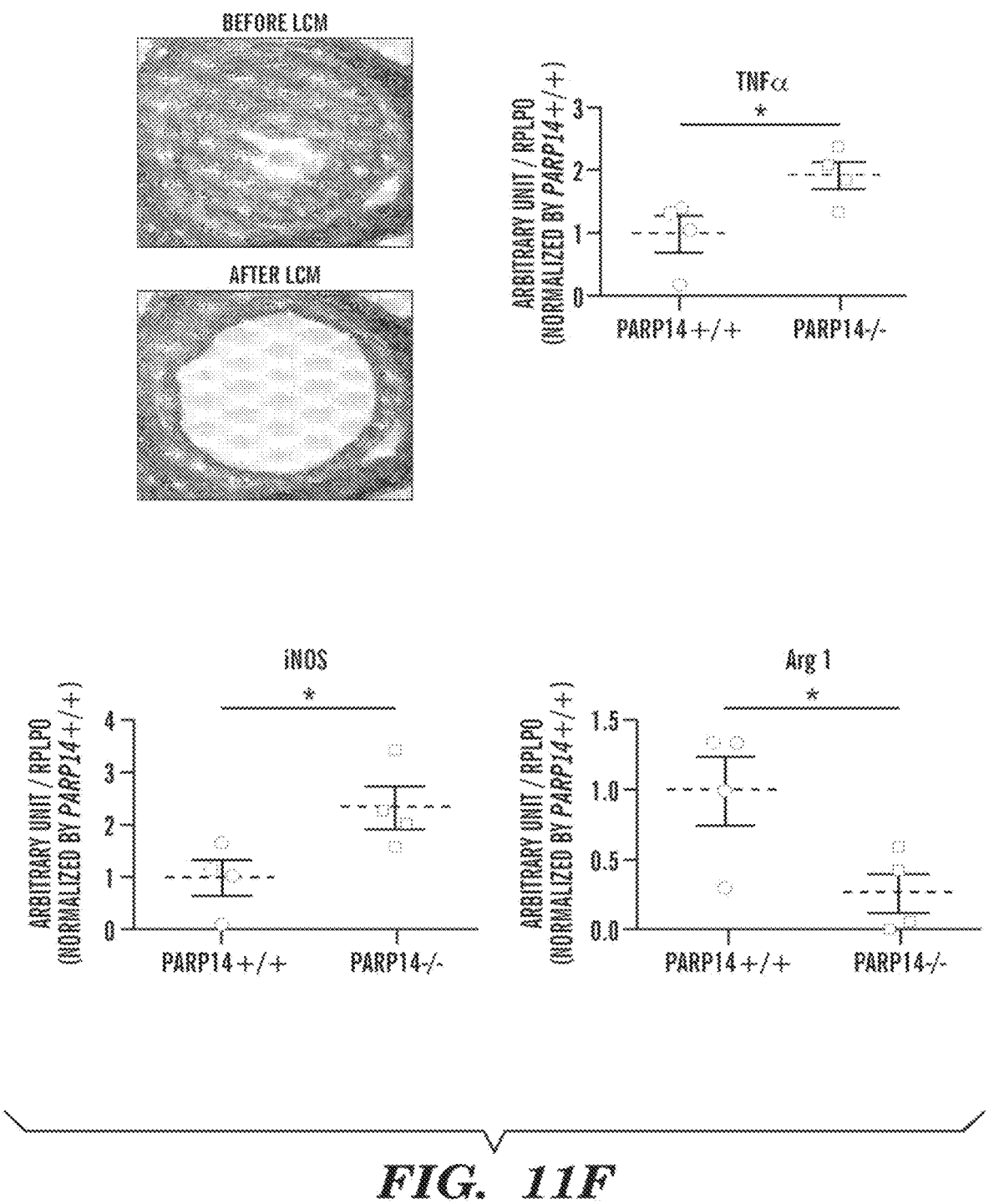

To gain further insight into the function of PARP14 in vascular disease, beyond the in vitro M1/M2 model, the lesion formation in the femoral arteries of PARP14$^{-/-}$ mice after wire-mediated mechanical injury was examined. PARP14 deficiency accelerated neointima formation (FIG. 11E) and increased macrophage accumulation, as indicated by Mac3 immunostaining (FIG. 11E). Laser capture microdissection of the intima of injured femoral arteries followed by real-time PCR demonstrated higher expression levels of the M1 molecules TNFα and iNOS and lower M2 marker Arg1 in PARP14$^{-/-}$ mice as compared to PARP14$^{+/+}$ mice (FIG. 11F).

The Possible Role of PARP9 and PARP14 in Smooth Muscle and Endothelial Cells

Figure 20A:
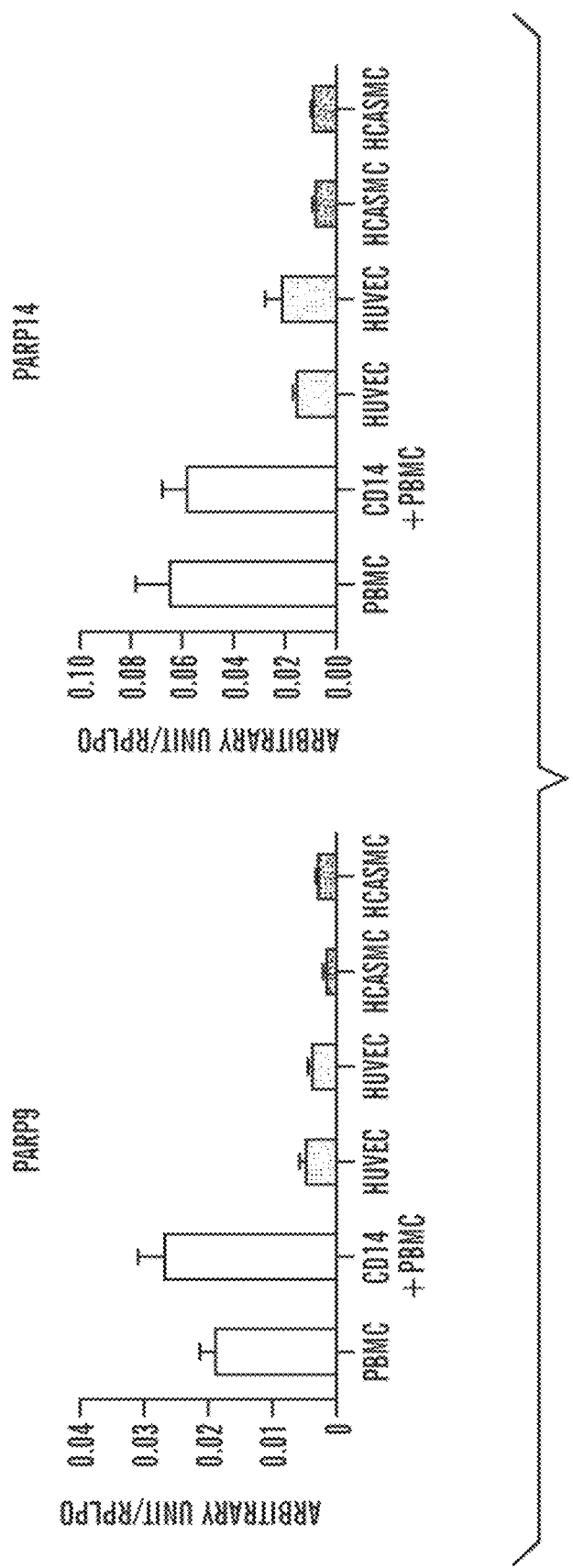
FIGS. 20A-20B show PARP9/14 function in smooth muscle cells and endothelial cells. PARP14 deficiency promoted TNFα and iNOS expression in SMCs, while did not changed SMC-related genes. SMα-actin positive area was similar in the intima of injured femoral arteries. PARP9 silencing suppressed ICAM1 expression in EC, while no significant change occurred in other genes.
Figure 20A:
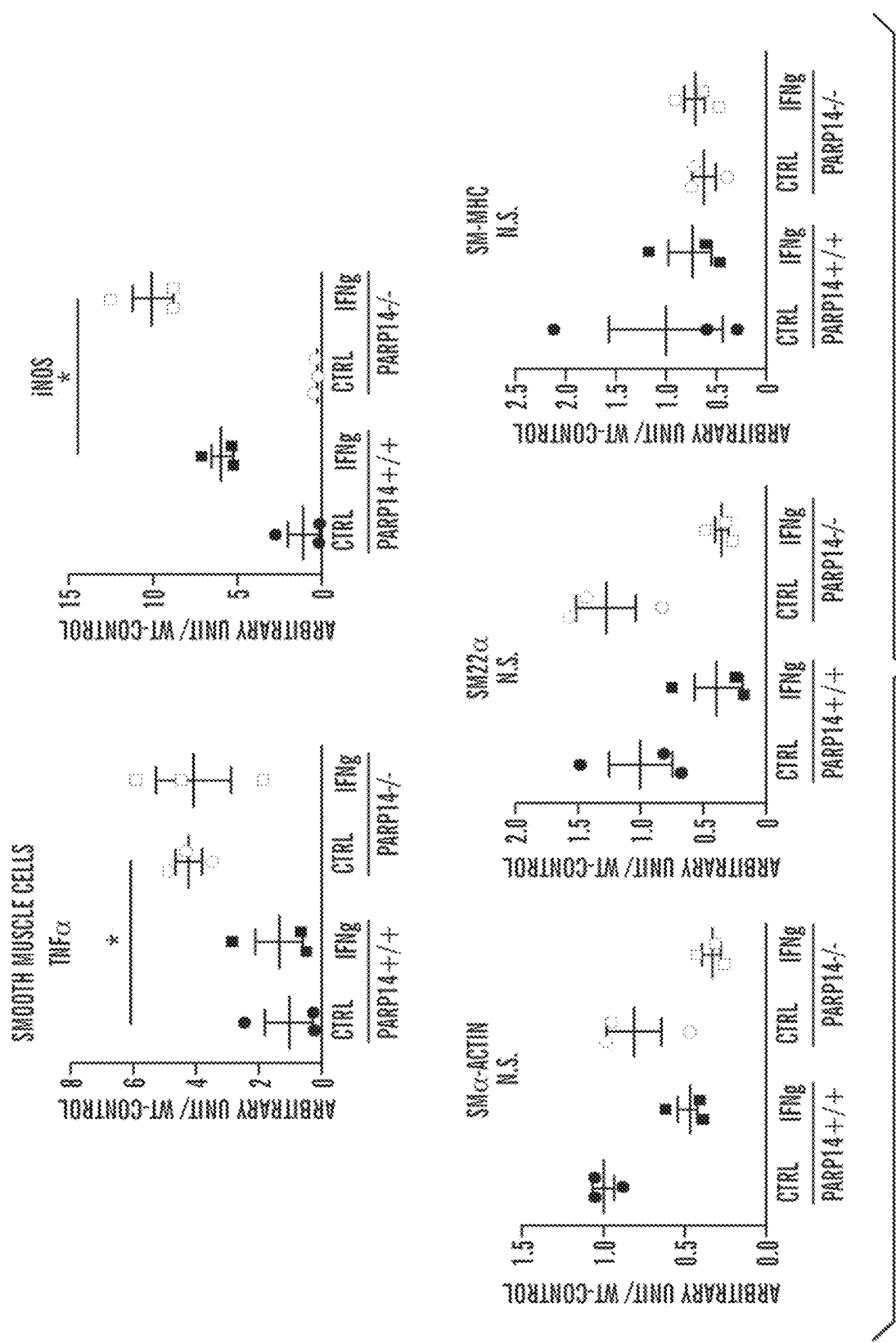
Figure 20A:
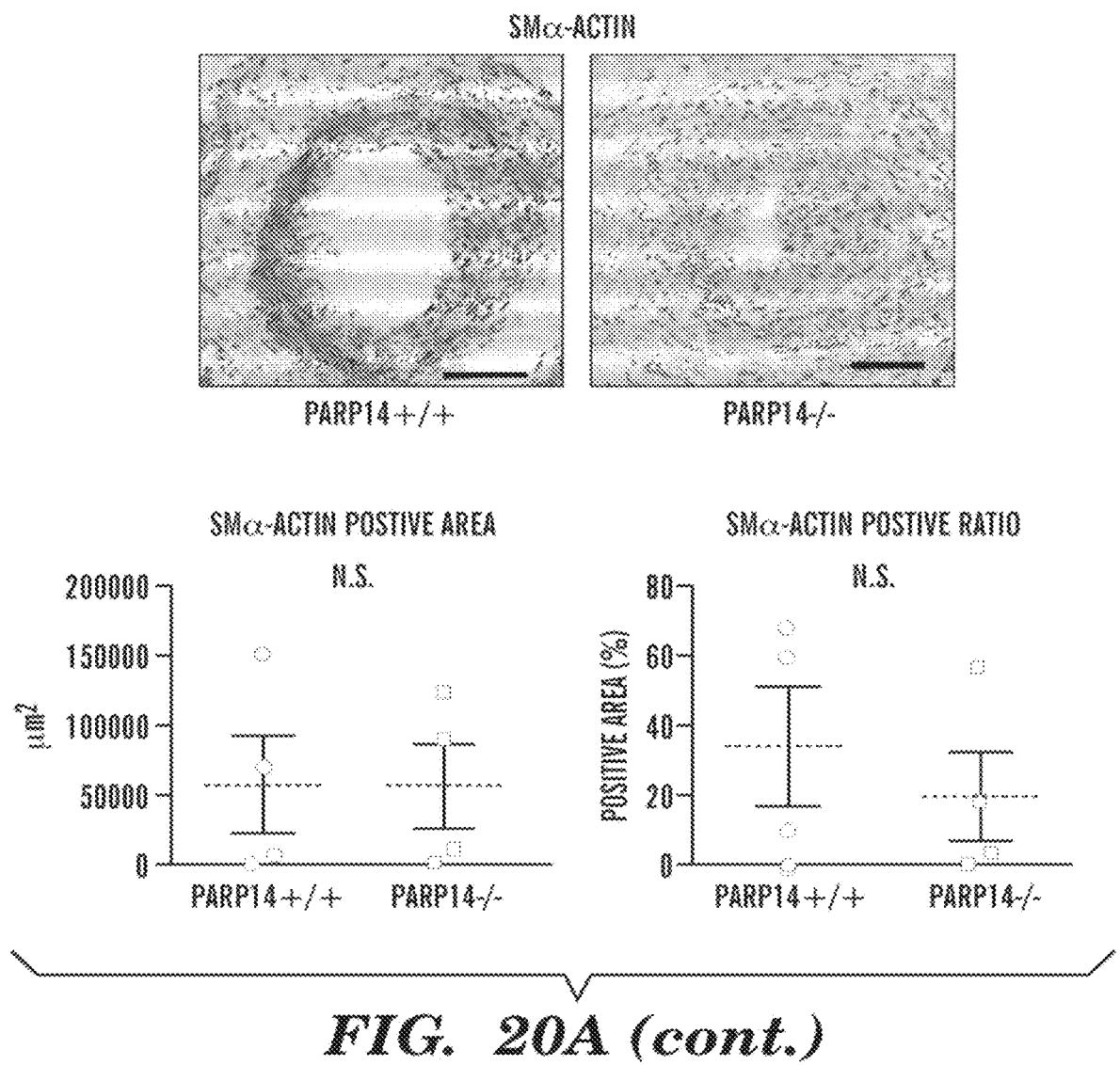
Figure 20B:
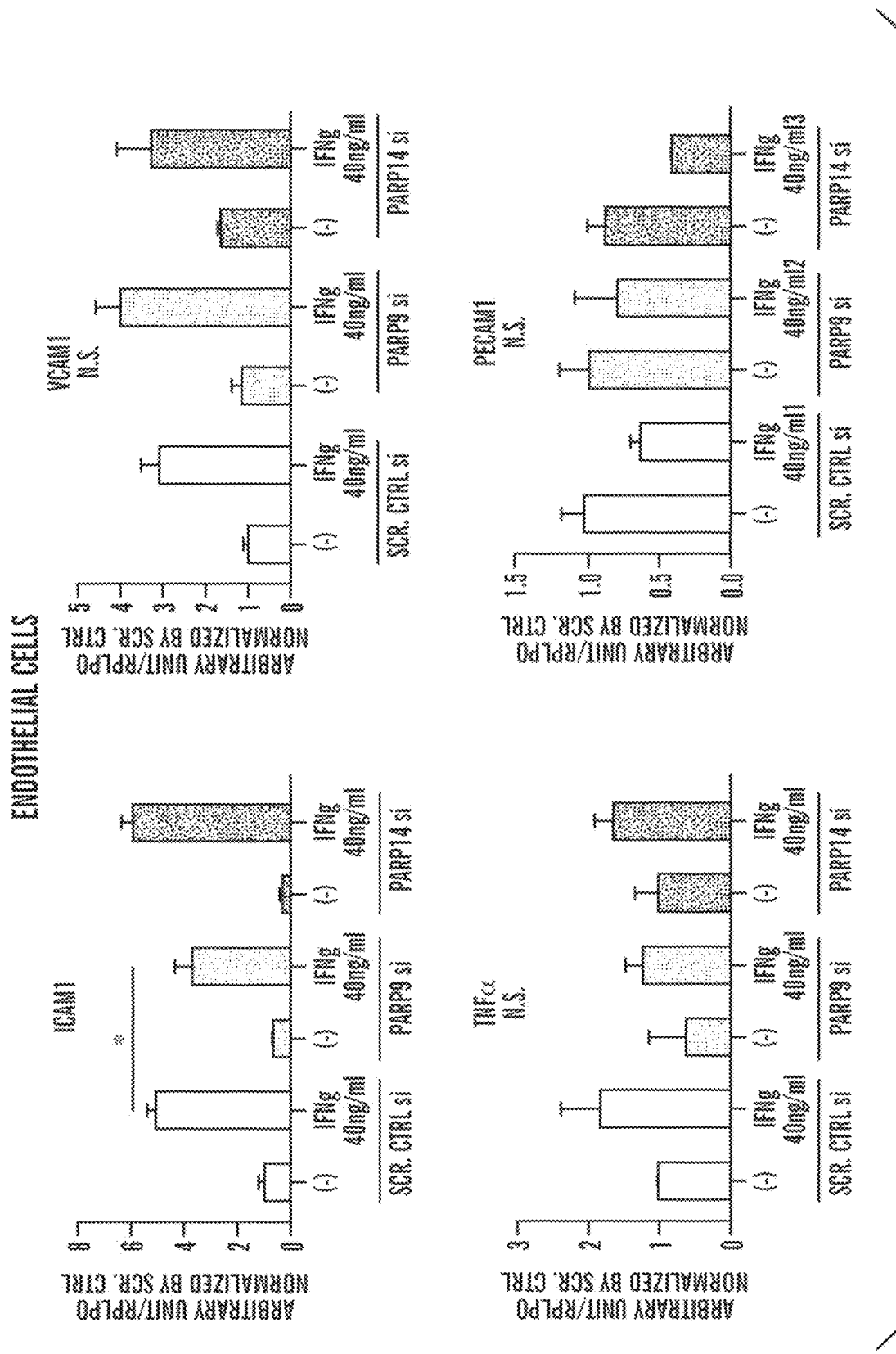

With the aim to discover novel therapeutic targets for macrophage-mediated diseases, unbiased proteomics and bioinformatics identified PARP9 and PARP14 as potential regulators of macrophage activation. Compare to primary smooth muscle cells and endothelial cells, both PARP9 and PARP14 mRNA expression were higher in primary cultured macrophages (FIG. 20A). The present study thus focuses on the role of these PARP family members in macrophage biology. Nevertheless, the possible function of PARP9 and PARP14 in other vascular cell types was examined. In primary smooth muscle cells (SMC) isolated from the mouse aorta, IFNγ induced inflammatory responses, as gauged by increased expression of TNFα and iNOS, and suppressed the expression of SMC differentiation marker genes SM α-actin, SM22a, and myosin heavy chain (SM-MHC) (FIG. 20A). The induction of TNFα and iNOS by IFNγ were enhanced in PARP14−/− SMC than those from PARP14+/+ mice. PARP14 deficiency produced no significant changes in SM α-actin, SM22α and SM-MHC expression in vitro. In the intima of mechanically-injured femoral arteries of PARP14+/+ and PARP14−/− mice, the absolute and % areas of intimal cells immunoreactive for SM α-actin did not differ (n=4) (FIG. 20A). These results indicate that PARP14 deficiency showed no effects on intimal SMC accumulation in vivo. In cultured endothelial cells (EC), IFNγ induced expression of ICAM-1, VCAM-1, and TNFα, but did not change PECAM-1 (FIG. 20B). PARP9 silencing partially suppressed ICAM-1 induction by IFNγ, but produced no effects on VCAM-1, TNFα, or PECAM-1. PARP14 silencing caused no changes in the responses of these molecules to IFNγ. These results indicate that PARP9 and PARP14 may play some role in activation of SMC and EC at least in vitro. Without wishing to be bound by theory, relative contributions of SMC or EC-derived PARP9 and PARP14 to arterial disease, however, may not be substantial as compared to those PARP family members expressed in macrophages.

Figure 12:
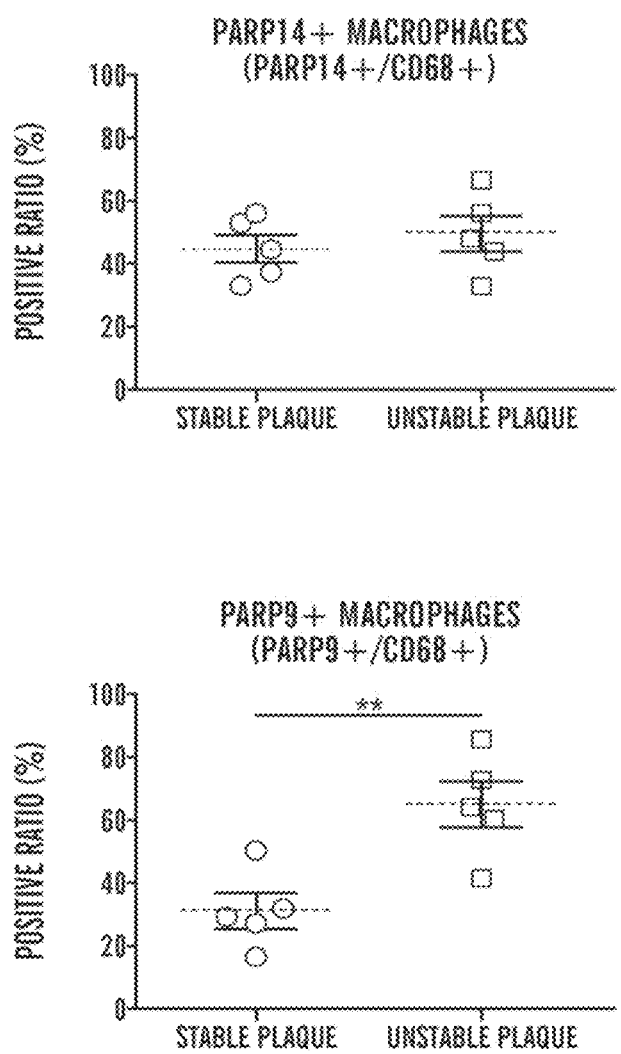
FIG. 12 is a set of plots showing expression of PARP9 and PARP14 in human plaque macrophages. Prevalence of PARP14+ or PARP9+ macrophages in stable/unstable plaque.

"Unstable" Human Atherosclerotic Plaques Contained More PARP9-Expressing Macrophages To seek additional in vivo evidence for the potential role of PARP 14 and PARP9 in arterial disease, human carotid atherosclerotic plaques surgically removed by endarterectomy were examined. Immunofluorescence staining revealed that PARP14 and PARP9 signals were predominantly localized in plaque macrophages, as indicated by the overlapping CD68-positive signal (data not shown). More macrophages were immunoreactive for PARP9, a pro-inflammatory molecule, in macrophage-rich "unstable" plaques than in macrophage-poor "stable" plaques, while there was no significant difference in PARP14-positive macrophages (FIG. 12, data not shown). While some macrophages in the human plaques co-expressed PARP14 and PARP9, other cells stained positively for either PARP14 or PARP9 alone (data not shown). These lines of in vivo evidence indicate that macrophages in arterial lesions are heterogeneous, which may reflect diverse levels of pro-inflammatory activation in individual cells.

Figure 13A:
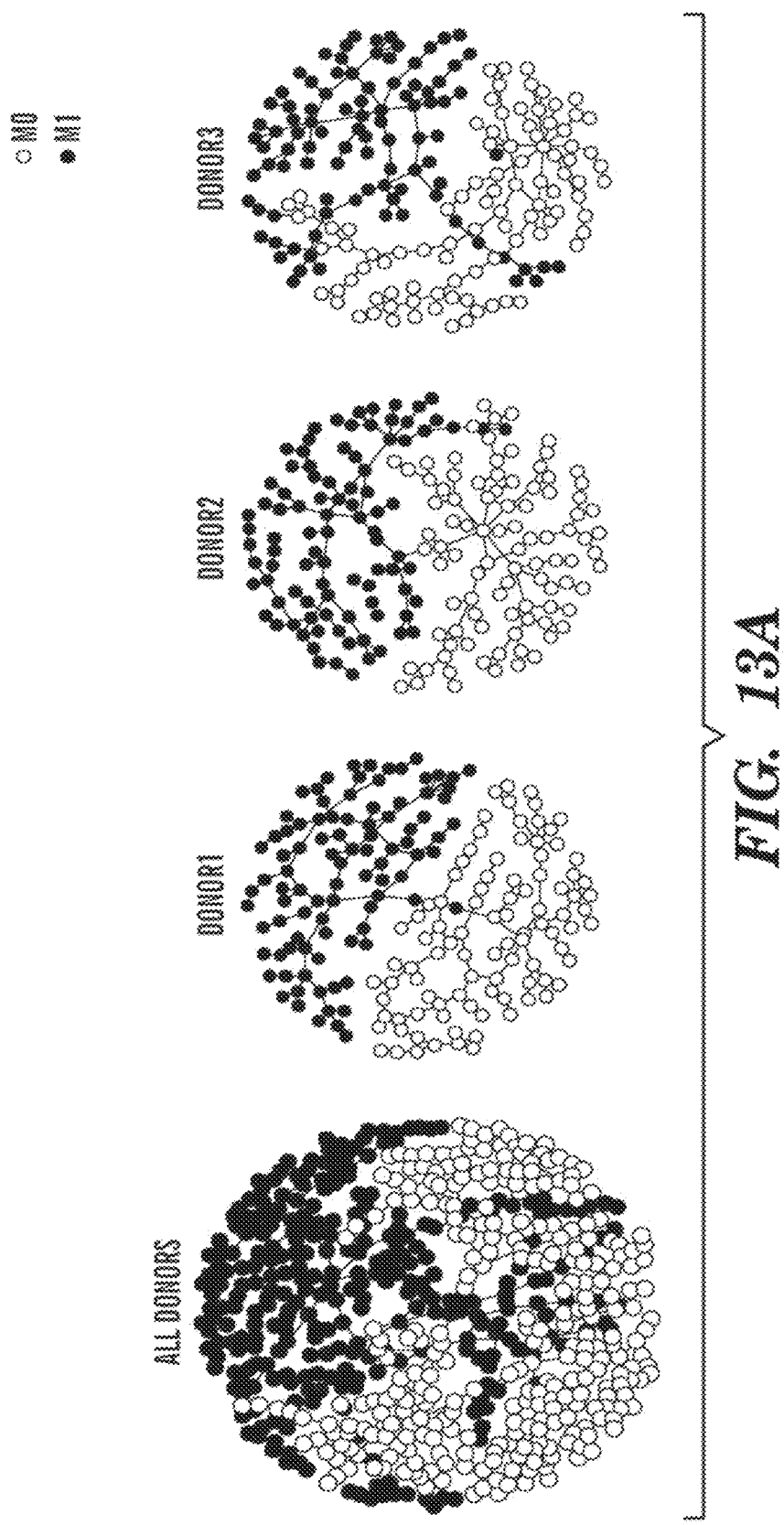
FIGS. 13A-13E show single cell gene expression analysis of CD14+ macrophages (n=3).
Figure 13B:
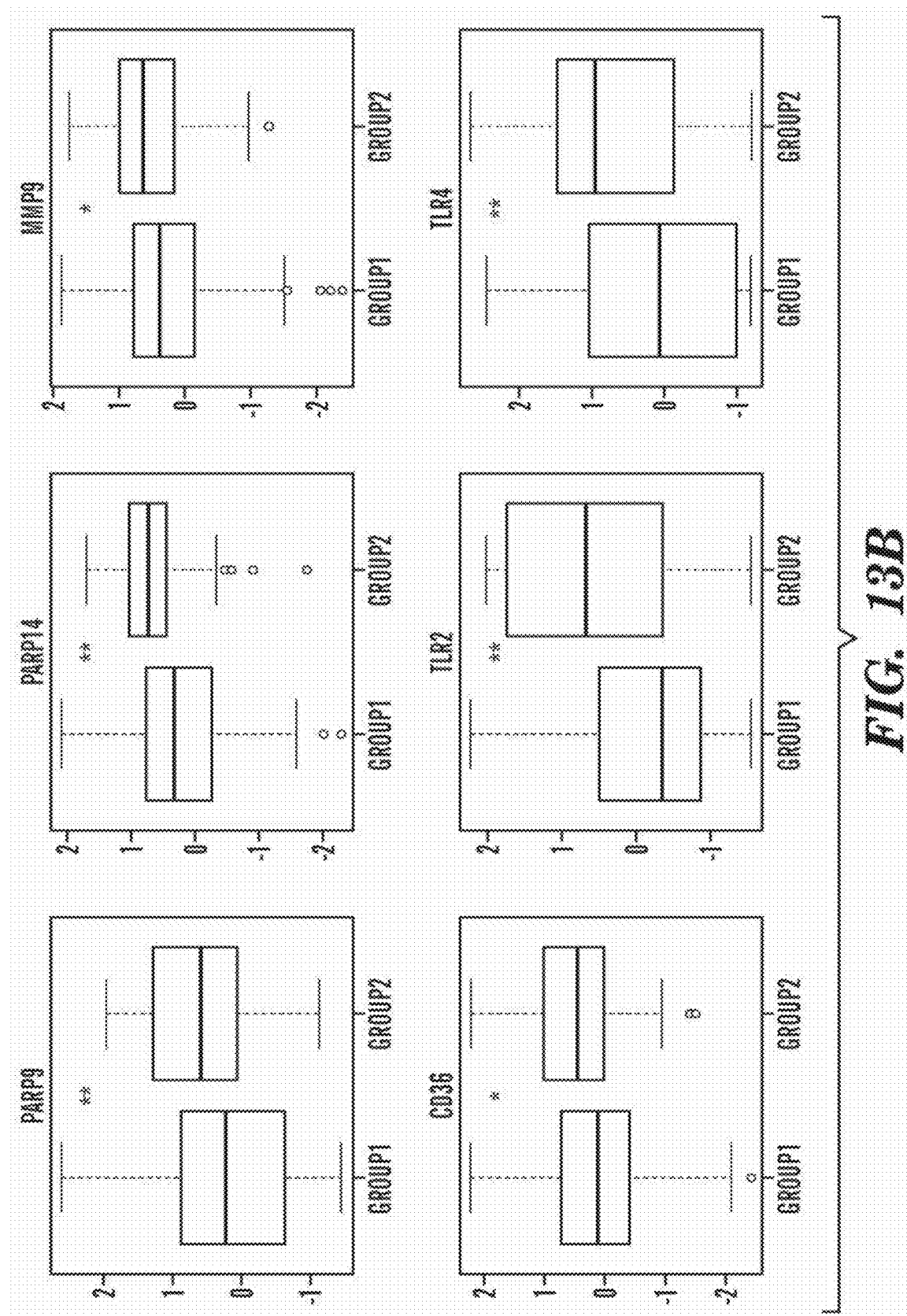
Figure 13C:
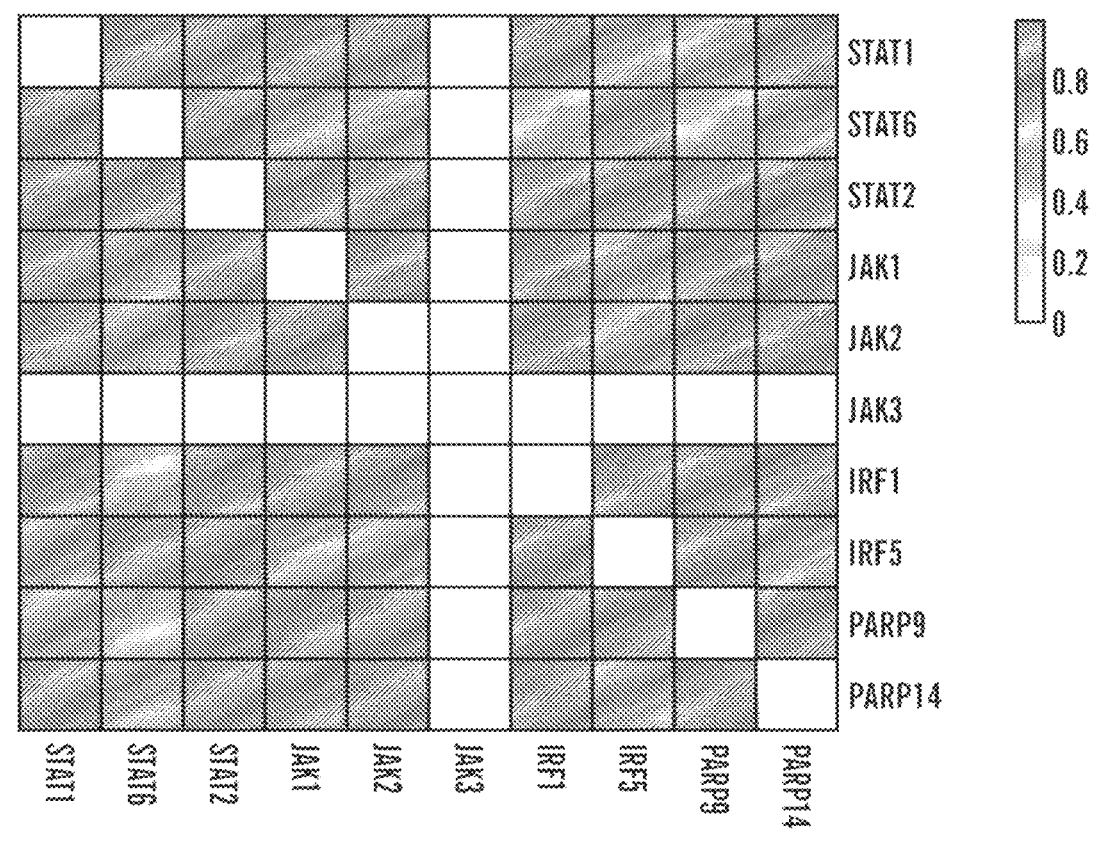
Figure 13D:
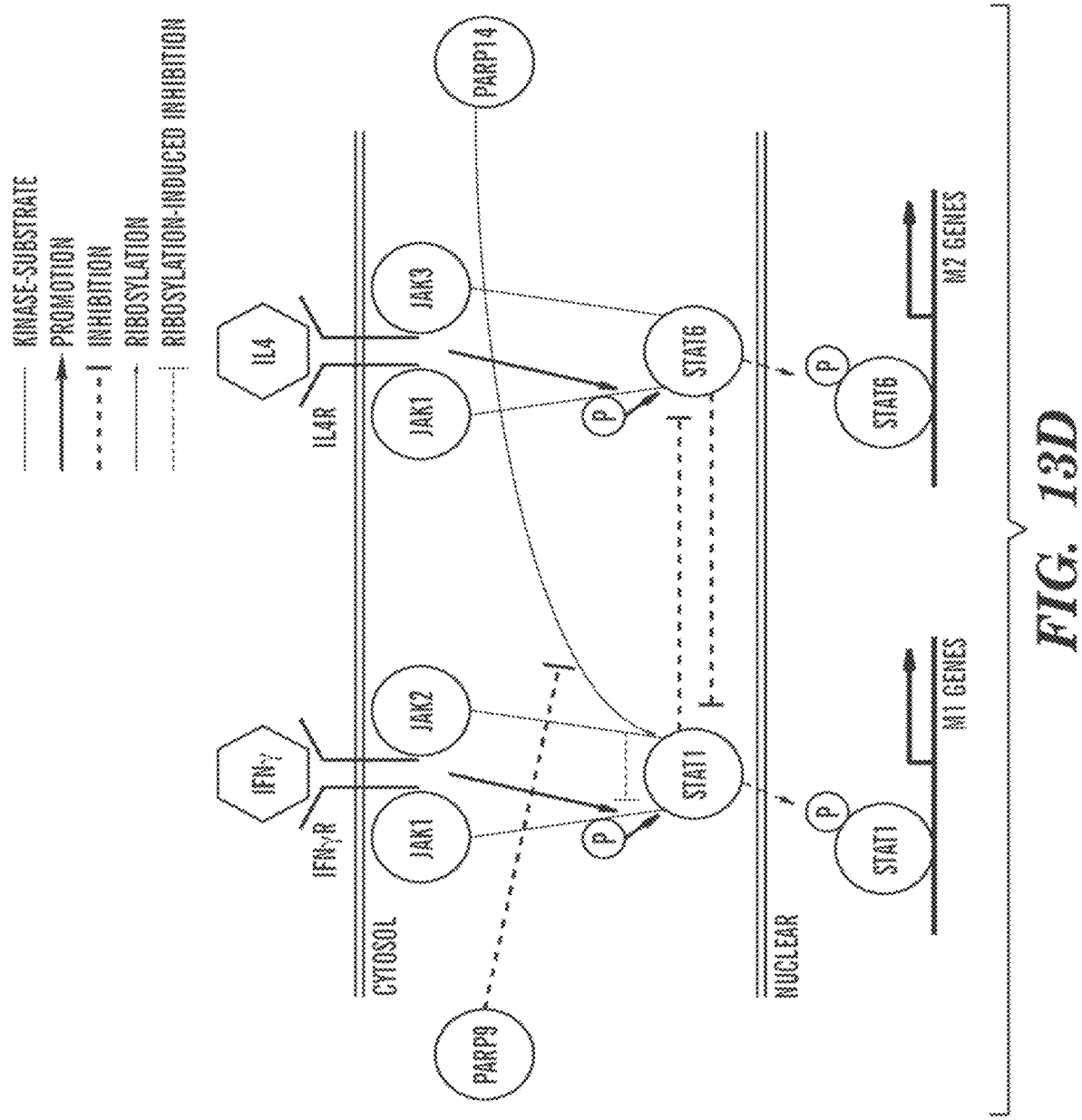
Figure 13E:
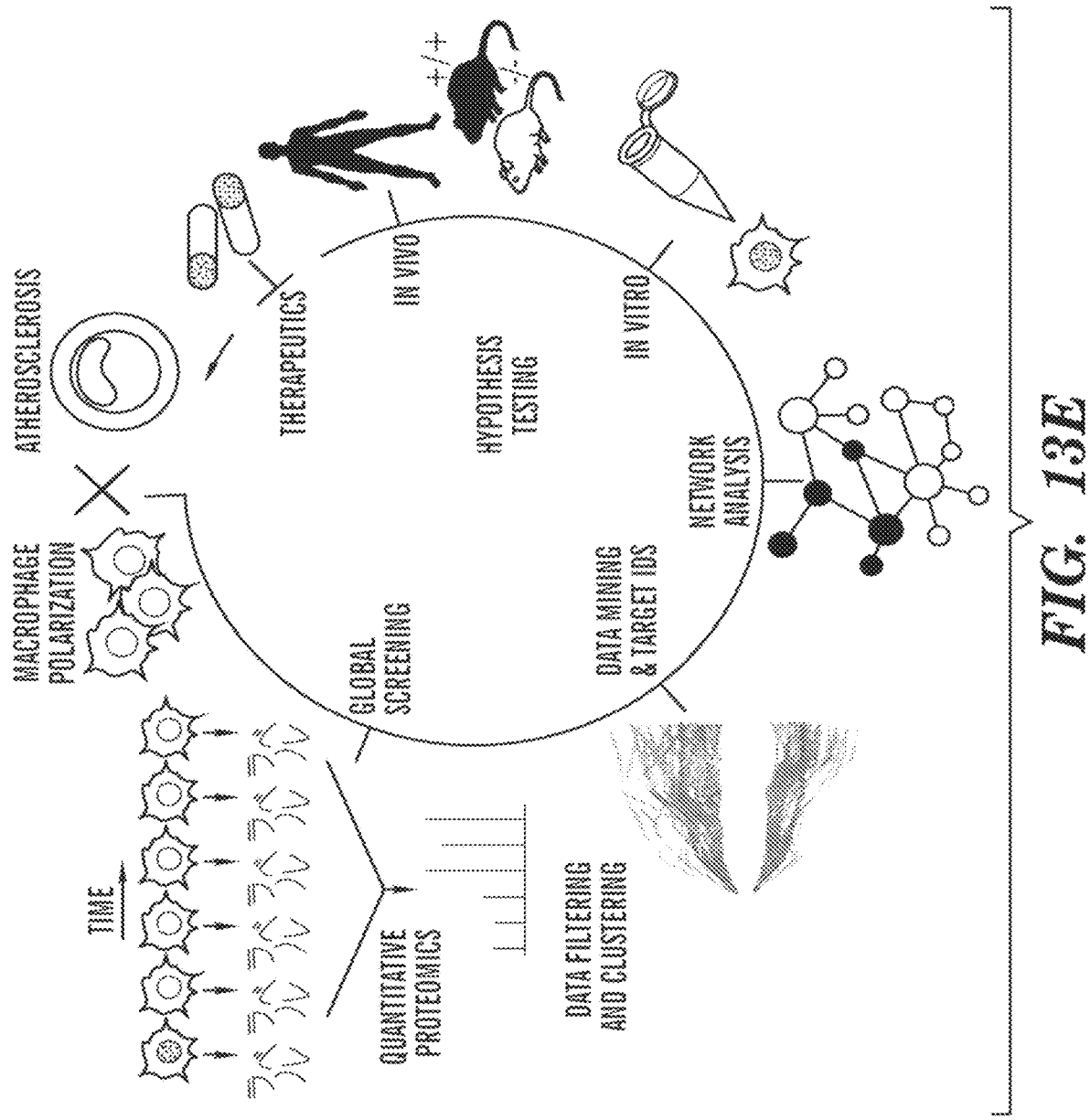
Figure 21:
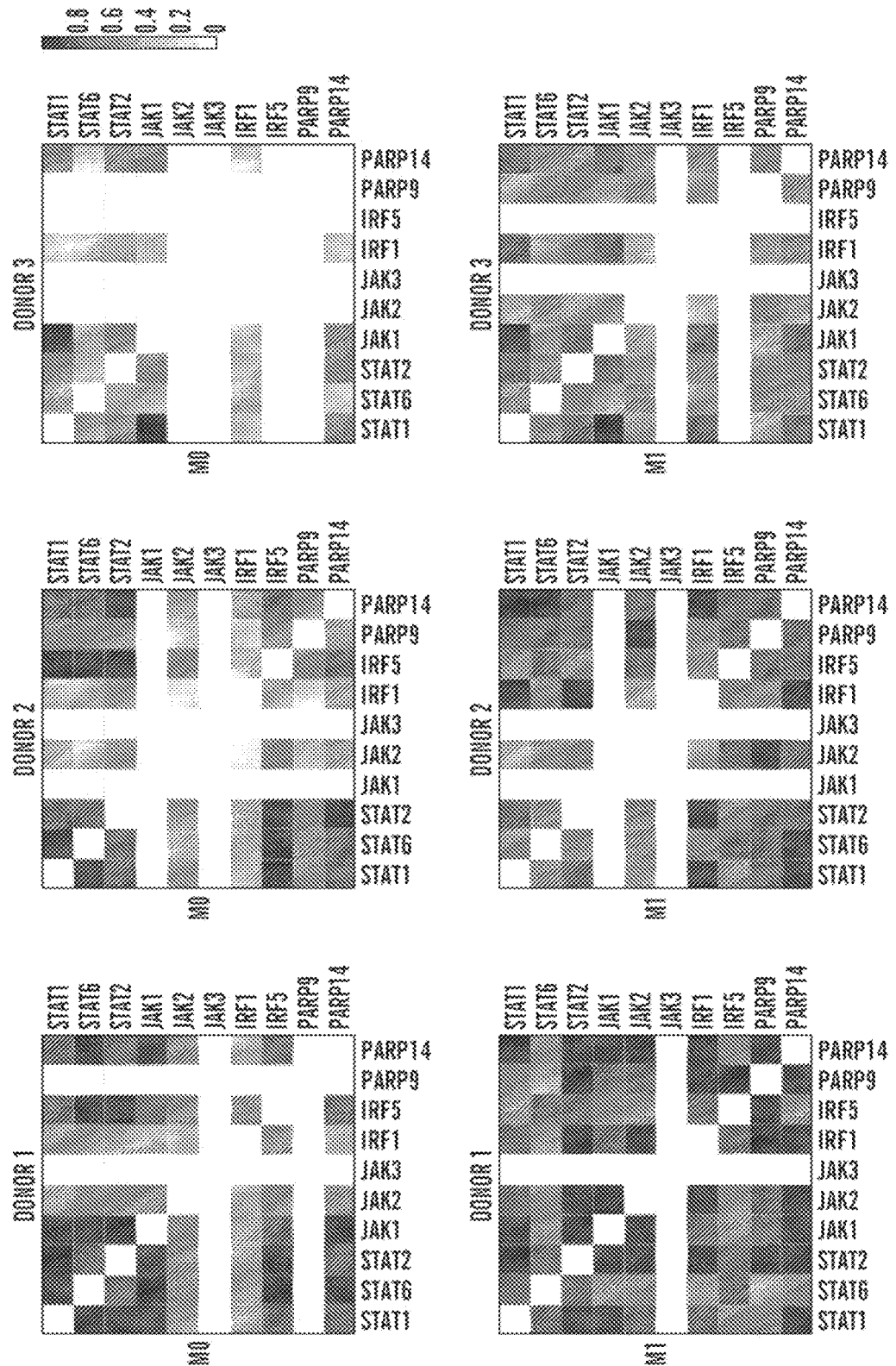
FIG. 21 is a set of similarity maps of CD14-positive PBMCs and genes that play important roles in macrophage polarization in addition to PARP9/14. Similarity maps of samples from all donors (Donor 1 to 3) in both M0 and M1 conditions. PARP9/14 are closely associated with STAT1,6, 2, JAK1,2,3, IRF1 and IRF5 in M1 condition, compared to M0 condition.

Single Cell Analysis of Primary Human Macrophages in the M1 Condition Linked PARP9 and PARP14 with Other Key Components of IFNγ Signaling The diversity in expression patterns of PARP9 and PARP14 in human plaques precipitated the additional assessment of macrophage sub-populations using single-cell gene expression profiling (BioMark, Fluidigm)(37) of PBMC-derived human CD14-positive macrophages. Examined cell numbers were 86 in M0 and 84 in M1 of Donor 1, 93 in M0 and 86 in M1 of Donor 2, and 90 in M0 and 81 in M1 of Donor3, respectively. Specifically, an examination investigated whether M0 cells as an entire group increase M1 gene expression or if individual cells respond differently to IFNγ. Further analysis highlighted the expression patterns of 63 target genes in M0 and M1 macrophages derived from three different donors (n=3). The distance across every cell was evaluated based on their gene expression similarity (Manhattan distance) (world-wide web of the Dictionary of Algorithms and Data Structures at the National Institute of Standards and Technology). The distances are stored as a distance matrix, and represented as a distance-based graph. By combining all 6 chips of two conditions (M0/M1) in three donors, M0 cells (light grey) and M1 cells (dark grey) are clearly segregated. However, there are "trails" of M1 that eat into the M0 phenotype. Conversely, M0 cells do not mix into the M1 space. Although same analysis in each donors demonstrates donor-donor variation, similar patterns were observed across three donors (FIG. 13A). These findings indicate that the "M1-polarized" macrophages are heterogeneous. Similarly, Pearson correlation (38) by expression levels of 63 genes of all cells of all conditions/donors also revealed heterogeneity of CD14+ PBMCs. Cell similarity matrix (data not shown) shows not only distinct distribution of IFNγ-stimulated M1 cells (1), unstimulated M0 cells (2) and mixed population of these (3), but also subpopulations within each population. Specifically, there were at least two subgroups (data not shown) in IFNγ-stimulated M1 cells, and genes related to macrophage functions were examined. Both PARP9 and PARP14 were significantly higher in Group 2 than Group 1. Interestingly, protease MMP9 and pattern recognition receptors, such as CD36, TLR2 and TLR4, were higher in Group2, indicating that macrophages in Group2 were further activated and PARP9 and PARP14 may play roles in such activated macrophages (FIG. 13B). Correlation matrix of genes across all cells (data not shown) shows that PARP9 and PARP14 are closely associated with genes such as JAK, STAT and IRF genes, which are known to participate in IFNγ signaling. This correlation is highly specific in these genes, and does not extend to other genes that were tested in this assay Moreover, it was found that the internal-cluster association of PARP9 and PARP14 are closely correlated with these IFNγ pathway genes, such as STAT1,2,6, JAK1,2 and IRF1,5, except JAK3 (FIG. 13C). Of interest, these correlations are clearly enhanced in M1 (IFNγ stimulation) compared to M0 (unstimulated) (FIG. 21).

DISCUSSION

The present study shows that PARP9 and PARP14 regulate macrophage activation. The specific novel findings demonstrated in this report include: 1) PARP9 promotes activation of mouse and human macrophages; 2) PARP14 suppresses activation of mouse and human macrophages; 3) PARP9 and PARP14 appear to have physical and functional interactions; 4) PARP9 and PARP14 closely interacts with components of IFNγ signaling in macrophages; 5) PARP14 deficiency in vivo accelerates macrophage activation and arterial lesion development in mice; 6) human M1 macrophages derived from PBMC contain a subset of cells; and 7) the PARP9 and PARP14 interactome has significant proximity to the coronary artery disease module (network analysis). The multidisciplinary approach has aimed to establish the unambiguous evidence for the role of PARP9 and PARP14 using multiscale in vitro and in vivo studies.

This study chose IFNγ and IL-4 as examples of typical M1 and M2 stimulators, respectively, for global screening. Mouse and human macrophage cell lines were used in this established model to avoid donor variations of primary macrophages, particularly of the ones derived from human circulating monocytes. The use of a simplified model in cell lines helps to obtain reliable and reproducible data from otherwise exhausting global proteome analysis. Nevertheless, the key results on the functionality of PARP9 and PARP14 were validated in primary macrophages. Furthermore, single-cell analysis of human primary macrophages revealed that close links among PARP9, PARP14, and IFNγ pathway-related molecules (e.g, JAK1, JAK2, STAT1, STATE), indicating that these PARP family members contribute critically to the process of M1 macrophage polarization and further indicating that the key findings, initially led by proteomics in cell lines, are clinically translatable.

Accumulating in vitro evidence has established this model. Its significance in vitro, particularly in human lesions, however remains incompletely understood. The in vitro findings were thus validated in human arterial lesions and a mouse model to provide clinically translatable evidence. Human and mouse atherosclerotic plaque macrophages express PARP9 and PARP14. In humans, macrophages of more "unstable" plaques contained greater amounts of pro-inflammatory PARP9. Four macrophage sub-populations were identified in human lesions: PARP9+/PARP14+; PARP9+/PARP14−; PARP9−/PARP14+; and PARP9−/PARP14+. Interestingly, single-cell gene expression analysis further revealed that, in human primary macrophages, "M1-polarized" cells remained heterogenous and that subpopulations within M1 may have different functions. Bioinformatic analysis on single cell gene profiling also demonstrated that, in M1 macrophages, PARP9 and PARP14 are closely associated with known components of the IFNγ signaling pathway, further supporting the novel findings on the role of these PARP family members on pro-inflammatory macrophage activation.

To explore the evidence for the anti-atherogenic role of PARP14 beyond the in vitro M1/M2 paradigm, a genetically altered mouse strain for PARP14 was used. Genetic deletion of PARP14 indeed promoted macrophage activation and accumulation in the intima of mechanically injured arteries, offering in vivo proof of concept. In addition, the possible role of PARP9 or PARP14 in activation of EC and SMC was further explored.

The study described herein further revealed the new biology for relatively understudied members of the PARP family—PARP9 and PARP14. Two independent lines of evidence—ADP-ribosylation assays and LC-MS/MS—indicated that PARP14 may have the ability to ADP-ribosylate STAT1, presumably at the sites near its key phosphorylation site. Interestingly, PARP9 may inhibit this process. It should be noted that IFNγ induces PARP14 protein earlier than PARP9. This interaction may in part explain why PARP9 and PARP14 exert opposing effects on macrophage polarization, although both PARPs increase in the M1 condition and decrease in M2.

TABLE 1

The time point assignments to each TMT channel

| | 126 | 127 | 128 | 129 | 130 | 131 |
|---|---|---|---|---|---|---|
| TMT channels in RAW 264.7 cells | | | | | | |
| M0 | 72 hrs | 48 hrs | 24 hrs | 12 hrs | 8 hrs | 0 hrs |
| M1 | 0 hrs | 8 hrs | 12 hrs | 24 hrs | 48 hrs | 72 hrs |
| M2 | 0 hrs | 8 hrs | 12 hrs | 24 hrs | 48 hrs | 72 hrs |
| TMT channels in THP-1 cells | | | | | | |
| M0 | 0 hrs | 8 hrs | 12 hrs | 24 hrs | 48 hrs | 72 hrs |
| M1 | 0 hrs | 8 hrs | 12 hrs | 24 hrs | 48 hrs | 72 hrs |
| M2 | 0 hrs | 8 hrs | 12 hrs | 24 hrs | 48 hrs | 72 hrs |

TABLE 2

Overview of quantified proteomes

| RAW264.7 cells | | | THP1 cells | | |
|---|---|---|---|---|---|
| M0 | M1 | M2 | M0 | M1 | M2 |
| Total proteins quantified by MS/MS | | | | | |
| 4,234 | 6,393 | 5,470 | 6,338 | 6,187 | 6,722 |
| Filtered for the number of unique peptides >1 | | | | | |
| 2,934 | 4,786 | 3,966 | 4,713 | 4,623 | 5,027 |

TABLE 3

| Disease Module | size | p-value |
|---|---|---|
| Cardiomyopathy | 49 | 0.103 |
| Cardiovascular Risk Factors | 25 | 0.135 |
| Coronary Artery Disease | 76 | 0.001 |
| Heart Failure | 15 | 0.175 |
| Hypercholesterolemia | 15 | 0.214 |
| Hyperlipidemia | 15 | 0.092 |
| Hypertension | 34 | 0.213 |
| Metabolic Traits | 44 | 0.074 |
| Osteoporosis | 53 | 0.006 |
| Sudden Cardiac Arrest | 24 | 0.239 |

REFERENCES FOR EXAMPLE 2

1. M. Writing Group, D. Lloyd-Jones, et al., American Heart Association Statistics, S. Stroke Statistics, Heart disease and stroke statistics—2010 update: a report from the American Heart Association. Circulation 121, e46-e215 (2010).
2. A. E. Moran et al., The global burden of ischemic heart disease in 1990 and 2010: the Global Burden of Disease 2010 study. Circulation 129, 1493-1501 (2014).
3. C. K. Glass, J. L. Witztum, Atherosclerosis. the road ahead. Cell 104, 503-516 (2001).
4. C. P. Liang, et al., The macrophage at the crossroads of insulin resistance and atherosclerosis. Circ Res 100, 1546-1555 (2007).
5. G. J. Randolph, Mechanisms that regulate macrophage burden in atherosclerosis. Circ Res 114, 1757-1771 (2014).
6. I. Tabas, Macrophage death and defective inflammation resolution in atherosclerosis. Nat Rev Immunol 10, 36-46 (2010).
7. M. Aikawa, P. Libby, The vulnerable atherosclerotic plaque: pathogenesis and therapeutic approach. Cardiovasc Pathol 13, 125-138 (2004).
8. P. M. Ridker, T. F. Luscher, Anti-inflammatory therapies for cardiovascular disease. European heart journal 35, 1782-1791 (2014).
9. C. K. Glass, J. M. Olefsky, Inflammation and lipid signaling in the etiology of insulin resistance. Cell Metab 15, 635-645 (2012).
10. M. F. Gregor, G. S. Hotamisligil, Inflammatory mechanisms in obesity. Annual review of immunology 29, 415-445 (2011).
11. G. Fredman, L. Ozcan, I. Tabas, Common therapeutic targets in cardiometabolic disease. Science translational medicine 6, 239ps235 (2014).
12. D. Fukuda, et al., Notch ligand delta-like 4 blockade attenuates atherosclerosis and metabolic disorders. Proc Natl Acad Sci USA 109, E1868-1877 (2012).

13. M. Aikawa, et al., An HMG-CoA reductase inhibitor, cerivastatin, suppresses growth of macrophages expressing matrix metalloproteinases and tissue factor in vivo and in vitro. Circulation 103, 276-283 (2001).
14. P. Libby, The forgotten majority: unfinished business in cardiovascular risk reduction. J Am Coll Cardiol 46, 1225-1228 (2005).
15. S. Gordon, A. Mantovani, Diversity and plasticity of mononuclear phagocytes. Eur J Immunol 41, 2470-2472 (2011).
16. K. Ley, Y. I. Miller, C. C. Hedrick, Monocyte and macrophage dynamics during atherogenesis. Arterioscler Thromb Vasc Biol 31, 1506-1516 (2011).
17. S. K. Biswas, A. Mantovani, Orchestration of metabolism by macrophages. Cell Metab 15, 432-437 (2012).
18. E. K. Koltsova, C. C. Hedrick, K. Ley, Myeloid cells in atherosclerosis: a delicate balance of anti-inflammatory and proinflammatory mechanisms. Curr Opin Lipidol 24, 371-380 (2013).
19. T. Lawrence, G. Natoli, Transcriptional regulation of macrophage polarization: enabling diversity with identity. Nat Rev Immunol 11, 750-761 (2011).
20. K. J. Moore, F. J. Sheedy, E. A. Fisher, Macrophages in atherosclerosis: a dynamic balance. Nat Rev Immunol 13, 709-721 (2013).
21. P. J. Murray, et al., Macrophage Activation and Polarization: Nomenclature and Experimental Guidelines. Immunity 41, 14-20 (2014).
22. F. K. Swirski, M. Nahrendorf, Leukocyte behavior in atherosclerosis, myocardial infarction, and heart failure. Science 339, 161-166 (2013).
23. F. Koch-Nolte, et al., Mammalian ADP-ribosyltransferases and ADP-ribosylhydrolases. Front Biosci 13, 6716-6729 (2008).
24. K. L. Feijs, et al., Expanding functions of intracellular resident mono-ADP-ribosylation in cell physiology. Febs J 280, 3519-3529 (2013).
25. S. H. Cho, et al., Glycolytic rate and lymphomagenesis depend on PARP14, an ADP ribosyltransferase of the B aggressive lymphoma (BAL) family. Proc Natl Acad Sci USA 108, 15972-15977 (2011).
26. P. Mehrotra, et al., PARP-14 functions as a transcriptional switch for Stat6-dependent gene activation. J Biol Chem 286, 1767-1776 (2011).
27. R. C. Aguiar, et al., B-aggressive lymphoma family proteins have unique domains that modulate transcription and exhibit poly(ADP-ribose) polymerase activity. J Biol Chem 280, 33756-33765 (2005).
28. P. Juszczynski, et al., BAL1 and BBAP are regulated by a gamma interferon-responsive bidirectional promoter and are overexpressed in diffuse large B-cell lymphomas with a prominent inflammatory infiltrate. Mol Cell Biol 26, 5348-5359 (2006).
29. A. L. Barabasi, et al., Network medicine: a network-based approach to human disease. Nat Rev Genet 12, 56-68 (2011).
30. K. I. Goh, et al., The human disease network. Proc Natl Acad Sci USA 104, 8685-8690 (2007).
31. S. Kohler, et al., Walking the interactome for prioritization of candidate disease genes. Am J Hum Genet 82, 949-958 (2008).
32. E. Maier, et al., STATE-dependent and -independent mechanisms in Th2 polarization. Eur J Immunol 42, 2827-2833 (2012).
33. K. Sikorski, et al., STAT1 as a central mediator of IFNgamma and TLR4 signal integration in vascular dysfunction. Jak-Stat 1, 241-249 (2012).
34. T. Atsumi, R. et al., Inflammation amplifier, a new paradigm in cancer biology. Cancer research 74, 8-14 (2014).
35. S. Goenka, M. Boothby, Selective potentiation of Stat-dependent gene expression by collaborator of Stat6 (CoaSt6), a transcriptional cofactor. Proc Natl Acad Sci USA 103, 4210-4215 (2006).
36. S. H. Cho, et al., PARP-14, a member of the B aggressive lymphoma family, transduces survival signals in primary B cells. Blood 113, 2416-2425 (2009).
37. A. Grover, et al., Erythropoietin guides multipotent hematopoietic progenitor cells toward an erythroid fate. J Exp Med 211, 181-188 (2014).
38. K. Pearson, Mathematical Contributions to the Theory of Evolution. III. Regression, Heredity and Panmixia. Philosophical Transactions of the Royal Society of London 187, 253-318 (1896).
39. S. M. Hengel, et al., Evaluation of SDS depletion using an affinity spin column and IMS-MS detection. Proteomics 12, 3138-3142 (2012).
40. S. M. Hengel, et al., Tandem mass spectrometry investigation of ADP-ribosylated kemptide. J Am Soc Mass Spectrom 20, 477-483 (2009).
41. J. K. Eng, et al., An approach to correlate tandem mass spectral data of peptides with amino acid sequences in a protein database. J Am Soc Mass Spectrom 5, 976-989 (1994).
42. J. E. Elias, S. P. Gygi, Target-decoy search strategy for increased confidence in large-scale protein identifications by mass spectrometry. Nat Methods 4, 207-214 (2007).
43. L. Kall, et al., Assigning significance to peptides identified by tandem mass spectrometry using decoy databases. Journal of proteome research 7, 29-34 (2008).
44. A. E. R. Chris Fraley, Model-Based Clustering, Discriminant Analysis, and Density Estimation. Journal of the American Statistical Association 97, 611-631 (2002).
45. M. Kirchner, et al., Computational protein profile similarity screening for quantitative mass spectrometry experiments. Bioinformatics 26, 77-83 (2010).
46. I. Lee, et al., Prioritizing candidate disease genes by network-based boosting of genome-wide association data. Genome Res 21, 1109-1121 (2011).
47. E. Hitti, et al., Mitogen-activated protein kinase-activated protein kinase 2 regulates tumor necrosis factor mRNA stability and translation mainly by altering tristetraprolin expression, stability, and binding to adenine/uridine-rich element. Mol Cell Biol 26, 2399-2407 (2006).
48. P. Mehrotra, et al., Poly (ADP-ribose) polymerase 14 and its enzyme activity regulates T(H)2 differentiation and allergic airway disease. The Journal of allergy and clinical immunology 131, 521-531 e521-512 (2013).
49. H. Iwata, et al., Bone marrow-derived cells contribute to vascular inflammation but do not differentiate into smooth muscle cell lineages. Circulation 122, 2048-2057 (2010).
50. M. Sata, et al., Endothelial nitric oxide synthase is essential for the HMG-CoA reductase inhibitor cerivastatin to promote collateral growth in response to ischemia. FASEB journal: official publication of the Federation of American Societies for Experimental Biology 15, 2530-2532 (2001).
51. C. P. Paul, et al., Effective expression of small interfering RNA in human cells. Nature biotechnology 20, 505-508 (2002).

What is claimed:

1. A method of inhibiting excessive or sustained inflammation in a subject in need thereof, the method comprising: contacting a population of monocytes and/or macrophages from the subject with an effective amount of a small molecule that inhibits poly (ADP-ribose) polymerase family, member 9 (PARP9), wherein the small molecule is selected from the group consisting of: DR 2313.

2. The method of claim 1, wherein the population of monocytes or macrophages are contacted ex vivo, in vitro, or in vivo.

3. The method of claim 1, wherein the small molecule is formulated with a pharmaceutically acceptable carrier or diluent.

* * * * *

SEQUENCE LISTING

<160> NUMBER OF SEQ ID NOS: 63

<210> SEQ ID NO 1
<211> LENGTH: 19
<212> TYPE: DNA
<213> ORGANISM: Homo sapiens

<400> SEQUENCE: 1
gatttaactt gttctgtaa				19

<210> SEQ ID NO 2
<211> LENGTH: 19
<212> TYPE: DNA
<213> ORGANISM: Homo sapiens

<400> SEQUENCE: 2
ttgaagatat gctttgtaa				19

<210> SEQ ID NO 3
<211> LENGTH: 19
<212> TYPE: DNA
<213> ORGANISM: Homo sapiens

<400> SEQUENCE: 3
gccataggct gtttcagca				19

<210> SEQ ID NO 4
<211> LENGTH: 19
<212> TYPE: DNA
<213> ORGANISM: Homo sapiens

<400> SEQUENCE: 4
gtctccatca cagaaatta				19

<210> SEQ ID NO 5
<211> LENGTH: 19
<212> TYPE: DNA
<213> ORGANISM: Homo sapiens

<400> SEQUENCE: 5
tggtggattt gaaatccaa				19

<210> SEQ ID NO 6
<211> LENGTH: 19
<212> TYPE: DNA
<213> ORGANISM: Homo sapiens

<400> SEQUENCE: 6
gagttgaaat gaaatcgga				19

<210> SEQ ID NO 7
<211> LENGTH: 19
<212> TYPE: DNA
<213> ORGANISM: Homo sapiens

<400> SEQUENCE: 7
ctttaaagct gcttcagaa				19

<210> SEQ ID NO 8
<211> LENGTH: 19
<212> TYPE: DNA
<213> ORGANISM: Homo sapiens

<400> SEQUENCE: 8

```
atgacagtgt ggttgacaa                                                  19

<210> SEQ ID NO 9
<211> LENGTH: 19
<212> TYPE: DNA
<213> ORGANISM: Homo sapiens

<400> SEQUENCE: 9
caaacagttt gttgccaga                                                  19

<210> SEQ ID NO 10
<211> LENGTH: 19
<212> TYPE: DNA
<213> ORGANISM: Homo sapiens

<400> SEQUENCE: 10
tcctgtgcct ccaactcaa                                                  19

<210> SEQ ID NO 11
<211> LENGTH: 19
<212> TYPE: DNA
<213> ORGANISM: Homo sapiens

<400> SEQUENCE: 11
gactggtgct cttggagaa                                                  19

<210> SEQ ID NO 12
<211> LENGTH: 19
<212> TYPE: DNA
<213> ORGANISM: Homo sapiens

<400> SEQUENCE: 12
ggaagccaat gatgagtaa                                                  19

<210> SEQ ID NO 13
<211> LENGTH: 19
<212> TYPE: DNA
<213> ORGANISM: Homo sapiens

<400> SEQUENCE: 13
ttcagaattt cctaaacct                                                  19

<210> SEQ ID NO 14
<211> LENGTH: 19
<212> TYPE: DNA
<213> ORGANISM: Homo sapiens

<400> SEQUENCE: 14
ctggaaacat ggaaataaa                                                  19

<210> SEQ ID NO 15
<211> LENGTH: 19
<212> TYPE: DNA
<213> ORGANISM: Homo sapiens

<400> SEQUENCE: 15
ctctgaattt gtgtacaaa                                                  19

<210> SEQ ID NO 16
<211> LENGTH: 19
<212> TYPE: DNA
<213> ORGANISM: Homo sapiens
```

```
<400> SEQUENCE: 16
ccatcaatct gatgggatt                                                    19

<210> SEQ ID NO 17
<211> LENGTH: 19
<212> TYPE: DNA
<213> ORGANISM: Homo sapiens

<400> SEQUENCE: 17
cagataagct gatctatgt                                                    19

<210> SEQ ID NO 18
<211> LENGTH: 19
<212> TYPE: DNA
<213> ORGANISM: Homo sapiens

<400> SEQUENCE: 18
gggttagttt gcaagggaa                                                    19

<210> SEQ ID NO 19
<211> LENGTH: 19
<212> TYPE: DNA
<213> ORGANISM: Homo sapiens

<400> SEQUENCE: 19
cagatttgga gatatataa                                                    19

<210> SEQ ID NO 20
<211> LENGTH: 19
<212> TYPE: DNA
<213> ORGANISM: Homo sapiens

<400> SEQUENCE: 20
tgctgagttt gaacaatta                                                    19

<210> SEQ ID NO 21
<211> LENGTH: 19
<212> TYPE: DNA
<213> ORGANISM: Homo sapiens

<400> SEQUENCE: 21
ccattaacca caatgactt                                                    19

<210> SEQ ID NO 22
<211> LENGTH: 19
<212> TYPE: DNA
<213> ORGANISM: Homo sapiens

<400> SEQUENCE: 22
gcagacggca gatgtaatt                                                    19

<210> SEQ ID NO 23
<211> LENGTH: 19
<212> TYPE: DNA
<213> ORGANISM: Homo sapiens

<400> SEQUENCE: 23
cccacatgat attacagtt                                                    19

<210> SEQ ID NO 24
<211> LENGTH: 19
<212> TYPE: DNA
<213> ORGANISM: Homo sapiens
```

```
<400> SEQUENCE: 24
gcaggagttg aaatgaaat                                                   19

<210> SEQ ID NO 25
<211> LENGTH: 19
<212> TYPE: DNA
<213> ORGANISM: Homo sapiens

<400> SEQUENCE: 25
gccatcaatc tgatgggat                                                   19

<210> SEQ ID NO 26
<211> LENGTH: 19
<212> TYPE: DNA
<213> ORGANISM: Homo sapiens

<400> SEQUENCE: 26
gctggtatgg ccttacctt                                                   19

<210> SEQ ID NO 27
<211> LENGTH: 19
<212> TYPE: DNA
<213> ORGANISM: Homo sapiens

<400> SEQUENCE: 27
cctcttgcag ttgttctttt                                                  19

<210> SEQ ID NO 28
<211> LENGTH: 19
<212> TYPE: DNA
<213> ORGANISM: Homo sapiens

<400> SEQUENCE: 28
cctttactag aggagataa                                                   19

<210> SEQ ID NO 29
<211> LENGTH: 19
<212> TYPE: RNA
<213> ORGANISM: Homo sapiens

<400> SEQUENCE: 29
uaaucaaagg ucucuuaug                                                   19

<210> SEQ ID NO 30
<211> LENGTH: 19
<212> TYPE: RNA
<213> ORGANISM: Homo sapiens

<400> SEQUENCE: 30
uaaugcuuaa gguccucau                                                   19

<210> SEQ ID NO 31
<211> LENGTH: 19
<212> TYPE: RNA
<213> ORGANISM: Homo sapiens

<400> SEQUENCE: 31
ucauuauacu gccauucua                                                   19

<210> SEQ ID NO 32
<211> LENGTH: 19
<212> TYPE: RNA
```

```
<213> ORGANISM: Homo sapiens

<400> SEQUENCE: 32
gaacucuuga caucauuuc                                                19

<210> SEQ ID NO 33
<211> LENGTH: 19
<212> TYPE: RNA
<213> ORGANISM: Homo sapiens

<400> SEQUENCE: 33
aauuacaucu gccgucugc                                                19

<210> SEQ ID NO 34
<211> LENGTH: 19
<212> TYPE: RNA
<213> ORGANISM: Homo sapiens

<400> SEQUENCE: 34
uuuguggcaa gaaauuccg                                                19

<210> SEQ ID NO 35
<211> LENGTH: 19
<212> TYPE: RNA
<213> ORGANISM: Homo sapiens

<400> SEQUENCE: 35
uuaaucaaca gggcugcca                                                19

<210> SEQ ID NO 36
<211> LENGTH: 19
<212> TYPE: RNA
<213> ORGANISM: Homo sapiens

<400> SEQUENCE: 36
uacagccaaa cuuauucug                                                19

<210> SEQ ID NO 37
<211> LENGTH: 19
<212> TYPE: RNA
<213> ORGANISM: Mus musculus

<400> SEQUENCE: 37
cuugaaagcu uuacguaua                                                19

<210> SEQ ID NO 38
<211> LENGTH: 19
<212> TYPE: RNA
<213> ORGANISM: Mus musculus

<400> SEQUENCE: 38
cagcaauagg aacgggaaa                                                19

<210> SEQ ID NO 39
<211> LENGTH: 19
<212> TYPE: RNA
<213> ORGANISM: Mus musculus

<400> SEQUENCE: 39
ccaaagaacu ugaucaaca                                                19

<210> SEQ ID NO 40
<211> LENGTH: 19
```

```
<212> TYPE: RNA
<213> ORGANISM: Mus musculus

<400> SEQUENCE: 40
cguaguagca aaagcgaua                                                    19

<210> SEQ ID NO 41
<211> LENGTH: 19
<212> TYPE: RNA
<213> ORGANISM: Mus musculus

<400> SEQUENCE: 41
acacaauguc uucgaaauu                                                    19

<210> SEQ ID NO 42
<211> LENGTH: 19
<212> TYPE: RNA
<213> ORGANISM: Mus musculus

<400> SEQUENCE: 42
ccagacagcu aucgaauua                                                    19

<210> SEQ ID NO 43
<211> LENGTH: 19
<212> TYPE: RNA
<213> ORGANISM: Mus musculus

<400> SEQUENCE: 43
ccaaauauga ucuacgcau                                                    19

<210> SEQ ID NO 44
<211> LENGTH: 19
<212> TYPE: RNA
<213> ORGANISM: Mus musculus

<400> SEQUENCE: 44
cguacacauu ucaacgaua                                                    19

<210> SEQ ID NO 45
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 45
ugguuuacau gucgacuaa                                                    19

<210> SEQ ID NO 46
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 46
ugguuuacau guuguguga                                                    19

<210> SEQ ID NO 47
<211> LENGTH: 19
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 47
ugguuuacau guuuucuga                                                    19

<210> SEQ ID NO 48
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 48
ugguuuacau guuuuccua                                                    19

<210> SEQ ID NO 49
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Gly Thr Ala Leu Phe Leu Val Gly Ser Ser Phe Lys
1               5                   10

<210> SEQ ID NO 50
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Gln Thr Ala Leu Phe Leu Val Gly Ser Ser Phe Lys
1               5                   10

<210> SEQ ID NO 51
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Ala Arg Asp Glu Ile Glu Gly Met Ile Lys
1               5                   10

<210> SEQ ID NO 52
<211> LENGTH: 98
<212> TYPE: PRT
<213> ORGANISM: Homo sapiens

<400> SEQUENCE: 52

Val Met Ala Ala Glu Asn Ile Pro Glu Asn Pro Leu Lys Tyr Leu Tyr
1               5                   10                  15

Pro Asn Ile Asp Lys Asp His Ala Phe Gly Lys Tyr Tyr Ser Arg Pro
            20                  25                  30

Lys Glu Ala Pro Glu Pro Met Glu Leu Asp Gly Pro Lys Gly Thr Gly
        35                  40                  45

Tyr Ile Lys Thr Glu Leu Ile Ser Val Ser Glu Val His Pro Ser Arg
            50                  55                  60

Leu Gln Thr Thr Asp Asn Leu Leu Pro Met Ser Pro Glu Glu Phe Asp
65                  70                  75                  80

Glu Val Ser Arg Ile Val Gly Ser Val Glu Phe Asp Ser Met Met Asn
                85                  90                  95

Thr Val

<210> SEQ ID NO 53
<211> LENGTH: 13
<212> TYPE: PRT
<213> ORGANISM: Homo sapiens

<400> SEQUENCE: 53

Val Met Ala Ala Glu Asn Ile Pro Glu Asn Pro Leu Lys
1               5                   10

<210> SEQ ID NO 54
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Val Met Ala Ala Glu Asn Ile Pro Glu Asn Pro Leu Lys
1               5                   10

<210> SEQ ID NO 55
<211> LENGTH: 13
<212> TYPE: PRT
<213> ORGANISM: Homo sapiens

<400> SEQUENCE: 55

Thr Glu Leu Ile Ser Val Ser Glu Val His Pro Ser Arg
1               5                   10

<210> SEQ ID NO 56
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Thr Glu Leu Ile Ser Val Ser Glu Val His Pro Ser Arg
1               5                   10

<210> SEQ ID NO 57
<211> LENGTH: 12
<212> TYPE: PRT
<213> ORGANISM: Mus musculus

<400> SEQUENCE: 57

Gly Thr Ala Leu Phe Leu Val Gly Ser Ser Phe Lys
1               5                   10

<210> SEQ ID NO 58
<211> LENGTH: 12
<212> TYPE: PRT
<213> ORGANISM: Mus musculus

<400> SEQUENCE: 58

```
Gly Thr Ala Leu Phe Leu Val Gly Ser Ser Phe Lys
1               5                   10

<210> SEQ ID NO 59
<211> LENGTH: 10
<212> TYPE: PRT
<213> ORGANISM: Mus musculus

<400> SEQUENCE: 59

Ala Arg Asp Glu Ile Glu Gly Met Ile Lys
1               5                   10

<210> SEQ ID NO 60
<211> LENGTH: 8
<212> TYPE: PRT
<213> ORGANISM: Mus musculus

<400> SEQUENCE: 60

His Asn Val Phe Glu Ile Leu Lys
1               5

<210> SEQ ID NO 61
<211> LENGTH: 8
<212> TYPE: PRT
<213> ORGANISM: Mus musculus

<400> SEQUENCE: 61

His Asn Val Phe Glu Ile Leu Lys
1               5

<210> SEQ ID NO 62
<211> LENGTH: 8
<212> TYPE: PRT
<213> ORGANISM: Mus musculus

<400> SEQUENCE: 62

His Asn Val Phe Glu Ile Leu Lys
1               5

<210> SEQ ID NO 63
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(21)
<223> OTHER INFORMATION: a, c, t, g, unknown or other

<400> SEQUENCE: 63
aannnnnnnn nnnnnnnnnn ntt                                              23
```